United States Patent
Morant et al.

(10) Patent No.: US 12,269,852 B2
(45) Date of Patent: Apr. 8, 2025

(54) PROCESSES FOR PRODUCING A FERMENTATION PRODUCT

(71) Applicant: NOVOZYMES A/S, Bagsvaerd (DK)

(72) Inventors: Marc Dominique Morant, Frederiksberg (DK); Tomoko Matsui, Chiba (JP); Kirk Matthew Schnorr, Holte (DK); Shiro Fukuyama, Chiba (JP); Noriko Tsutsumi, Chiba (JP); Zhengfang Kang, Raleigh, NC (US)

(73) Assignee: NOVOZYMES A/S, Bagsvaerd (DK)

( * ) Notice: Subject to any disclaimer, the term of this patent is extended or adjusted under 35 U.S.C. 154(b) by 84 days.

(21) Appl. No.: 17/936,076

(22) Filed: Sep. 28, 2022

(65) Prior Publication Data

US 2024/0101991 A1    Mar. 28, 2024

Related U.S. Application Data

(62) Division of application No. 16/624,164, filed as application No. PCT/US2018/039443 on Jun. 26, 2018, now Pat. No. 11,584,783.

(60) Provisional application No. 62/526,133, filed on Jun. 28, 2017.

(51) Int. Cl.
| | |
|---|---|
| C12P 7/06 | (2006.01) |
| C07K 14/39 | (2006.01) |
| C07K 14/395 | (2006.01) |
| C12N 9/24 | (2006.01) |
| C12N 9/26 | (2006.01) |
| C12N 15/81 | (2006.01) |
| C12P 19/14 | (2006.01) |

(52) U.S. Cl.
CPC ............ *C07K 14/39* (2013.01); *C12N 9/2402* (2013.01); *C12N 9/2408* (2013.01); *C12N 15/81* (2013.01); *C12P 7/06* (2013.01); *C12P 19/14* (2013.01); *C12Y 302/01001* (2013.01); *C12Y 302/01003* (2013.01); *C12Y 302/01028* (2013.01); *C12Y 302/01093* (2013.01)

(58) Field of Classification Search
CPC ......... C12N 9/2408; C12N 15/81; C12P 7/06; C12Y 302/01003
See application file for complete search history.

(56) References Cited

U.S. PATENT DOCUMENTS

| | | | |
|---|---|---|---|
| 2014/0255997 A1 | 9/2014 | Friis et al. | |
| 2015/0147786 A1* | 5/2015 | Clarkson | C12P 19/20 |
| | | | 127/29 |

FOREIGN PATENT DOCUMENTS

| | | |
|---|---|---|
| CN | 103946378 A | 7/2014 |
| WO | 2009121058 A1 | 10/2009 |
| WO | 2012027374 A2 | 3/2012 |
| WO | 2013148993 A1 | 10/2013 |
| WO | 2014202622 A2 | 12/2014 |
| WO | 2015065978 A1 | 5/2015 |
| WO | 2016205127 A1 | 12/2016 |

OTHER PUBLICATIONS

Grijseels et al., UniProt Database, Accession No. A0A1F5LP28, Feb. 2017.*
De Vries et al., UniProt Database, accession No. A0A1Q5U738, Apr. 2017.*
Kis-Papo et al., UniProt Database, accession No. A0A017S1Q6, Jun. 2014.*
AESCHBACHER_1999_Plant_Physiol_119_489-496, 489-496, 119.
AMARAL_1996_Can_J_Microbiol_41_1057-1062, 1057-1062, 41.
Anonymous_2015_ASM130527v1.
CARDELLO_1994_Microbiology_140_1671-1677, 1671-1677, 140.
D'ENFERT_1997_Mol_Microbiol_24_203-216, 203-216, 24.
D'ENFERT_1999_PIR_80_Database_Accession_no._T18304, 80.
DE_VRIES_2017_Uniprot_no._A0A1L9RM22.
Dewerchin 1984 J Bacteriol 158 575-579, 575-579, 158.
Fujii 2014 FEMS Microbiol Lett 351(1) 32-41, 32-41, 351(1).
FUJII_2015_EBI_Accession_no._A0A0B8MYG3.
GRBA_1975_Eur_J_Appl_Microbiol_2_29-37, 29-37, 2.
Grijseels 2016 Scientific reports 6(1) 1-13, 6(1).
GRIJSEELS_2017_EBI_Accession_no._A0A1F5LP28.
GRIJSEELS_2022_EBI_Accession_no._AOA1F5LP28.
HECKER_1973_J_Bacteriol_115_592-599, 592-599, 115.
HENEGHAN_2004_EBI_Accession_no._Q6V7X7.
Kadowaki 1996 Biochim Biophys Acta 1291 199-205, 199-205, 1291.
Li 2017 Scientific reports 7(1) 1-10, 7(1).
LI_2017_GenBank_Accession_no._CP017350.1.
Londesborough 1984 Biochem J 219 511-518, 511-518, 219.
Parvaeh 1996 FEBS Lett 391 273-278, 273-278, 391.
SUMIDA_1989_J_Ferm_Bioeng_67_83-86, 83-86, 67.
THEVELEIN_1983_J_Gen_Microbiol_129_719-726, 719-726, 129.
Waters 2011 Enzyme Microb Technol 49(2) 229-236, 229-236, 49(2).
Yang 2014 PLOS 10(10) e1004662, e1004662, 10(10).
YANG_2014_EBI_Accession_no._A0A093V3X4.
Zimmermann 1990 Biochim Biophys Acta 1036 41-46, 41-46, 1036.
WO 2014-202622 A2—EBI Accession No. BBS02793.
WO 2014-202622 A2—EBI Accession No. BBS02964.
WO 2016-205127 A1—EBI Accession No. BDL37300.
WO 2016-205127 A1—EBI Accession No. BDL37316.

* cited by examiner

*Primary Examiner* — Maryam Monshipouri
(74) *Attorney, Agent, or Firm* — David A. Fazzolare

(57) ABSTRACT

The present invention relates to polypeptides having trehalase activity, particularly derived from *Talaromyces*. The invention also relates to nucleic acid constructs, vectors, and host cells comprising the polynucleotides as well as methods of producing and using the polypeptides for the production of ethanol.

12 Claims, No Drawings

Specification includes a Sequence Listing.

PROCESSES FOR PRODUCING A FERMENTATION PRODUCT

CROSS-REFERENCE TO RELATED APPLICATIONS

This application is a divisional application of U.S. application Ser. No. 16/624,164, filed Dec. 18, 2019, now U.S. Pat. No. 11,584,783, which is a 35 U.S.C. 371 national application of international application no. PCT/US2018/039443 filed Jun. 26, 2018, which claims priority or the benefit under 35 U.S.C. 119 of U.S. provisional application No. 62/526,133 filed Jun. 28, 2017, the contents of which are fully incorporated herein by reference.

REFERENCE TO A SEQUENCE LISTING

This application contains a Sequence Listing in computer readable form. The contents of the electronic sequence listing created on Jun. 26, 2018, named 14422-WO-PCT ST25.txt and 137 KB in size, is hereby incorporated by reference in its entirety.

BACKGROUND OF THE INVENTION

Field of the Invention

The present invention relates to polypeptides having treahalase activity and polynucleotides encoding the polypeptides. The invention also relates to nucleic acid constructs, vectors, and host cells comprising the polynucleotides as well as methods of producing the polypeptides. The invention also relates to processes of producing fermentation products using a trehalase of the invention.

Description of the Related Art

Trehalose is a stable disaccharide sugar consisting of two sugar monomers (glucose). Trehalose is accumulated in yeast as a response to stress in up to 10-15% of cell dry weight (GrBa et al. (1975) Eur. J. Appl. Microbiol. 2:29-37). Trehalose cannot be metabolized by the yeast. The enzyme trehalase cleaves trehalose into two glucose units.

Trehalases are classified in EC 3.2.1.28 (alpha, alpha-trehalase) and EC. 3.2.1.93 (alpha, alpha-phosphotrehalase). The EC classes are based on recommendations of the Nomenclature Committee of the International Union of Biochemistry and Molecular Biology (IUBMB). Description of EC classes can be found on the internet, e.g., on the expasy website. The two enzyme classes are both referred to as "trehalases". Examples of neutral trehalases include trehalases from *Saccharomyces cerevisiae* (Londesborouh et al. (1984) Characterization of two trehalases from baker's yeast" Biochem J 219, 511-518; *Mucor* roxii (Dewerchin et al (1984), "Trehalase activity and cyclic AMP content during early development of *Mucor rouxii* spores", J. Bacteriol. 158, 575-579); *Phycomyces blakesleeanus* (Thevelein et al (1983), "Glucose-induced trehalase activation and trehalose mobilization during early germination of *Phycomyces blakesleeanus* spores" J. Gen Microbiol. 129, 719-726); *Fusarium* oxysporium (Amaral et al (1996), "Comparative study of two trehalase activities from *Fusarium* oxysporium var Linii" Can. J Microbiol. 41, 1057-1062). Examples of neutral trehalases include, but are not limited to, trehalases from *Saccharomyces cerevisiae* (Parvaeh et al. (1996) Purification and biochemical characterization of the ATH1 gene product, vacuolar acid trehalase from *Saccharomyces cerevisae*" FEBS Lett. 391, 273-278); Neorospora *crassa* (Hecker et al (1973), "Location of trehalase in the ascospores of *Neurospora*: Relation to ascospore dormancy and germination". J. Bacteriol. 115, 592-599); *Chaetomium aureum* (Sumida et al. (1989), "Purification and some properties of trehalase from *Chaetomium aureum* MS-27. J. Ferment. Bioeng. 67, 83-86); *Aspergillus nidulans* (d'Enfert et al. (1997), "Molecular characterization of the *Aspergillus nidulans* treA gene encoding an acid trehalase required for growth on trehalose. Mol. Microbiol. 24, 203-216); *Humicola grisea* (Zimmermann et al. (1990)." Purification and properties of an extracellular conidial trehalase from *Humicola grisea* var. thermoidea", Biochim. Acta 1036, 41-46); *Humicola grisea* (Cardello et al. (1994), "A cytosolic trehalase from the thermophilhilic fungus *Humicola grisea* var. thermoidea', Microbiology UK 140, 1671-1677; *Scytalidium thermophilum* (Kadowaki et al. (1996), "Characterization of the trehalose system from the thermophilic fungus *Scytalidium thermophilum*" Biochim. Biophys. Acta 1291, 199-205); and *Fusarium* oxysporium (Amaral et al (1996), "Comparative study of two trehalase activities from *Fusarium* oxysporium var Linii" Can. J Microbiol. 41, 1057-1062).

A trehalase is also know from soybean (Aeschbachetet al (1999)" Purification of the trehalase GmTRE1 from soybean nodules and cloning of its cDNA", Plant Physiol 119, 489-496).

Trehalases are also present in small intestine and kidney of mammals.

WO 2009/121058 (Novozymes) concerns a method of fermenting sugars derived from plant material into a fermentation product, such as ethanol, using a fermenting organism by adding one or more trehalase into in the fermentation medium.

WO 2012/027374 (Dyadic) discloses a trehalase from *Myceliophthora thermophila* which can be used in an enzyme mixture for degrading lignocellulosic biomass to fermentable sugars.

WO 2013/148993 (Novozymes) discloses a process of producing a fermentation product, such as ethanol, from starch-containing material by liquefying, saccharifying and fermenting the starch-containing material wherein a carbohydrate-source generating enzyme, a cellulolytic composition and a trehalase is present in fermentation. A trehalase from *Trichoderma reesei* is disclosed.

WO 2015/065978 (Danisco US Inc.) discloses a method of increasing the production of ethanol from a liquefact in a fermentation reaction including fermenting the liquefact with a glucoamylase, a fermenting organism and a trehalase and recovering the ethanol and other fermentation products at the end of the fermentation.

WO 2016/205127 (Novozymes) discloses a trehalase from *Myceliophthora sepedonium* belonging to Family 37 Glucoside Hydrolases ("GH37") as defined by CAZY (available online), having high thermostability and a broad pH range. It was also found that an increased ethanol yield can be obtained when adding a trehalase to fermentation in an ethanol process.

Fujii T., et al., 2014, Taxonomic revision of the cellulose-degrading fungus *Acremonium cellulolyticus* nomen *nudum* to *Talaromyces* based on phylogenetic analysis. FEMS Microbiology Letters, 351: 32-41 and Uniprot: A0A0B8MYG3 disclose trehalases from *Talaromyces* cellulyticus, and Uniprot:A0A1L9RM22 discloses a trehalase from *Aspergillus wentii*.

A trehalase from *Talaromyces verruculosus* was published in 2015 as part of a genome sequence on the NCBI website as assembly GCA 001305275.1; (polypeptide identified as EFP5BRM8N).

There is still a need for providing enzymes or enzyme composition suitable for use in processes for producing fermentation products, such as ethanol, in increased yields.

SUMMARY OF THE INVENTION

The present invention provides polypeptides having trehalase activity and polynucleotides encoding the polypeptides. The trehalases according to the invention have good stability towards degradation by proteases and high thermo-stability. The trehalases are preferably obtained from a fungus of the genus *Talaromyces*.

Accordingly, the present invention relates to polypeptides having trehalase activity selected from the group consisting of:
(a) a polypeptide having at least 93% sequence identity to the mature polypeptide of SEQ ID NO: 21 or at least 70% sequence identity to the mature polypeptide of SEQ ID NO: 23;
(b) a polypeptide encoded by a polynucleotide having at least 95% sequence identity to the mature polypeptide coding sequence of SEQ ID NO: 20 or the cDNA sequence thereof; or at least 80% sequence identity to the mature polypeptide coding sequence of SEQ ID NO: 22 or the cDNA sequence thereof;
(c) a variant of the mature polypeptide of SEQ ID NO: 21 or SEQ ID NO: 23 comprising a substitution, deletion, and/or insertion at one or more (e.g., several) positions; and
(d) a fragment of the polypeptide of (a), (b), or (c), that has trehalase activity.

In further aspect the present invention relates to polynucleotides encoding the variants; nucleic acid constructs, vectors, and host cells comprising the polynucleotides; and methods of producing the variants. In a further aspect the present invention relates to compositions comprising the variants of the invention.

The present invention also relates to a process of producing a fermentation product, comprising
(a) liquefying a starch-containing material with an alpha-amylase;
optionally pre-saccharifying the liquefied material before step (b);
(b) saccharifying the liquefied material;
(c) fermenting using a fermentation organism;
wherein
i) a glucoamylase;
ii) a trehalase of the invention;
iii) optionally a cellulolytic enzyme composition and/or a protease;
are present and/or added during
saccharification step (b);
fermentation step (c);
simultaneous saccharification and fermentation;
optionally presaccharification step before step (b).

In still further aspects the present invention relates to process of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase, alpha-amylase, trehalase of any of claims 1-7, and optionally a protease and/or a cellulolytic enzyme composition.

Definitions

Trehalase: The term "trehalase" means an enzyme which degrades trehalose into its unit monosaccharides (i.e., glucose). Trehalases are classified in EC 3.2.1.28 (alpha,alpha-trehalase) and EC. 3.2.1.93 (alpha,alpha-phosphotrehalase). The EC classes are based on recommendations of the Nomenclature Committee of the International Union of Biochemistry and Molecular Biology (IUBMB). Description of EC classes can be found on the internet, e.g., on the expasy website. Trehalases are enzymes that catalyze the following reactions:
EC 3.2.1.28:
Alpha,alpha-trehalose+$H_2O$⇔2 D-glucose;
EC 3.2.1. 93:
Alpha,alpha-trehalose 6-phosphate+$H_2O$⇔D-glucose+ D-glucose 6-phosphate.

For purposes of the present invention, trehalase activity may be determined according to "Trehalase Assay" procedure described in the "Materials & Methods"-section. In one aspect, the polypeptides of the present invention have at least 20%, e.g., at least 40%, at least 50%, at least 60%, at least 70%, at least 80%, at least 90%, at least 95%, or at least 100% of the trehalase activity of the mature polypeptide of SEQ ID NO: 21. In another aspect, the polypeptides of the present invention have at least 20%, e.g., at least 40%, at least 50%, at least 60%, at least 70%, at least 80%, at least 90%, at least 95%, or at least 100% of the trehalase activity of the mature polypeptide of SEQ ID NO: 23. In a preferred embodiment a trehalase of the invention is a Family 65 Glycoside Hydrolase ("GH65 trehalase").

In one embodiment the trehalases according to the invention, SEQ ID NO: 21 and/or SEQ ID NO: 23 have a denaturing temperature Td (measured by the TSA assay) of at least 60° C., at least 61° C., at least 62° C., at least 63° C., at least 64° C., at least 65° C., at least 66° C., at least 67° C., such as at least 68° C.

In another embodiment the trehalases according to the invention, SEQ ID NO: 21 and/or SEQ ID NO: 23 have a residual activity after 3 days incubation at 40° C. with an *A. niger* protease mixture of 100%.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme. In one embodiment the catalytic domain is amino acids 387 to 769 of SEQ ID NO: 21. In another embodiment the catalytic domain is amino acids 384 to 799 of SEQ ID NO: 23. cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a mature polypeptide; wherein the fragment has trehalase activity. In one aspect, a fragment contains amino acids 387 to 769 of SEQ ID NO: 21. In one aspect, a fragment contains at least amino acids 384 to 799 of SEQ ID NO: 23.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to thermostability, wherein the denaturing temperature (Td) measure by Thermal Shift Assay (TSA) is at least 60° C., at least 61° C., at least 62° C., at least 63° C., at least 64° C., at least 65° C., at least 66° C., at least 67° C., such as at least 68° C. and stability against protease degradation, in particular degradation by *Aspergillus niger* protease mixture.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 19 to 1038 of SEQ ID NO: 21. In another aspect, the mature polypeptide is amino acids 21 to 1089 of SEQ ID NO: 23. It is known in the art that a host cell may produce a mixture of two of more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having trehalase activity. In one aspect, the mature polypeptide coding sequence is nucleotides 55 to 2037, and 2085 to 3161 of SEQ ID NO: 20. Nucleotides 1 to 54 of SEQ ID NO: 20 encode a signal peptide. In another aspect, the mature polypeptide coding sequence is nucleotides 61 to 1740, and 2026 to 2313, and 2367 to 3605 of SEQ ID NO: 22. Nucleotides 1 to 60 of SEQ ID NO: 22 encode a signal peptide.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences. In one embodiment the one or more control sequences are heterologous (of different origin/species) to the coding sequence encoding the polypeptide of the invention.

Operably linked: The term "operably linked" means a configuration in which a control sequence is placed at an appropriate position relative to the coding sequence of a polynucleotide such that the control sequence directs expression of the coding sequence.

Parent or parent trehalase: The term "parent" or "parent trehalase" means any polypeptide with trehalase activity to which an alteration is made to produce an enzyme variants of the present invention.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62

(EMBOSS version of BLOSUM62) substitution matrix. The output of Needle labeled "longest identity" (obtained using the —nobrief option) is used as the percent identity and is calculated as follows:

(Identical Residues×100)/(Length of Alignment−
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the —nobrief option) is used as the percent identity and is calculated as follows:

(Identical Deoxyribonucleotides×100)/(Length of
Alignment−Total Number of Gaps in Alignment)

Stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having trehalase activity. In one aspect, a subsequence contains at least nucleotides 1159 to 2037, and 2085 to 2354 of SEQ ID NO: 20. In one aspect, a subsequence contains at least nucleotides 1150 to 1740, and 2026 to 2313, and 2367 to 2735 of SEQ ID NO: 22.

Variant: The term "variant" means a polypeptide having trehalase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position The variants of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 21. The variants of the present invention have at least 20%, e.g., at least 40%, at least 50%, at least 60%, at least 70%, at least 80%, at least 90%, at least 95%, or at least 100% of the trehalase activity of the polypeptide of SEQ ID NO: 23.

Wild-type trehalase: The term "wild-type" trehalase means a trehalase expressed by a naturally occurring microorganism, such as a bacterium, yeast, or filamentous fungus found in nature.

DETAILED DESCRIPTION OF THE INVENTION

Polypeptides Having Trehalse Activity

In an embodiment, the present invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 21.

In a particular embodiment the invention relates to polypeptides having a sequence identity to the mature polypeptide of SEQ ID NO: 21 of at least 80%, at least 85%, at least 90%, at least 91%, at least 92%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the trehalase activity of the mature polypeptide of SEQ ID NO: 21, and wherein the denaturing temperature measured by TSA is at least 60° C.

In a particular embodiment the invention relates to polypeptides having a sequence identity to the mature polypeptide of SEQ ID NO: 21 of at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the trehalase activity of the mature polypeptide of SEQ ID NO: 21, and wherein the denaturing temperature measured by TSA is at least 60° C.

In an embodiment, the present invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have trehalase activity. In one aspect, the polypeptides differ by up to 10 amino acids, e.g., 1, 2, 3, 4, 5, 6, 7, 8, 9, or 10, from the mature polypeptide of SEQ ID NO: 23.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, least 91%, at least 92%, at least 93%, at least 94%, at least 95%, at least 96%, at least 97%, at least 98%, at least 99%, or 100%, and wherein the polypeptide has at least at least 75% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, 91%, at least 92%, at least 93%, at least 94%, at least 95%, at least 96%, at least 97%, at least 98%, at least 99%, or 100%, and wherein the polypeptide has at least at least 95% of the trehalase activity of the mature polypeptide of SEQ ID NO: 23, and wherein the denaturing temperature measured by TSA is at least 60° C.

In a particular embodiment the invention relates to polypeptides having a sequence identity to the mature polypeptide of SEQ ID NO: 23 of at least 70%, at least 75%, at least 80%, at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the trehalase activity of the mature polypeptide of SEQ ID NO: 23, and wherein the denaturing temperature measured by TSA is at least 60° C.

In an embodiment, the polypeptide has been isolated. A polypeptide of the present invention preferably comprises or consists of the amino acid sequence of SEQ ID NO: 21 or an allelic variant thereof; or is a fragment thereof having trehalase activity. In another aspect, the polypeptide comprises or consists of the mature polypeptide of SEQ ID NO: 21. In another aspect, the polypeptide comprises or consists of amino acids 19 to 1038 of SEQ ID NO: 21.

In an embodiment, the polypeptide has been isolated. A polypeptide of the present invention preferably comprises or consists of the amino acid sequence of SEQ ID NO: 23 or an allelic variant thereof; or is a fragment thereof having trehalase activity. In another aspect, the polypeptide comprises or consists of the mature polypeptide of SEQ ID NO: 23. In another aspect, the polypeptide comprises or consists of amino acids 21 to 1089 of SEQ ID NO: 23.

In another embodiment, the present invention relates to a polypeptide having trehalase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 20, (ii) the cDNA sequence thereof, or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

In another embodiment, the present invention relates to a polypeptide having trehalase activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 22, (ii) the cDNA sequence thereof, or (iii) the full-length complement of (i) or (ii) (Sambrook et al., 1989, *Molecular Cloning, A Laboratory Manual*, 2d edition, Cold Spring Harbor, New York). In an embodiment, the polypeptide has been isolated.

The polynucleotide of SEQ ID NO: 20 or SEQ ID NO: 22 or a subsequence thereof, as well as the polypeptide of SEQ ID NO: 21 or SEQ ID NO: 23 or a fragments thereof may be used to design nucleic acid probes to identify and clone DNA encoding polypeptides having trehalase activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having trehalase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 20 or 22; (ii) the mature polypeptide coding sequence of SEQ ID NO: 20 or 22; (iii) the cDNA sequence thereof; (iv) the full-length complement thereof; or (v) a subsequence thereof; under very low to very high stringency conditions. Molecules to which the nucleic acid probe hybridizes under these conditions can be detected using, for example, X-ray film or any other detection means known in the art.

In another embodiment, the present invention relates to an polypeptide having trehalase activity encoded by a polynucleotide having a sequence identity to the mature polypeptide coding sequence of SEQ ID NO: 20 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to an polypeptide having trehalase activity encoded by a polynucleotide having a sequence identity to the mature polypeptide coding sequence of SEQ ID NO: 22 or the cDNA sequence thereof of at least 80%, at least 85%, at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the mature polypeptide of SEQ ID NO: 21 comprising a substitution, deletion, and/or insertion at one or more (e.g., several) positions. In an embodiment, the number of amino acid substitutions, deletions and/or insertions introduced into the mature polypeptide of SEQ ID NO: 21 is up to 10, e.g., 1, 2, 3, 4, 5, 6, 7, 8, 9, or 10.

In another embodiment, the present invention relates to variants of the mature polypeptide of SEQ ID NO: 23 comprising a substitution, deletion, and/or insertion at one or more (e.g., several) positions. In an embodiment, the number of amino acid substitutions, deletions and/or insertions introduced into the mature polypeptide of SEQ ID NO: 23 is up to 10, e.g., 1, 2, 3, 4, 5, 6, 7, 8, 9, or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for trehalase activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Sources of Polypeptides Having trehalase Activity

A polypeptide having trehalase activity of the present invention may be obtained from microorganisms of genus *Talaromyces*. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

In one aspect, the polypeptide is a *Talaromyces* polypeptide, e.g., a polypeptide obtained from *Talaromyces funiculosus* or from *Talaromyces leycettanus*, such as e.g., CBS 398.68.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Catalytic Domains

In one embodiment, the present invention also relates to catalytic domains having a sequence identity to amino acids 387 to 769 of SEQ ID NO: 21 of at least at least 80%, at least 85%, at least 90, at least 92%, at least 93%, at least 94%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 387 to 769 of SEQ ID NO: 21.

The catalytic domain preferably comprises or consists of amino acids 387 to 769 of SEQ ID NO: 21; or is a fragment thereof having trehalase activity.

In another embodiment, the present invention also relates to catalytic domains encoded by polynucleotides having a sequence identity to nucleotides 1159 to 2037, and 2085 to 2354 of SEQ ID NO: 20 or the cDNA sequence thereof of at least 80%, at least 85%, at least 90, at least 92%, at least 93%, at least 94%, at least 95%, at least 96%, at least 97%, at least 98%, at least 99%, or 100%.

The polynucleotide encoding the catalytic domain preferably comprises or consists of nucleotides 1159 to 2037, and 2085 to 2354 of SEQ ID NO: 20.

In another embodiment, the present invention also relates to catalytic domain variants of amino acids 387 to 769 of SEQ ID NO: 21 comprising a substitution, deletion, and/or insertion at one or more (e.g., several) positions. In one aspect, the number of amino acid substitutions, deletions and/or insertions introduced into the sequence of amino acids 387 to 769 of SEQ ID NO: 21 is up to 10, e.g., 1, 2, 3, 4, 5, 6, 8, 9, or 10.

In one embodiment, the present invention also relates to catalytic domains having a sequence identity to amino acids 384 to 799 of SEQ ID NO: 23 of at least 75%, at least 80%, at least 85%, at least 90, at least at least 93%, at least 95%, at least 96%, at least 97%, at least 98%, at least 99%, or 100%. In one aspect, the catalytic domains comprise amino acid sequences that differ by up to 10 amino acids, e.g., 1, 2, 3, 4, 5, 6, 7, 8, 9, or 10, from amino acids 384 to 799 of SEQ ID NO: 23.

The catalytic domain preferably comprises or consists of amino acids 384 to 799 of SEQ ID NO: 23 or an allelic variant thereof; or is a fragment thereof having trehalase activity.

In another embodiment, the present invention also relates to catalytic domains encoded by polynucleotides having a sequence identity to nucleotides 1150 to 1740, and 2026 to 2313, and 2367 to 2735 of SEQ ID NO: 22 or the cDNA sequence thereof of at least 75%, at least 80%, at least 85%, at least 90, at least 93%, at least 95%, at least 96%, at least 97%, at least 98%, at least 99%, or 100%.

The polynucleotide encoding the catalytic domain preferably comprises or consists of nucleotides 1150 to 1740, and 2026 to 2313, and 2367 to 2735 of SEQ ID NO: 22.

In another embodiment, the present invention also relates to catalytic domain variants of amino acids 384 to 799 of SEQ ID NO: 23 comprising a substitution, deletion, and/or insertion at one or more (e.g., several) positions. In one aspect, the number of amino acid substitutions, deletions and/or insertions introduced into the sequence of amino acids 384 to 799 of SEQ ID NO: 23 is up to 10, e.g., 1, 2, 3, 4, 5, 6, 8, 9, or 10.

Polynucleotides

The present invention also relates to polynucleotides encoding a polypeptide, or a catalytic domain of the present invention, as described herein. In an embodiment, the polynucleotide encoding the polypeptide, or catalytic domain, of the present invention has been isolated.

The techniques used to isolate or clone a polynucleotide are known in the art and include isolation from genomic DNA or cDNA, or a combination thereof. The cloning of the polynucleotides from genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Talaromyces*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. In one particular embodiment at least one control sequence is heterologous (of different origin/species) to the polynucleotide encoding the variant of the present invention.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase,

*Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase,

*Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used.

Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. In a particular embodiment the recombinant host cell comprises the polynucleotide encoding a trehalase polypeptide of the present invention in which the said polynucleotide is heterologous (of different origin/species) to the host cell. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, Ainsworth and Bisby's Dictionary of The Fungi, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, Soc. App. Bacteriol. Symposium Series No. 9, 1980).

The yeast host cell may be a Candida, Hansenula, Kluyveromyces, Pichia, Saccharomyces, Schizosaccharomyces, or Yarrowia cell, such as a Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis, or Yarrowia lipolytica cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as Saccharomyces cerevisiae is by budding of a unicellular thallus and carbon catabolism may be fermentative.

The filamentous fungal host cell may be an Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes, or Trichoderma cell.

For example, the filamentous fungal host cell may be an Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus etyngii, Thielavia terrestris, Trametes villosa, Trametes versicolor, Trichoderma harzianum, Trichoderma koningii, Trichoderma longibrachiatum, Trichoderma reesei, or Trichoderma viride cell.

Fungal cells may be transformed by a process involving protoplast formation, transformation of the protoplasts, and regeneration of the cell wall in a manner known per se. Suitable procedures for transformation of Aspergillus and Trichoderma host cells are described in EP 238023, Yelton et al., 1984, Proc. Natl. Acad. Sci. USA 81: 1470-1474, and Christensen et al., 1988, Bio/Technology 6: 1419-1422. Suitable methods for transforming Fusarium species are described by Malardier et al., 1989, Gene 78: 147-156, and WO 96/00787. Yeast may be transformed using the procedures described by Becker and Guarente, In Abelson, J. N. and Simon, M. I., editors, Guide to Yeast Genetics and Molecular Biology, Methods in Enzymology, Volume 194, pp 182-187, Academic Press, Inc., New York; Ito et al., 1983, J. Bacteriol. 153: 163; and Hinnen et al., 1978, Proc. Natl. Acad. Sci. USA 75: 1920.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Fermentation Broth Formulations or Cell Compositions

The present invention also relates to a fermentation broth formulation or a cell composition comprising a polypeptide of the present invention. In a particular embodiment the whole broth formulation is generated by fermentation of a recombinant host cell of the invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

The present invention also relates to compositions comprising a polypeptide having trehalase activity of the present invention. Preferably, the compositions are enriched in such a polypeptide. The term "enriched" indicates that the trehalase activity of the composition has been increased, e.g., with an enrichment factor of at least 1.1.

The compositions may comprise a polypeptide of the present invention as the major enzymatic component, e.g., a mono-component composition. Alternatively, the compositions may comprise multiple enzymatic activities, such as one or more (e.g., several) enzymes selected from the group consisting of hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase.

In an embodiment the composition comprises a trehalase of the invention and a glucoamylase. In an embodiment the composition comprises a trehalase of the invention and a glucoamylase derived from *Talaromyces emersonii* (e.g., SEQ ID NO: 4). In an embodiment the composition comprises a trehalase of the invention and a glucoamylase derived from *Gloeophyllum*, such as *G. serpiarium* (e.g., SEQ ID NO: 5) or *G. trabeum* (e.g., SEQ ID NO: 6). In an embodiment the composition comprises a trehalase of the invention, a glucoamylase and an alpha-amylase. In an embodiment the composition comprises a trehalase of the invention, a glucoamylase and an alpha-amylase derived from *Rhizomucor*, preferably a strain the *Rhizomucor pusillus*, such as a *Rhizomucor pusillus* alpha-amylase hybrid having an linker (e.g., from *Aspergillus niger*) and starch-bonding domain (e.g., from *Aspergillus niger*). In an embodiment the composition comprises a trehalase of the invention, a glucoamylase, an alpha-amylase and a cellulolytic enzyme composition. In an embodiment the composition comprises a trehalase of the invention, a glucoamylase, an alpha-amylase and a cellulolytic enzyme composition, wherein the cellulolytic composition is derived from *Trichoderma reesei*. In an embodiment the composition comprises a trehalase of the invention, a glucoamylase, an alpha-amylase and a protease. In an embodiment the composition comprises a trehalase of the invention, a glucoamylase, an alpha-amylase and a protease. The protease may be derived from *Thermoascus aurantiacus*. In an embodiment the composition comprises a trehalase of the invention, a glucoamylase, an alpha-amylase, a cellulolytic enzyme composition and a protease. In an embodiment the composition comprises a trehalase of the invention, a glucoamylase, e.g., derived from *Talaromyces emersonii*, *Gloeophyllum serpiarium* or *Gloephyllum trabeum*, an alpha-amylase, e.g., derived from *Rhizomucor pusillus*, in particular one having a linker and starch-binding domain, in particular derived from *Aspergillus niger*, in particular one having the following substitutions: G128D+D143N (using SEQ ID NO: 7 for numbering); a cellulolytic enzyme composition derived from *Trichoderma reesei*, and a protease, e.g., derived from *Thermoascus aurantiacus* or *Meripilus giganteus*.

Examples of specifically contemplated secondary enzymes, e.g., a glucoamylase from *Talaromyces emersonii* shown in SEQ ID NO: 4 herein or a glucoamylase having, e.g., at least 60%, at least 70%, at least 80%, at least 90%, at least 95%, at least 96%, at least 97%, at least 98%, at least 99% identity to SEQ ID NO: 4 herein can be found in the "Enzymes" section below.

The compositions may be prepared in accordance with methods known in the art and may be in the form of a liquid or a dry composition. The compositions may be stabilized in accordance with methods known in the art.

Examples are given below of preferred uses of the compositions of the present invention. The dosage of the composition and other conditions under which the composition is used may be determined on the basis of methods known in the art.

Uses
Processes of the Invention
Producing a Fermentation Product from Gelatinized Starch Material Using a Trehalase of the Invention In this aspect the present invention relates to producing a fermentation product, in particular ethanol, from gelatinized and/or ungelatinized starch-containing material or cellulosic material. Fermentable sugars generated during saccharification/hydrolysis are converted to the desired fermentation in question, in particular ethanol, during fermentation by a fermenting organism, in particular yeast.

In an embodiment the invention relates to processes of producing a fermentation product, in particular ethanol, comprising
(a) liquefying a starch-containing material with an alpha-amylase; optionally pre-saccharifying the liquefied material before step (b);
(b) saccharifying the liquefied material;
(c) fermenting using a fermentation organism;
wherein
i) a glucoamylase;
ii) a trehalase of the invention;
iii) optionally a cellulolytic enzyme composition and/or a protease;
are present and/or added during
saccharification step (b);
fermentation step (c);
simultaneous saccharification and fermentation;
optionally presaccharification step before step (b).

Liquefaction Step (a)
According to processes of the invention, liquefaction in step (a) is carried out by subjecting starch-containing material at a temperature above the initial gelatinization temperature, in particular at a temperature between 80-90° C., to an alpha-amylase and optionally a protease and other enzymes, such as a glucoamylase, a pullulanase and/or a phytase.

The term "initial gelatinization temperature" means the lowest temperature at which gelatinization of the starch-containing material commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Starke* 44(12): 461-466.

According to the invention liquefaction in step (a) is typically carried out at a temperature in the range from 70-100° C. In an embodiment the temperature in liquefaction is between 75-95° C., such as between 75-90° C., preferably between 80-90° C., such as 82-88° C., such as around 85° C.

The pH in liquefaction may be in the range between 3 and 7, preferably from 4 to 6, or more preferably from 4.5 to 5.5.

According to the invention a jet-cooking step may be carried out prior to liquefaction in step (a). The jet-cooking may be carried out at a temperature between 110-145° C., preferably 120-140° C., such as 125-135° C., preferably around 130° C. for about 1-15 minutes, preferably for about 3-10 minutes, especially around about 5 minutes.

In an embodiment, the process of the invention further comprises, prior to the liquefaction step (a), the steps of:
x) reducing the particle size of the starch-containing material, preferably by dry milling;
z) forming a slurry comprising the starch-containing material and water.

According to the invention the dry solid content (DS) in liquefaction lies in the range from 20-55 wt.-%, preferably 25-45 wt.-%, more preferably 30-40 wt.-% or 30-45 wt-%.

The starch-containing starting material, such as whole grains, may be reduced in particle size, e.g., by milling, in order to open up the structure, to increase surface area, and allowing for further processing. Generally there are two types of processes: wet and dry milling. In dry milling whole kernels are milled and used. Wet milling gives a good separation of germ and meal (starch granules and protein). Wet milling is often applied at locations where the starch hydrolysate is used in production of, e.g., syrups. Both dry milling and wet milling are well known in the art of starch processing. According to the present invention dry milling is preferred.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In another embodiment at least 50%, preferably at least 70%, more preferably at least 80%, especially at least 90% of the starch-containing material fit through a sieve with #6 screen.

Liquefaction in step (a) may be carried out for 0.5-5 hours, such as 1-3 hours, such as typically around 2 hours.

The alpha-amylase and other optional enzymes, such as protease, may initially be added to the aqueous slurry to initiate liquefaction (thinning). In an embodiment only a portion of the enzymes (e.g., about ⅓) is added to the aqueous slurry, while the rest of the enzymes (e.g., about ⅔) are added in liquefaction step (a).

A non-exhaustive list of examples of alpha-amylases can be found below in the "Alpha-Amylase Present and/or Added In Liquefaction"-section. In a preferred embodiment the alpha-amylase is a bacterial alpha-amylase. Bacterial alpha-amylases are typically thermostable. In a preferred embodiment the alpha-amylase is derived from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 8 herein.

In an embodiment the alpha-amylase used in liquefaction step (a) is a variant of the *Bacillus stearothermophilus* alpha-amylase shown in SEQ ID NO: 8 herein, in particular with the double deletions in I181*+G182*, and optionally with a N193F substitution, and truncated to be around 491 amino acids long, e.g., from 480-495 amino acids long.

Examples of suitable *Bacillus stearothermophilus* alpha-amylase variants can be found below in the "Thermostable Alpha-Amylase"-section and include one from the following group of *Bacillus stearothermophilus* alpha-amylase variants with double deletions I181*+G182*, and optionally substitution N193F, and additionally the following substitutions:

E129V+K177L+R179E;
V59A+Q89R+E129V+K177L+R179E+H208Y+K220P+ N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S (using SEQ ID NO: 8 for numbering).

According to processes of the invention, liquefaction in step (a) may be carried out using a combination of alpha-amylase (e.g., *Bacillus stearothermophilus* alpha-amylase shown in SEQ ID NO: 8) and protease (e.g., *Pyrococcus furiosus* (pfu protease) shown in SEQ ID NO: 9). A glucoamylase may also be present, such as the one derived from *Penicillium oxalicum* shown in SEQ ID NO: 10 herein (see the "Glucoamylase Present and/or Added In Liquefaction Step (a)"—section below.

Saccharification and Fermentation

A trehalase of the invention, a glucoamylase and optionally a protease and/or a cellulolytic enzyme composition may be present and/or added in saccharification step (b); fermentation step (c); simultaneous saccharification and fermentation (SSF); optionally a presaccharification step before step (b).

In a preferred embodiment the glucoamylase is added together with a fungal alpha-amylase, in particular acid fungal alpha-amylase. Examples of glucoamylases can be found in the "Glucoamylases Present and/or Added In Saccharification and/or Fermentation"-section below.

When doing sequential saccharification and fermentation, saccharification step (b) may be carried out at conditions well-known in the art, i.e., suitable for enzyme saccharification. For instance, the saccharification step (b) may last up to from about 24 to about 72 hours.

In an embodiment pre-saccharification is done before saccharification in step (b). Pre-saccharification is typically done for 40-90 minutes at a temperature between 30-65° C., typically about 60° C. Pre-saccharification is in an embodiment followed by saccharification during fermentation in simultaneous saccharification and fermentation (SSF). Saccharification is typically carried out at temperatures from 20-75° C., preferably from 40-70° C., typically around 60° C., and at a pH between 4 and 5, normally at about pH 4.5.

Simultaneous saccharification and fermentation ("SSF") is widely used in industrial scale fermentation product production processes, especially ethanol production processes. When doing SSF the saccharification step (b) and the fermentation step (c) are carried out simultaneously. There is no holding stage for the saccharification, meaning that a fermenting organism, in particular yeast, and enzymes, may be added together. However, it is also contemplated to add the fermenting organism and enzymes separately. SSF is according to the invention typically carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours. In an embodiment the pH is between 4-5.

In an embodiment of the invention a cellulolytic composition is present and/or added in saccharification step (b), fermentation step (c) or simultaneous saccharification and fermentation (SSF) or pre-saccharification before step (b). Examples of such cellulolytic compositions can be found in the "Cellulolytic Enzyme Composition present and/or added during Saccharification and/or Fermentation"-section below. The optional cellulolytic enzyme composition may be present and/or added together with the glucoamylase and trehalase of the invention. Examples of proteases can be found in the "Proteases Present and/or Added In Saccharification and/or Fermentation"-section below.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

Starch-Containing Materials

According to the invention any suitable starch-containing starting material may be used. The starting material is generally selected based on the desired fermentation product, in particular ethanol. Examples of starch-containing starting materials, suitable for use in processes of the present invention, include cereal, tubers or grains. Specifically the starch-containing material may be corn, wheat, barley, rye, milo, sago, cassava, tapioca, sorghum, oat, rice, peas, beans, or sweet potatoes, or mixtures thereof. Contemplated are also waxy and non-waxy types of corn and barley.

In a preferred embodiment the starch-containing starting material is corn.

In a preferred embodiment the starch-containing starting material is wheat.

In a preferred embodiment the starch-containing starting material is barley.

In a preferred embodiment the starch-containing starting material is rye.

In a preferred embodiment the starch-containing starting material is milo.

In a preferred embodiment the starch-containing starting material is sago.

In a preferred embodiment the starch-containing starting material is cassava.

In a preferred embodiment the starch-containing starting material is tapioca.

In a preferred embodiment the starch-containing starting material is sorghum.

In a preferred embodiment the starch-containing starting material is rice,

In a preferred embodiment the starch-containing starting material is peas.

In a preferred embodiment the starch-containing starting material is beans.

In a preferred embodiment the starch-containing starting material is sweet potatoes.

In a preferred embodiment the starch-containing starting material is oats.

Producing a Fermentation Product from Ungelatinized Starch Material Using a Trehalase of the Invention A trehalase of the invention may suitably be used in a raw starch hydrolysis (RSH) process for producing desired fermentation products, in particular ethanol. In RSH processes the starch does not gelatinize as the process is carried out at temperatures below the initial gelatinization temperature of the starch in question (defined above).

The desired fermentation product may in an embodiment be ethanol produced from un-gelatinized (i.e., uncooked), preferably milled, grains, such as corn, or small grains such as wheat, oats, barley, rye, rice, or cereals such as sorghum. Examples of suitable starch-containing starting materials are listed in the section "Starch-Containing Materials"-section above.

Accordingly, in this aspect the invention relates to processes of producing fermentation products from starch-containing material comprising:
(a) saccharifying a starch-containing material at a temperature below the initial gelatinization temperature; and
(b) fermenting using a fermentation organism; and
(c) optionally recovering the fermentation product;
wherein saccharification and/or fermentation is done in the presence of the following enzymes: glucoamylase, alpha-amylase, trehalase of the invention, and optionally a cellulolytic enzyme composition and/or a protease.

Before step (a) an aqueous slurry of starch-containing material, such as granular starch, having 10-55 wt.-% dry solids (DS), preferably 25-45 wt.-% dry solids, more preferably 30-40% dry solids of starch-containing material may be prepared. The slurry may include water and/or process waters, such as stillage (backset), scrubber water, evaporator condensate or distillate, side-stripper water from distillation, or process water from other fermentation product plants. Because a raw starch hydrolysis process of the invention is carried out below the initial gelatinization temperature, and thus no significant viscosity increase takes place, high levels of stillage may be used, if desired. In an embodiment the aqueous slurry contains from about 1 to about 70 vol.-%, preferably 15-60% vol.-%, especially from about 30 to 50 vol.-% water and/or process waters, such as stillage (backset), scrubber water, evaporator condensate or distillate, side-stripper water from distillation, or process water from other fermentation product plants, or combinations thereof, or the like.

In an embodiment backset, or another recycled stream, is added to the slurry before step (a), or to the saccharification (step (a)), or to the simultaneous saccharification and fermentation steps (combined step (a) and step (b)).

A RSH process of the invention is conducted at a temperature below the initial gelatinization temperature, which means that the temperature at which a separate step (a) is carried out typically lies in the range between 25-75° C., such as between 30-70° C., or between 45-60° C.

In a preferred embodiment the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

In an embodiment of the invention fermentation is carried out for 30 to 150 hours, preferably 48 to 96 hours. 66.

In an embodiment fermentation is carried out so that the sugar level, such as glucose level, is kept at a low level, such as below 6 wt.-%, such as below about 3 wt.-%, such as below about 2 wt.-%, such as below about 1 wt.-%., such as below about 0.5%, or below 0.25% wt.-%, such as below about 0.1 wt.-%. Such low levels of sugar can be accomplished by simply employing adjusted quantities of enzymes and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 wt.-%, such as below about 0.2 wt.-%.

The process of the invention may be carried out at a pH from 3 and 7, preferably from 3 to 6, or more preferably from 3.5 to 5.0.

The term "granular starch" means raw uncooked starch, i.e., starch in its natural form found in, e.g., cereal, tubers or grains. Starch is formed within plant cells as tiny granules insoluble in water. When put in cold water, the starch granules may absorb a small amount of the liquid and swell. At temperatures up to around 50° C. to 75° C. the swelling may be reversible. However, at higher temperatures an irreversible swelling called "gelatinization" begins. The granular starch may be a highly refined starch, preferably at least 90%, at least 95%, at least 97% or at least 99.5% pure, or it may be a more crude starch-containing materials comprising (e.g., milled) whole grains including non-starch fractions such as germ residues and fibers.

The raw material, such as whole grains, may be reduced in particle size, e.g., by milling, in order to open up the structure and allowing for further processing. Examples of suitable particle sizes are disclosed in U.S. Pat. No. 4,514,496 and WO2004/081193 (both references are incorporated by reference). Two processes are preferred according to the invention: wet and dry milling. In dry milling whole kernels are milled and used. Wet milling gives a good separation of germ and meal (starch granules and protein) and is often applied at locations where the starch hydrolysate is used in production of, e.g., syrups. Both dry and wet milling is well known in the art of starch processing.

In an embodiment the particle size is reduced to between 0.05 to 3.0 mm, preferably 0.1-0.5 mm, or so that at least 30%, preferably at least 50%, more preferably at least 70%, even more preferably at least 90% of the starch-containing material fit through a sieve with a 0.05 to 3.0 mm screen, preferably 0.1-0.5 mm screen. In a preferred embodiment starch-containing material is prepared by reducing the particle size of the starch-containing material, preferably by milling, such that at least 50% of the starch-containing material has a particle size of 0.1-0.5 mm.

In a preferred embodiment the trehalase is present and/or added in an amount between 0.01-20 ug EP trehalase/g DS, such as between 0.05-15 ug EP terhalase/g DS, such as between 0.5 and 10 ug EP trehalase/g DS.

According to the invention the enzymes are added so that the glucoamylase is present in an amount of 0.001 to 10 AGU/g DS, preferably from 0.01 to 5 AGU/g DS, especially 0.1 to 0.5 AGU/g DS.

According to the invention the enzymes are added so that the alpha-amylase is present or added in an amount of 0.001 to 10 AFAU/g DS, preferably from 0.01 to 5 AFAU/g DS, especially 0.3 to 2 AFAU/g DS or 0.001 to 1 FAU-F/g DS, preferably 0.01 to 1 FAU-F/g DS.

According to the invention the enzymes are added so that the cellulolytic enzyme composition is present or added in an amount 1-10,000 micro grams EP/g DS, such as 2-5,000, such as 3 and 1,000, such as 4 and 500 micro grams EP/g DS.

According to the invention the enzymes are added so that the cellulolytic enzyme composition is present or added in an amount in the range from 0.1-100 FPU per gram total solids (TS), preferably 0.5-50 FPU per gram TS, especially 1-20 FPU per gram TS.

In an embodiment of the invention the enzymes are added so that the protease is present in an amount of 0.0001-1 mg enzyme protein per g DS, preferably 0.001 to 0.1 mg enzyme protein per g DS. Alternatively, the protease is present and/or added in an amount of 0.0001 to 1 LAPU/g DS, preferably 0.001 to 0.1 LAPU/g DS and/or 0.0001 to 1 mAU-RH/g DS, preferably 0.001 to 0.1 mAU-RH/g DS.

In an embodiment of the invention the enzymes are added so that the protease is present or added in an amount in the range 1-1,000 µg EP/g DS, such as 2-500 µg EP/g DS, such as 3-250 µg EP/g DS.

In a preferred embodiment ratio between glucoamylase and alpha-amylase is between 99:1 and 1:2, such as between 98:2 and 1:1, such as between 97:3 and 2:1, such as between 96:4 and 3:1, such as 97:3, 96:4, 95:5, 94:6, 93:7, 90:10, 85:15, 83:17 or 65:35 (mg EP glucoamylase: mg EP alpha-amylase).

In a preferred embodiment the total dose of glucoamylase and alpha-amylase is according to the invention from 10-1,000 µg/g DS, such as from 50-500 µg/g DS, such as 75-250 µg/g DS.

In a preferred embodiment the total dose of cellulolytic enzyme composition added is from 10-500 µg/g DS, such as from 20-400 µg/g DS, such as 20-300 µg/g DS.

In an embodiment the glucoamylase, such as one derived from *Trametes cingulata*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 11.

In an embodiment the glucoamylase, such as one derived from *Pycnoporus sanguineus*, used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12.

In an embodiment the alpha-amylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 7.

In a preferred embodiment the invention relates to processes of producing fermentation products from starch-containing material comprising:
(a) saccharifying a starch-containing material at a temperature below the initial gelatinization temperature; and
(b) fermenting using a fermentation organism;
wherein saccharification and/or fermentation is done in the presence of the following enzymes:
i) glucoamylase;
ii) alpha-amylase;
iii) trehalse of the invention;
iii) optionally a cellulolytic enzyme composition and/or a protease.

In a preferred embodiment the enzymes may be added as an enzyme composition of the invention. In a preferred embodiment steps (a) and (b) are carried out simultaneously (i.e., one-step fermentation). However, step (a) and (b) may also be carried our sequentially.

Fermentation

Fermentation is carried out in a fermentation medium. The fermentation medium includes the fermentation substrate, that is, the carbohydrate source that is metabolized by the fermenting organism. According to the invention the fermentation medium may comprise nutrients and growth stimulator(s) for the fermenting organism(s). Nutrient and growth stimulators are widely used in the art of fermentation and include nitrogen sources, such as ammonia; urea, vitamins and minerals, or combinations thereof.

Fermenting Organisms for Starch Based Fermentation

The term "fermenting organism" refers to any organism, including bacterial and fungal organisms, especially yeast, suitable for use in a fermentation process and capable of producing the desired fermentation product. Especially suitable fermenting organisms are able to ferment, i.e., convert, sugars, such as glucose or maltose, directly or indirectly into the desired fermentation product, such as in particular ethanol. Examples of fermenting organisms include fungal organisms, such as in particular yeast. Preferred yeast includes strains of *Saccharomyces* spp., in particular, *Saccharomyces cerevisiae*. In a particular embodiment the *S. cerevisiae* expresses the trehalase of the invention.

Suitable concentrations of the viable fermenting organism during fermentation, such as SSF, are well known in the art or can easily be determined by the skilled person in the art. In one embodiment the fermenting organism, such as ethanol fermenting yeast, (e.g., *Saccharomyces cerevisiae*) is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Examples of commercially available yeast includes, e.g., RED START™ and ETHANOL RED™ yeast (available from Fermentis/Lesaffre, USA), FALI (available from Fleischmann's Yeast, USA), SUPERSTART and THERMO-SACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

Recovery

Subsequent to fermentation, e.g., SSF, the fermentation product, in particular ethanol may be separated from the fermentation medium. The slurry may be distilled to recover/extract the desired fermentation product (i.e., ethanol). Alternatively the desired fermentation product (i.e., ethanol) may be extracted from the fermentation medium by micro or membrane filtration techniques. The fermentation product (i.e., ethanol) may also be recovered by stripping or other method well known in the art.

Alpha-Amylase Present and/or Added in Liquefaction

According to the invention an alpha-amylase is present and/or added in liquefaction optionally together with other enzymes such as a protease, a glucoamylase, phytase and/or pullulanase. The alpha-amylase added in liquefaction step (a) may be any alpha-amylase. Preferred are bacterial alpha-amylases, which typically are stable at temperatures used in liquefaction.

Bacterial Alpha-Amylase

The term "bacterial alpha-amylase" means any bacterial alpha-amylase classified under EC 3.2.1.1. A bacterial alpha-amylase used according to the invention may, e.g., be derived from a strain of the genus *Bacillus*, which is sometimes also referred to as the genus *Geobacillus*. In an embodiment the *Bacillus* alpha-amylase is derived from a strain of *Bacillus amyloliquefaciens, Bacillus licheniformis, Bacillus stearothermophilus*, or *Bacillus subtilis*, but may also be derived from other *Bacillus* sp. Specific examples of bacterial alpha-amylases include the *Bacillus stearothermophilus* alpha-amylase of SEQ ID NO: 3 in WO 99/19467 or SEQ ID NO: 8 herein, the *Bacillus amyloliquefaciens* alpha-amylase of SEQ ID NO: 5 in WO 99/19467, and the *Bacillus licheniformis* alpha-amylase of SEQ ID NO: 4 in WO 99/19467 (all sequences are hereby incorporated by reference). In an embodiment the alpha-amylase may be an enzyme having a degree of identity of at least 60%, e.g., at least 70%, at least 80%, at least 90%, at least 95%, at least 96%, at least 97%, at least 98% or at least 99% to any of the sequences shown in SEQ ID NOS: 3, 4 or 5, respectively, in WO 99/19467.

In an embodiment the alpha-amylase may be an enzyme having a degree of identity of at least 60%, e.g., at least 70%, at least 80%, at least 90%, at least 91%, at least 92%, at least 93%, at least 94%, at least 95%, at least 96%, at least 97%, at least 98% or at least 99% to any of the sequences shown in SEQ ID NO: 3 in WO 99/19467 or SEQ ID NO: 8 herein.

In a preferred embodiment the alpha-amylase is derived from *Bacillus stearothermophilus*. The *Bacillus stearothermophilus* alpha-amylase may be a mature wild-type or a mature variant thereof.

The mature *Bacillus stearothermophilus* alpha-amylases may naturally be truncated during recombinant production. For instance, the *Bacillus stearothermophilus* alpha-amylase may be a truncated so it has around 491 amino acids, e.g., so that it is between 480-495 amino acids long, so it lacks a functional starch binding domain (compared to SEQ ID NO: 3 in WO 99/19467) or SEQ ID NO: 8 herein.

The *Bacillus* alpha-amylase may also be a variant and/or hybrid. Examples of such a variant can be found in any of WO 96/23873, WO 96/23874, WO 97/41213, WO 99/19467, WO 00/60059, and WO 02/10355 (all documents are hereby incorporated by reference). Specific alpha-amylase variants are disclosed in U.S. Pat. Nos. 6,093,562, 6,187,576, 6,297,038, and 7,713,723 (hereby incorporated by reference) and include *Bacillus stearothermophilus* alpha-amylase (often referred to as BSG alpha-amylase) variants having a deletion of one or two amino acids at positions R179, G180, I181 and/or G182, preferably a double deletion disclosed in WO 96/23873—see, e.g., page 20, lines 1-10 (hereby incorporated by reference), preferably corresponding to deletion of positions I181 and G182 compared to the amino acid sequence of *Bacillus stearothermophilus* alpha-amylase set forth in SEQ ID NO: 3 disclosed in WO 99/19467 or SEQ ID NO: 8 herein or the deletion of amino acids R179 and G180 using SEQ ID NO: 3 in WO 99/19467 or SEQ ID NO: 8 herein for numbering (which reference is hereby incorporated by reference). Even more preferred are *Bacillus* alpha-amylases, especially *Bacillus stearothermophilus* alpha-amylases, which have a double deletion corresponding to a deletion of positions 181 and 182 and further comprise a N193F substitution (also denoted I181*+G182*+N193F) compared to the wild-type BSG alpha-amylase amino acid sequence set forth in SEQ ID NO: 3 disclosed in WO 99/19467 or SEQ ID NO: 8 herein. The bacterial alpha-amylase may also have a substitution in a position corresponding to S239 in the *Bacillus licheniformis* alpha-amylase shown in SEQ ID NO: 4 in WO 99/19467, or a S242 and/or E188P variant of the *Bacillus stearothermophilus* alpha-amylase of SEQ ID NO: 3 in WO 99/19467 or SEQ ID NO: 8 herein.

In an embodiment the variant is a S242A, E or Q variant, preferably a S242Q variant, of the *Bacillus stearothermophilus* alpha-amylase (using SEQ ID NO: 8 herein for numbering).

In an embodiment the variant is a position E188 variant, preferably E188P variant of the *Bacillus stearothermophilus* alpha-amylase (using SEQ ID NO: 8 herein for numbering).

The bacterial alpha-amylase may in an embodiment be a truncated *Bacillus* alpha-amylase.

Especially the truncation is so that, e.g., the *Bacillus stearothermophilus* alpha-amylase shown in SEQ ID NO: 3 in WO 99/19467 or SEQ ID NO: 8 herein, is around 491 amino acids long, such as from 480 to 495 amino acids long, or so it lack a functional starch binding domain.

Bacterial Hybrid Alpha-Amylases

The bacterial alpha-amylase may also be a hybrid bacterial alpha-amylase, e.g., an alpha-amylase comprising 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467). In a preferred embodiment this hybrid has one or more, especially all, of the following substitutions: G48A+T49I+G107A+H156Y+A181T+N190F+I201F+A209V+Q264S (using the *Bacillus licheniformis* numbering in SEQ ID NO: 4 of WO 99/19467). Also preferred are variants having one or more of the following mutations (or corresponding mutations in other *Bacillus* alpha-amylases): H154Y, A181T, N190F, A209V and Q264S and/or the deletion of two residues between positions 176 and 179, preferably the deletion of E178 and G179 (using SEQ ID NO: 5 of WO 99/19467 for position numbering).

In an embodiment the bacterial alpha-amylase is the mature part of the chimeric alpha-amylase disclosed in Richardson et al. (2002), The Journal of Biological Chemistry, Vol. 277, No 29, Issue 19 July, pp. 267501-26507, referred to as BD5088 or a variant thereof. This alpha-amylase is the same as the one shown in SEQ ID NO: 2 in WO 2007134207. The mature enzyme sequence starts after the initial "Met" amino acid in position 1.

Thermostable Alpha-Amylase

The alpha-amylase may be a thermostable alpha-amylase, such as a thermostable bacterial alpha-amylase, preferably from *Bacillus stearothermophilus*.

In an embodiment of the invention the alpha-amylase is an bacterial alpha-amylase, preferably derived from the genus *Bacillus*, especially a strain of *Bacillus stearothermophilus*, in particular the *Bacillus stearothermophilus* as disclosed in WO 99/019467 as SEQ ID NO: 3 (SEQ ID NO: 8 herein) with one or two amino acids deleted at positions R179, G180, I181 and/or G182, in particular with R179 and G180 deleted, or with I181 and G182 deleted, with mutations in below list of mutations.

In preferred embodiments the *Bacillus stearothermophilus* alpha-amylases have double deletion I181+G182, and optionally substitution N193F, further comprising mutations selected from below list:

V59A + Q89R + G112D + E129V + K177L + R179E + K220P + N224L + Q254S;
V59A + Q89R + E129V + K177L + R179E + H208Y + K220P + N224L + Q254S;
V59A + Q89R + E129V + K177L + R179E + K220P + N224L + Q254S + D269E + D281N;
V59A + Q89R + E129V + K177L + R179E + K220P + N224L + Q254S + I270L;
V59A + Q89R + E129V + K177L + R179E + K220P + N224L + Q254S + H274K;

-continued

V59A + Q89R + E129V + K177L + R179E + K220P + N224L + Q254S + Y276F;
V59A + E129V + R157Y + K177L + R179E + K220P + N224L + S242Q + Q254S;
V59A + E129V + K177L + R179E + H208Y + K220P + N224L + S242Q + Q254S;
59A + E129V + K177L + R179E + K220P + N224L + S242Q + Q254S;
V59A + E129V + K177L + R179E + K220P + N224L + S242Q + Q254S + H274K;
V59A + E129V + K177L + R179E + K220P + N224L + S242Q + Q254S + Y276F;
V59A + E129V + K177L + R179E + K220P + N224L + S242Q + Q254S + D281N;
V59A + E129V + K177L + R179E + K220P + N224L + S242Q + Q254S + M284T;
V59A + E129V + K177L + R179E + K220P + N224L + S242Q + Q254S + G416V;
V59A + E129V + K177L + R179E + K220P + N224L + Q254S;
V59A + E129V + K177L + R179E + K220P + N224L + Q254S + M284T;
A91L + M96I + E129V + K177L + R179E + K220P + N224L + S242Q + Q254S;
E129V + K177L + R179E;
E129V + K177L + R179E + K220P + N224L + S242Q + Q254S;
E129V + K177L + R179E + K220P + N224L + S242Q + Q254S + Y276F + L427M;
E129V + K177L + R179E + K220P + N224L + S242Q + Q254S + M284T;
E129V + K177L + R179E + K220P + N224L + S242Q +Q254S + N376* + I377*;
E129V + K177L + R179E + K220P + N224L + Q254S;
E129V + K177L + R179E + K220P + N224L + Q254S + M284T;
E129V + K177L + R179E + S242Q;
E129V + K177L + R179V + K220P + N224L + S242Q + Q254S;
K220P + N224L + S242Q + Q254S;
M284V;
V59A + Q89R + E129V + K177L + R179E + Q254S + M284V.
V59A + E129V + K177L + R179E + Q254S + M284V;

Specific information about the thermostability of above alpha-amylases variants can be found in WO12/088303 (Novozymes) which is hereby incorporated by reference.

In a preferred embodiment the alpha-amylase is selected from the group of *Bacillus stearothermophilus* alpha-amylase variants having a double deletion in I181+G182, and optionally a substitution in N193F, and substitutions from the following list E129V+K177L+R179E;
V59A+Q89R+E129V+K177L+R179E+H208Y+K220P+N224L+Q254S;
V59A+Q89R+E129V+K177L+R179E+Q254S+M284V;
V59A+E129V+K177L+R179E+Q254S+M284V; and
E129V+K177L+R179E+K220P+N224L+S242Q+Q254S
(using SEQ ID NO: 8 herein for numbering).

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 8 herein, or variants thereof, are truncated in the C-terminal and are typically around 491 amino acids long, such as from 480-495 amino acids long, or so that it lacks a functional starch binding domain.

In a preferred embodiment the alpha-amylase variant may be an enzyme having a degree of identity of at least 60%, e.g., at least 70%, at least 80%, at least 90%, at least 95%, at least 91%, at least 92%, at least 93%, at least 94%, at least 95%, at least 96%, at least 97%, at least 98% or at least 99%, but less than 100% to the sequence shown in SEQ ID NO: 3 in WO 99/19467 or SEQ ID NO: 8 herein.

In an embodiment the bacterial alpha-amylase, e.g., *Bacillus* alpha-amylase, such as especially *Bacillus stearothermophilus* alpha-amylase, or variant thereof, is dosed to liquefaction in a concentration between 0.01-10 KNU-A/g DS, e.g., between 0.02 and 5 KNU-A/g DS, such as 0.03 and 3 KNU-A, preferably 0.04 and 2 KNU-A/g DS, such as especially 0.01 and 2 KNU-A/g DS. In an embodiment the bacterial alpha-amylase, e.g., *Bacillus* alpha-amylase, such as especially *Bacillus stearothermophilus* alpha-amylases, or variant thereof, is dosed to liquefaction in a concentration of between 0.0001-1 mg EP(Enzyme Protein)/g DS, e.g., 0.0005-0.5 mg EP/g DS, such as 0.001-0.1 mg EP/g DS.

Protease Present and/or Added in Liquefaction

According to the invention a protease may optionally be present and/or added in liquefaction together with the alpha-amylase, and an optional glucoamylase, phytase and/or pullulanase.

Proteases are classified on the basis of their catalytic mechanism into the following groups: Serine proteases (S), Cysteine proteases (C), Aspartic proteases (A), Metallo proteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

In a preferred embodiment the thermostable protease used according to the invention is a "metallo protease" defined as a protease belonging to EC 3.4.24 (metalloendopeptidases); preferably EC 3.4.24.39 (acid metallo proteinases).

To determine whether a given protease is a metallo protease or not, reference is made to the above "Handbook of Proteolytic Enzymes" and the principles indicated therein. Such determination can be carried out for all types of proteases, be it naturally occurring or wild-type proteases; or genetically engineered or synthetic proteases.

Protease activity can be measured using any suitable assay, in which a substrate is employed, that includes peptide bonds relevant for the specificity of the protease in question. Assay-pH and assay-temperature are likewise to be adapted to the protease in question. Examples of assay-pH-values are pH 6, 7, 8, 9, 10, or 11. Examples of assay-temperatures are 30, 35, 37, 40, 45, 50, 55, 60, 65, 70 or 80° C.

Examples of protease substrates are casein, such as Azurine-Crosslinked Casein (AZCL-casein). Two protease assays are described below in the "Materials & Methods"-section, of which the so-called "AZCL-Casein Assay" is the preferred assay.

There are no limitations on the origin of the protease used in a process of the invention as long as it fulfills the thermostability properties defined below.

In one embodiment the protease is of fungal origin.

The protease may be a variant of, e.g., a wild-type protease as long as the protease is thermostable.

In a preferred embodiment the thermostable protease is a variant of a metallo protease as defined above. In an embodiment the thermostable protease used in a process of the invention is of fungal origin, such as a fungal metallo protease, such as a fungal metallo protease derived from a strain of the genus *Thermoascus*, preferably a strain of *Thermoascus aurantiacus*, especially *Thermoascus aurantiacus* CGMCC No. 0670 (classified as EC 3.4.24.39).

In an embodiment the thermostable protease is a variant of the mature part of the metallo protease shown in SEQ ID NO: 2 disclosed in WO 2003/048353 or the mature part of SEQ ID NO: 1 in WO 2010/008841 and shown as SEQ ID NO: 13 herein, further with mutations selected from below list:

S5*+D79L+S87P+A112P+D142L;
D79L+S87P+A112P+T124V+D142L;
S5*+N26R+D79L+S87P+A112P+D142L;
N26R+T46R+D79L+S87P+A112P+D142L;
T46R+D79L+S87P+T116V+D142L;
D79L+P81R+S87P+A112P+D142L;
A27K+D79L+S87P+A112P+T124V+D142L;
D79L+Y82F+S87P+A112P+T124V+D142L;
D79L+Y82F+S87P+A112P+T124V+D142L;
D79L+S87P+A112P+T124V+A126V+D142L;
D79L+S87P+A112P+D142L;
D79L+Y82F+S87P+A112P+D142L;
S38T+D79L+S87P+A112P+A126V+D142L;
D79L+Y82F+S87P+A112P+A126V+D142L;
A27K+D79L+S87P+A112P+A126V+D142L;
D79L+S87P+N98C+A112P+G135C+D142L;
D79L+S87P+A112P+D142L+T141C+M161C;
S36P+D79L+S87P+A112P+D142L;
A37P+D79L+S87P+A112P+D142L;
S49P+D79L+S87P+A112P+D142L;
S50P+D79L+S87P+A112P+D142L;
D79L+S87P+D104P+A112P+D142L;
D79L+Y82F+S87G+A112P+D142L;
570V+D79L+Y82F+S87G+Y97W+A112P+D142 L;
D79L+Y82F+S87G+Y97W+D104P+A112P+D142L;
S70V+D79L+Y82F+S87G+A112P+D142L;
D79L+Y82F+S87G+D104P+A112P+D142L;
D79L+Y82F+S87G+A112P+A126V+D142L;
Y82F+S87G+S70V+D79L+D104P+A112P+D142L;
Y82F+S87G+D79L+D104P+A112P+A126V+D142L;
A27K+D79L+Y82F+S87G+D104P+A112P+A126V+D142L;
A27K+Y82F+S87G+D104P+A112P+A126V+D142L;
A27K+D79L+Y82F+D104P+A112P+A126V+D142L;
A27K+Y82F+D104P+A112P+A126V+D142L;
A27K+D79L+S87P+A112P+D142L;
D79L+S87P+D142L.

Specific information about the thermostability of above protease variants can be found in WO12/088303 (Novozymes), which is hereby incorporated by reference.

In an preferred embodiment the thermostable protease is a variant of the metallo protease disclosed as the mature part of SEQ ID NO: 2 disclosed in WO 2003/048353 or the mature part of SEQ ID NO: 1 in WO 2010/008841 or SEQ ID NO: 13 herein with the following mutations:

D79L+S87P+A112P+D142L;
D79L+S87P+D142L; or
A27K+D79L+Y82F+S87G+D104P+A112P+A126V+D142L.

In an embodiment the protease variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 2 disclosed in WO 2003/048353 or the mature part of SEQ ID NO: 1 in WO 2010/008841 or SEQ ID NO: 13 herein.

The thermostable protease may also be derived from any bacterium as long as the protease has the thermostability properties defined according to the invention.

In an embodiment the thermostable protease is derived from a strain of the bacterium *Pyrococcus*, such as a strain of *Pyrococcus furiosus* (pfu protease).

In an embodiment the protease is one shown as SEQ ID NO: 1 in U.S. Pat. No. 6,358,726-B1 (Takara Shuzo Company), or SEQ ID NO: 9 herein.

In another embodiment the thermostable protease is one disclosed in SEQ ID NO: 22 herein or a protease having at least 80% identity, such as at least 85%, such as at least 90%, such as at least 95%, such as at least 96%, such as at least 97%, such as at least 98%, such as at least 99% identity to SEQ ID NO: 1 in U.S. Pat. No. 6,358,726-B1 or SEQ ID NO: 9 herein. *Pyroccus furiosus* protease can be purchased from Takara Bio, Japan.

Glucoamylase Present and/or Added in Liquefaction

According to the invention a glucoamylase may optionally be present and/or added in liquefaction step (a). In a preferred embodiment the glucoamylase is added together with or separately from the alpha-amylase and optional protease, phytase and/or pullulanase.

In a specific and preferred embodiment the glucoamylase, preferably of fungal origin, preferably a filamentous fungi, is from a strain of the genus *Penicillium*, especially a strain of *Penicillium oxalicum*, in particular the *Penicillium oxalicum* glucoamylase disclosed as SEQ ID NO: 2 in WO 2011/127802 (which is hereby incorporated by reference) and shown in SEQ ID NO: 10 herein.

In an embodiment the glucoamylase has at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99% or 100% identity to the mature polypeptide shown in SEQ ID NO: 2 in WO 2011/127802 or SEQ ID NO: 10 herein.

In a preferred embodiment the glucoamylase is a variant of the *Penicillium oxalicum* glucoamylase disclosed as SEQ ID NO: 2 in WO 2011/127802 and shown in SEQ ID NO: 10 herein, having a K79V substitution (using the mature sequence shown in SEQ ID NO: 10 herein for numbering). The K79V glucoamylase variant has reduced sensitivity to protease degradation relative to the parent as disclosed in WO 2013/036526 (which is hereby incorporated by reference).

In an embodiment the glucoamylase is derived from *Penicillium oxalicum*.

In an embodiment the glucoamylase is a variant of the *Penicillium oxalicum* glucoamylase disclosed as SEQ ID NO: 2 in WO 2011/127802 and shown in SEQ ID NO: 10 herein. In a preferred embodiment the *Penicillium oxalicum* glucoamylase is the one disclosed as SEQ ID NO: 2 in WO 2011/127802 and shown in SEQ ID NO: 10 herein having Val (V) in position 79 (using SEQ ID NO: 23 herein for numbering).

Contemplated *Penicillium oxalicum* glucoamylase variants are disclosed in WO 2013/053801 which is hereby incorporated by reference.

In an embodiment these variants have reduced sensitivity to protease degradation.

In an embodiment these variant have improved thermostability compared to the parent.

More specifically, in an embodiment the glucoamylase has a K79V substitution (using SEQ ID NO: 10 herein for numbering), (PE001 variant), and further comprises at least one of the following substitutions or combination of substitutions:

T65A; or
Q327F; or
E501V; or
Y504T; or
Y504*; or
T65A+Q327F; or
T65A+E501V; or
T65A+Y504T; or
T65A+Y504*; or
Q327F+E501V; or
Q327F+Y504T; or
Q327F+Y504*; or
E501V+Y504T; or
E501V+Y504*; or
T65A+Q327F+E501V; or
T65A+Q327F+Y504T; or
T65A+E501V+Y504T; or
Q327F+E501V+Y504T; or
T65A+Q327F+Y504*; or
T65A+E501V+Y504*; or
Q327F+E501V+Y504*; or
T65A+Q327F+E501V+Y504T; or
T65A+Q327F+E501V+Y504*;
E501V+Y504T; or
T65A+K161S; or
T65A+Q405T; or
T65A+Q327W; or
T65A+Q327F; or
T65A+Q327Y; or
P11F+T65A+Q327F; or
R1K+D3W+K5Q+G7V+N8S+T10K+P11S+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
R1E+D3N+P4G+G6R+G7A+N8A+T10D+P11D+T65A+Q327F; or
P11F+T65A+Q327W; or
P2N+P4S+P11F+T65A+Q327F+E501V+Y504T; or
P11F+T65A+Q327W+E501V+Y504T; or
T65A+Q327F+E501V+Y504T; or
T65A+S105P+Q327W; or
T65A+S105P+Q327F; or
T65A+Q327W+S364P; or
T65A+Q327F+S364P; or
T65A+S103N+Q327F; or
P2N+P4S+P11F+K34Y+T65A+Q327F; or
P2N+P4S+P11F+T65A+Q327F+D445N+V447S; or
P2N+P4S+P11F+T65A+I172V+Q327F; or
P2N+P4S+P11F+T65A+Q327F+N502*; or
P2N+P4S+P11F+T65A+Q327F+N502T+P563S+K571E; or
P2N+P4S+P11F+R31S+K33V+T65A+Q327F+N564D+K571S; or
P2N+P4S+P11F+T65A+Q327F+S377T; or
P2N+P4S+P11F+T65A+V325T+Q327W; or
P2N+P4S+P11F+T65A+Q327F+D445N+V447S+E501V+Y504T; or
P2N+P4S+P11F+T65A+I172V+Q327F+E501V+Y504T; or
P2N+P4S+P11F+T65A+Q327F+S377T+E501V+Y504T; or
P2N+P4S+P11F+D26N+K34Y+T65A+Q327F; or
P2N+P4S+P11F+T65A+Q327F+I375A+E501V+Y504T; or
P2N+P4S+P11F+T65A+K218A+K221D+Q327F+E501V+Y504T; or
P2N+P4S+P11F+T65A+S103N+Q327F+E501V+Y504T; or
P2N+P4S+T10D+T65A+Q327F+E501V+Y504T; or
P2N+P4S+F12Y+T65A+Q327F+E501V+Y504T; or
K5A+P11F+T65A+Q327F+E501V+Y504T; or
P2N+P4S+T10E+E18N+T65A+Q327F+E501V+Y504T; or
P2N+T10E+E18N+T65A+Q327F+E501V+Y504T; or
P2N+P4S+P11F+T65A+Q327F+E501V+Y504T+T568N; or
P2N+P4S+P11F+T65A+Q327F+E501V+Y504T+K524T+G526A; or
P2N+P4S+P11F+K34Y+T65A+Q327F+D445N+V447S+E501V+Y504T; or
P2N+P4S+P11F+R31S+K33V+T65A+Q327F+D445N+V447S+E501V+Y504T; or
P2N+P4S+P11F+D26N+K34Y+T65A+Q327F+E501V+Y504T; or
P2N+P4S+P11F+T65A+F80*+Q327F+E501V+Y504T; or
P2N+P4S+P11F+T65A+K112S+Q327F+E501V+Y504T; or
P2N+P4S+P11F+T65A+Q327F+E501V+Y504T+T516P+K524T+G526A; or
P2N+P4S+P11F+T65A+Q327F+E501V+N502T+Y504*; or
P2N+P4S+P11F+T65A+Q327F+E501V+Y504T; or
P2N+P4S+P11F+T65A+S103N+Q327F+E501V+Y504T; or
K5A+P11F+T65A+Q327F+E501V+Y504T; or
P2N+P4S+P11F+T65A+Q327F+E501V+Y504T+T516P+K524T+G526A; or
P2N+P4S+P11F+T65A+V79A+Q327F+E501V+Y504T; or
P2N+P4S+P11F+T65A+V79G+Q327F+E501V+Y504T; or
P2N+P4S+P11F+T65A+V79I+Q327F+E501V+Y504T; or
P2N+P4S+P11F+T65A+V79L+Q327F+E501V+Y504T; or
P2N+P4S+P11F+T65A+V79S+Q327F+E501V+Y504T; or
P2N+P4S+P11F+T65A+L72V+Q327F+E501V+Y504T; or
S255N+Q327F+E501V+Y504T; or
P2N+P4S+P11F+T65A+E74N+V79K+Q327F+E501V+Y504T; or
P2N+P4S+P11F+T65A+G220N+Q327F+E501V+Y504T; or
P2N+P4S+P11F+T65A+Y245N+Q327F+E501V+Y504T; or
P2N+P4S+P11F+T65A+Q253N+Q327F+E501V+Y504T; or
P2N+P4S+P11F+T65A+D279N+Q327F+E501V+Y504T; or
P2N+P4S+P11F+T65A+Q327F+S359N+E501V+Y504T; or

P2N+P4S+P11F+T65A+Q327F+D370N+E501V+ Y504T; or
P2N+P4S+P11F+T65A+Q327F+V460S+E501V+ Y504T; or
P2N+P4S+P11F+T65A+Q327F+V460T+P468T+ E501V+Y504T; or
P2N+P4S+P11F+T65A+Q327F+T463N+E501V+ Y504T; or
P2N+P4S+P11F+T65A+Q327F+S465N+E501V+ Y504T; or
P2N+P4S+P11F+T65A+Q327F+T477N+E501V+ Y504T.

In a preferred embodiment the *Penicillium oxalicum* glucoamylase variant has a K79V substitution (using SEQ ID NO: 10 herein for numbering), corresponding to the PE001 variant, and further comprises one of the following mutations:
P11F+T65A+Q327F; or
P2N+P4S+P11F+T65A+Q327F; or
P11F+D26C+K33C+T65A+Q327F; or
P2N+P4S+P11F+T65A+Q327W+E501V+Y504T; or
P2N+P4S+P11F+T65A+Q327F+E501V+Y504T; or
P11F+T65A+Q327W+E501V+Y504T.

The glucoamylase may be added in amounts from 0.1-100 micrograms EP/g, such as 0.5-50 micrograms EP/g, such as 1-25 micrograms EP/g, such as 2-12 micrograms EP/g DS.

Trehalase Present and/or Added in Saccharification and/or Fermentation

According to the process of the invention a trehalase of the invention is present and/or added during the
saccharification step (b);
fermentation step (c);
simultaneous saccharification and fermentation;
optionally presaccharification step before step (b).

In a preferred embodiment the mature trehalase disclosed in SEQ ID NO: 21. In a preferred embodiment the mature trehalase disclosed in SEQ ID NO: 23. In a preferred embodiment the trehalase is present and/or added in an amount between 0.01-20 ug EP (Enzyme Protein) trehalase/g DS, such as between 0.05-15 ug EP terhalase/g DS, such as between 0.5 and 10 ug EP trehalase/g DS.

Glucoamylase Present and/or Added in Saccharification and/or Fermentation

The glucoamylase present and/or added during saccharification step (b); fermentation step (c); simultaneous saccharification and fermentation; or presaccharification before step (b), may be derived from any suitable source, e.g., derived from a microorganism or a plant. Preferred glucoamylases are of fungal or bacterial origin, selected from the group consisting of *Aspergillus* glucoamylases, in particular *Aspergillus niger* G1 or G2 glucoamylase (Boel et al. (1984), EMBO J. 3 (5), p. 1097-1102), or variants thereof, such as those disclosed in WO 92/00381, WO 00/04136 and WO 01/04273 (from Novozymes, Denmark); the *A. awamori* glucoamylase disclosed in WO 84/02921, *Aspergillus oryzae* glucoamylase (Agric. Biol. Chem. (1991), 55 (4), p. 941-949), or variants or fragments thereof. Other *Aspergillus* glucoamylase variants include variants with enhanced thermal stability: G137A and G139A (Chen et al. (1996), Prot. Eng. 9, 499-505); D257E and D293E/Q (Chen et al. (1995), Prot. Eng. 8, 575-582); N182 (Chen et al. (1994), Biochem. J. 301, 275-281); disulphide bonds, A246C (Fierobe et al. (1996), Biochemistry, 35, 8698-8704; and introduction of Pro residues in position A435 and S436 (Li et al. (1997), Protein Eng. 10, 1199-1204.

Other glucoamylases include *Athelia rolfsii* (previously denoted *Corticium rolfsii*) glucoamylase (see U.S. Pat. No. 4,727,026 and (Nagasaka et al. (1998) "Purification and properties of the raw-starch-degrading glucoamylases from *Corticium rolfsii*, Appl Microbiol Biotechnol 50:323-330), *Talaromyces* glucoamylases, in particular derived from *Talaromyces emersonii* (WO 99/28448), *Talaromyces leycettanus* (US patent no. Re. 32,153), *Talaromyces duponti, Talaromyces thermophilus* (U.S. Pat. No. 4,587,215). In a preferred embodiment the glucoamylase used during saccharification and/or fermentation is the *Talaromyces emersonii* glucoamylase disclosed in WO 99/28448.

Bacterial glucoamylases contemplated include glucoamylases from the genus *Clostridium*, in particular *C. thermoamylolyticum* (EP 135,138), and *C. thermohydrosulfuricum* (WO 86/01831). Contemplated fungal glucoamylases include *Trametes* cingulate (SEQ ID NO: 11), *Pachykytospora papyracea*; and *Leucopaxillus giganteus* all disclosed in WO 2006/069289; or *Peniophora rufomarginata* disclosed in WO2007/124285; or a mixture thereof. Also hybrid glucoamylase are contemplated according to the invention. Examples include the hybrid glucoamylases disclosed in WO 2005/045018. Specific examples include the hybrid glucoamylase disclosed in Table 1 and 4 of Example 1 (which hybrids are hereby incorporated by reference).

In an embodiment the glucoamylase is derived from a strain of the genus *Pycnoporus*, in particular a strain of *Pycnoporus sanguineus* as described in WO 2011/066576 (SEQ ID NOs 2, 4 or 6), in particular the one shown a SEQ ID NO: 12 herein (corresponding to SEQ ID NO: 4 in WO 2011/066576) or from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is SEQ ID NO: 2 in WO 2011/068803 or SEQ ID NO: 5 herein (i.e. *Gloeophyllum sepiarium* glucoamylase). In a preferred embodiment the glucoamylase is SEQ ID NO: 6 herein (i.e., *Gloeophyllum trabeum* glucoamylase discloses as SEQ ID NO: 3 in WO2014/177546) (all references hereby incorporated by reference).

Contemplated are also glucoamylases which exhibit a high identity to any of the above mentioned glucoamylases, i.e., at least 60%, such as at least 70%, at least 75%, at least 80%, at least 85%, at least 90%, at least 95%, at least 96%, at least 97%, at least 98%, at least 99% or even 100% identity to any one of the mature parts of the enzyme sequences mentioned above, such as any of SEQ ID NOs: 4, 11, 5, 6 or 12 herein, respectively.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 6 herein.

In an embodiment the glucoamylase used in fermentation or SSF exhibits at least 60%, such as at least 70%, at least 75%, at least 80%, at least 85%, at least 90%, at least 95%, at least 96%, at least 97%, at least 98%, at least 99% or even 100% identity to the mature part of SEQ ID NO: 12 herein.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Glucoamylases may in an embodiment be added to the saccharification and/or fermentation in an amount of 1-1,000 μg EP/g DS, preferably 10-500 μg/gDS, especially between 25-250 μg/g DS.

In an embodiment the glucoamylase is added as a blend further comprising an alpha-amylase. In a preferred embodiment the alpha-amylase is a fungal alpha-amylase, especially an acid fungal alpha-amylase. The alpha-amylase is typically a side activity.

In an embodiment the glucoamylase is a blend comprising *Talaromyces emersonii* glucoamylase disclosed in WO 99/28448 as SEQ ID NO: 34 or SEQ ID NO: 4 herein and *Trametes cingulata* glucoamylase disclosed as SEQ ID NO: 2 in WO 06/069289 and SEQ ID NO: 11 herein.

In an embodiment the glucoamylase is a blend comprising *Talaromyces emersonii* glucoamylase disclosed in SEQ ID NO: 4 herein, *Trametes cingulata* glucoamylase disclosed as SEQ ID NO: 11 herein, and *Rhizomucor pusillus* alpha-amylase with *Aspergillus nigerglucoamylase* linker and SBD disclosed as V039 in Table 5 in WO 2006/069290 or SEQ ID NO: 7 herein.

In an embodiment the glucoamylase is a blend comprising *Gloeophyllum sepiarium* glucoamylase shown as SEQ ID NO: 5 herein and *Rhizomucor pusillus* alpha-amylase with an *Aspergillus niger* glucoamylase linker and starch-binding domain (SBD), disclosed SEQ ID NO: 7 herein with the following substitutions: G128D+D143N.

In an embodiment the alpha-amylase may be derived from a strain of the genus *Rhizomucor*, preferably a strain the *Rhizomucor pusillus*, such as the one shown in SEQ ID NO: 3 in WO2013/006756, or the genus *Meripilus*, preferably a strain of *Meripilus giganteus*. In a preferred embodiment the alpha-amylase is derived from a *Rhizomucor pusillus* with an *Aspergillus niger* glucoamylase linker and starch-binding domain (SBD), disclosed as V039 in Table 5 in WO 2006/069290 or SEQ ID NO: 7 herein.

In an embodiment the *Rhizomucor pusillus* alpha-amylase or the *Rhizomucor pusillus* alpha-amylase with a linker and starch-binding domain (SBD), preferably *Aspergillus niger* glucoamylase linker and SBD, has at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 3 in WO 2013/006756 for numbering or SEQ ID NO: 7 herein). In a preferred embodiment the glucoamylase blend comprises *Gloeophyllum sepiarium* glucoamylase (e.g., SEQ ID NO: 2 in WO 2011/068803 or SEQ ID NO: 5 herein) and *Rhizomucor pusillus* alpha-amylase.

In a preferred embodiment the glucoamylase blend comprises *Gloeophyllum sepiarium* glucoamylase shown as SEQ ID NO: 2 in WO 2011/068803 or SEQ ID NO: 5 herein and *Rhizomucor pusillus* with a linker and starch-binding domain (SBD), preferably *Aspergillus niger* glucoamylase linker and SBD, disclosed SEQ ID NO: 3 in WO 2013/006756 and SEQ ID NO: 7 herein with the following substitutions: G128D+D143N.

Commercially available compositions comprising glucoamylase include AMG 200L; AMG 300 L; SANT™ SUPER, SANT™ EXTRA L, SPIRIZYME™ PLUS, SPIRIZYME™ FUEL, SPIRIZYME™ B4U, SPIRIZYME™ ULTRA, SPIRIZYME™ EXCEL, SPIRIZYME ACHIEVE™, and AMG™ E (from Novozymes A/S); OPTIDEX™ 300, GC480, GC417 (from DuPont-Danisco); AMIGASE™ and AMIGASE™ PLUS (from DSM); G-ZYME™ G900, G-ZYME™ and G990 ZR (from DuPont-Danisco).

Cellulolytic Enzyme Composition Present and/or Added in Saccharification and/or Fermentation According to the invention a cellulolytic enzyme composition may be present in saccharification, fermentation or simultaneous saccharification and fermentation (SSF).

The cellulolytic enzyme composition comprises a beta-glucosidase, a cellobiohydrolase and an endoglucanase.

Examples of suitable cellulolytic composition can be found in WO 2008/151079 and WO 2013/028928 which are incorporated by reference.

In preferred embodiments the cellulolytic enzyme composition is derived from a strain of *Trichoderma, Humicola,* or *Chrysosporium.*

In an embodiment the cellulolytic enzyme composition is derived from a strain of *Trichoderma reesei, Humicola insolens* and/or *Chrysosporium lucknowense.*

In an embodiment the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637 (in particular the *Aspergillus oryzae* beta-glucosidase variant fusion protein shown in SEQ ID NOs: 73 and 74, respectively, in WO 2008/057637 or the *Aspergillus oryzae* beta-glucosidase fusion protein shown in SEQ ID NOs: 75 and 76, respectively, in WO 2008/057637—both hereby incorporated by reference), or *Aspergillus fumigatus*, such as one disclosed in WO 2005/047499 or SEQ ID NO: 14 herein or an *Aspergillus fumigatus* beta-glucosidase variant disclosed in WO 2012/044915 (Novozymes), such as one with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

In an embodiment the cellulolytic enzyme composition comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

In an embodiment the cellulolytic composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 2 in WO 2011/057140 or SEQ ID NO: 17 herein, or a strain of the genus *Trichoderma*, such as a strain of *Trichoderma reesei*.

In an embodiment the cellulolytic composition comprises a cellobiohydrolase II (CBH II, such as one derived from a strain of the genus *Aspergillus*, such as a strain of *Aspergillus fumigatus* disclosed as SEQ ID NO: 18 herein; or a strain of the genus *Trichoderma*, such as *Trichoderma*

*reesei*, or a strain of the genus *Thielavia*, such as a strain of *Thielavia terrestris*, such as cellobiohydrolase II CEL6A from *Thielavia terrestris*.

In an embodiment the cellulolytic enzyme composition comprises a GH61 polypeptide having cellulolytic enhancing activity and a beta-glucosidase.

In an embodiment the cellulolytic composition comprises a GH61 polypeptide having cellulolytic enhancing activity, a beta-glucosidase, and a CBH I.

In an embodiment the cellulolytic composition comprises a GH61 polypeptide having cellulolytic enhancing activity, a beta-glucosidase, a CBH I, and a CBH II.

In an embodiment the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein), and *Aspergillus oryzae* beta-glucosidase fusion protein (WO 2008/057637).

In an embodiment the cellulolytic composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499 or SEQ ID NO: 14 herein). In an embodiment the cellulolytic enzyme composition is a *Trichoderma reesei* cellulolytic enzyme composition further comprising *Penicillium emersonii* GH61A polypeptide having cellulolytic enhancing activity disclosed as SEQ ID NO: 2 in WO 2011/041397 or SEQ ID NO: 16 herein and *Aspergillus fumigatus* beta-glucosidase (SEQ ID NO: 2 of WO 2005/047499 or SEQ ID NO: 14 herein) or a variant thereof with the following substitutions F100D, S283G, N456E, F512Y (using SEQ ID NO: 14 herein for numbering).

In a preferred embodiment the cellulolytic enzyme composition comprising one or more of the following components:
  (i) an *Aspergillus fumigatus* cellobiohydrolase I;
  (ii) an *Aspergillus fumigatus* cellobiohydrolase II;
  (iii) an *Aspergillus fumigatus* beta-glucosidase or variant thereof; and
  (iv) a *Penicillium* sp. GH61 polypeptide having cellulolytic enhancing activity; or homologs thereof.

In an preferred embodiment the cellulolytic enzyme composition is derived from *Trichoderma reesei* comprising GH61A polypeptide having cellulolytic enhancing activity derived from a strain of *Penicillium emersonii* (SEQ ID NO: 2 in WO 2011/041397 or SEQ ID NO: 16 herein), *Aspergillus fumigatus* beta-glucosidase (SEQ ID NO: 2 in WO 2005/047499 or SEQ ID NO: 14 herein) variant with the following substitutions: F100D, S283G, N456E, F512Y (disclosed in WO 2012/044915); *Aspergillus fumigatus* Cel7A CBH I disclosed as SEQ ID NO: 6 in WO2011/057140 or SEQ ID NO: 6 herein and *Aspergillus fumigatus* CBH II disclosed as SEQ ID NO: 17 in WO 2011/057140 or SEQ ID NO: 18 herein.

In an embodiment the cellulolytic composition is dosed from 0.0001-3 mg EP/g DS, preferably, 0.0005-2 mg EP/g DS, preferably 0.001-1 mg/g DS, more preferably 0.005-0.5 mg EP/g DS, and even more preferably 0.01-0.1 mg EP/g DS.

Proteases Present and/or Added in Saccharification and/or Fermentation

Any suitable protease may be added in saccharification and/or fermentation, such as SSF.

In a preferred embodiment the protease is a metallo protease or a serine protease. In an embodiment the enzyme composition comprises a metallo protease, preferably derived from a strain of the genus *Thermoascus*, preferably a strain of *Thermoascus aurantiacus*, especially *Thermoascus aurantiacus* CGMCC No. 0670, such as the metallo protease disclosed as the mature part of SEQ ID NO: 2 disclosed in WO 2003/048353 or the mature polypeptide of SEQ ID NO: 13 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 13 herein.

In an embodiment the protease is derived from a strain of *Pyrococcus*, such as a strain of *Pyrococcus furiosus*, such as the protease shown in SEQ ID NO: 1 in U.S. Pat. No. 6,358,726 or SEQ ID NO: 9 herein.

In an embodiment the protease is the mature sequence from *Meripilus giganteus* protease 3 (peptidase family S53 protease) concerned in Example 2 in WO 2014/037438 (hereby incorporated by reference). In an embodiment the protease is the mature protease 3 sequence from a strain of *Meripilus*, in particular *Meripilus giganteus* shown as SEQ ID NO: 5 in WO 2014/037438 (hereby incorporated by reference) and SEQ ID NO: 19 herein.

In an embodiment the protease has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 19 herein shown as amino acids 1-547.

Alpha-Amylase Present and/or Added in Saccharification and/or Fermentation

Any suitable alpha-amylase, such as fungal acid alpha-amylase, may be present and/or added in saccharification and/or fermentation.

In a preferably embodiment the alpha-amylase is a fungal alpha-amylase, in particular one that has at least 60%, such as at least 70%, such as at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, or 100% identity to the mature part of the polypeptide of SEQ ID NO: 7. In a preferred embodiment the alpha-amylase has one or more of the following substitutions: G128D, D143N, in particular G128D+D143N.

Processes of Producing a Fermentation Product from Cellulolic Materials Using a Trehalase of the Invention In an embodiment the invention relates to processes of producing a fermentation product from pretreated cellulosic material, comprising:
  (a) hydrolyzing said pretreated cellulosic material with a cellulolytic enzyme composition;
  (b) fermenting using a fermenting organism; and
  (c) optionally recovering the fermentation product, wherein a trehalase of the invention is added and/or present in hydrolysis step (a) and/or fermentation step (b).

According to the process of the invention hydrolysis and fermentation may be carried out separate or simultaneous. In an embodiment the process of the invention is carried out as separate hydrolysis and fermentation (SHF); simultaneous saccharification and fermentation (SSF); simultaneous saccharification and co-fermentation (SSCF); hybrid hydrolysis and fermentation (HHF); separate hydrolysis and co-fermentation (SHCF); hybrid hydrolysis and co-fermentation (HHCF); or direct microbial conversion (DMC), also sometimes called consolidated bioprocessing (CBP). SHF uses separate process steps to first enzymatically hydrolyze the cellulosic material to fermentable sugars, e.g., glucose, cellobiose, and pentose monomers, and then ferment the fermentable sugars to ethanol. In SSF, the enzymatic hydrolysis of the cellulosic material and the fermentation of sugars to ethanol are combined in one step. SSCF involves the co-fermentation of multiple sugars (Sheehan, J., and Himmel, M., 1999, Enzymes, energy and the environment: A strategic perspective on the U.S. Department of Energy's research and development activities for bioethanol, *Biotechnol. Prog.* 15: 817-827). HHF involves a separate hydrolysis step, and in addition a simultaneous saccharification and hydrolysis step, which can be carried out in the same reactor. The steps in a HHF process can be carried out at different temperatures, i.e., high temperature enzymatic hydrolysis followed by SSF at a lower temperature that the fermentation strain can tolerate. DMC combines all three processes (enzyme production, hydrolysis, and fermentation) in one or more (e.g., several) steps where the same organism is used to produce the enzymes for conversion of the cellulosic material to fermentable sugars and to convert the fermentable sugars into a final product.

According to the invention the cellulosic material is plant material chips, plant stem segments and/or whole plant stems. In an embodiment cellulosic material is selected from the group comprising *arundo*, bagasse, bamboo, corn cob, corn fiber, corn stover, *miscanthus*, orange peel, rice straw, switchgrass, wheat straw. In a preferred embodiment the source of the cellulosic material is corn stover, corn cobs, and/or wheat straw.

According to the invention any pretreatment may be used. In a preferred embodiment chemical pretreatment, physical pretreatment, or chemical pretreatment and a physical pretreatment is used.

In a preferred embodiment the cellulosic material is pretreated with an acid, such as dilute acid pretreatment. In an embodiment the cellulosic material is prepared by pretreating cellulosic material at high temperature, high pressure with an acid.

In an embodiment hydrolysis is carried out at a temperature between 20-70° C., such as 30-60° C., preferably 45-55° C. at a pH in the range 4-6, such as 4.5-5.5.

In an embodiment the cellulosic material is present at 1-20 (w/w) % of TS, such as 2-10 (w/w) % TS, such as around 5 (w/w) % TS during hydrolysis.

In an embodiment the hydrolysis is carried out for 1-20 days, preferably between from 5-15 days.

In an embodiment the cellulolytic enzyme composition is derived from *Trichoderma reesei, Humicola insolens* or *Chrysosporium lucknowense*.

Cellulolytic enzyme composition: The term "cellulolytic enzyme composition" means one or more (e.g., several) enzymes that hydrolyze a cellulosic material. Such enzymes include endoglucanase(s), cellobiohydrolase(s), beta-glucosidase(s), or combinations thereof. The two basic approaches for measuring cellulolytic activity include: (1) measuring the total cellulolytic activity, and (2) measuring the individual cellulolytic activities (endoglucanases, cellobiohydrolases, and beta-glucosidases) as reviewed in Zhang et al., Outlook for cellulase improvement: Screening and selection strategies, 2006, *Biotechnology Advances* 24: 452-481. Total cellulolytic activity is usually measured using insoluble substrates, including Whatman N21 filter paper, microcrystalline cellulose, bacterial cellulose, algal cellulose, cotton, pretreated lignocellulose, etc. The most common total cellulolytic activity assay is the filter paper assay using Whatman N21 filter paper as the substrate. The assay was established by the International Union of Pure and Applied Chemistry (IUPAC) (Ghose, 1987, Measurement of cellulase activities, *Pure Appl. Chem.* 59: 257-68).

For purposes of the present invention, cellulolytic enzyme activity is determined by measuring the increase in hydrolysis of a cellulosic material by cellulolytic enzyme(s) under the following conditions: 1-50 mg of cellulolytic enzyme protein/g of cellulose in PCS (or other pretreated cellulosic material) for 3-7 days at a suitable temperature, e.g., 50° C., 55° C., or 60° C., compared to a control hydrolysis without addition of cellulolytic enzyme protein. Typical conditions are 1 ml reactions, washed or unwashed PCS, 5% insoluble solids, 50 mM sodium acetate pH 5, 1 mM $MnSO_4$, 50° C., 55° C., or 60° C., 72 hours, sugar analysis by AMINEX® HPX-87H column (Bio-Rad Laboratories, Inc., Hercules, CA, USA).

Examples of cellulolytic compositions can be found in the "Cellulolytic Enzyme Composition present and/or added during Saccharification and/or Fermentation"-section above.

Cellulosic material: The term "cellulosic material" means any material containing cellulose. The predominant polysaccharide in the primary cell wall of cellulosic material is cellulose, the second most abundant is hemicellulose, and the third is pectin. The secondary cell wall, produced after the cell has stopped growing, also contains polysaccharides and is strengthened by polymeric lignin covalently crosslinked to hemicellulose. Cellulose is a homopolymer of anhydrocellobiose and thus a linear beta-(1-4)-D-glucan, while hemicelluloses include a variety of compounds, such as xylans, xyloglucans, arabinoxylans, and mannans in complex branched structures with a spectrum of substituents. Although generally polymorphous, cellulose is found in plant tissue primarily as an insoluble crystalline matrix of parallel glucan chains. Hemicelluloses usually hydrogen bond to cellulose, as well as to other hemicelluloses, which help stabilize the cell wall matrix. Cellulose is generally found, for example, in the stems, leaves, hulls, husks, and cobs of plants or leaves, branches, and wood of trees. The cellulosic material can be, but is not limited to, agricultural residue, herbaceous material (including energy crops), municipal solid waste, pulp and paper mill residue, waste paper, and wood (including forestry residue) (see, for example, Wiselogel et al., 1995, in Handbook on Bioethanol (Charles E. Wyman, editor), pp. 105-118, Taylor & Francis, Washington D.C.; Wyman, 1994, *Bioresource Technology* 50: 3-16; Lynd, 1990, *Applied Biochemistry and Biotechnology* 24/25: 695-719; Mosier et al., 1999, Recent Progress in Bioconversion of Lignocellulosics, in *Advances in Biochemical Engineering/Biotechnology*, T. Scheper, managing editor, Volume 65, pp. 23-40, Springer-Verlag, New York). It is understood herein that the cellulose may be in the form of lignocellulose, a plant cell wall material containing lignin, cellulose, and hemicellulose in a mixed matrix. In a preferred aspect, the cellulosic material is any biomass material.

In another preferred aspect, the cellulosic material is lignocellulose, which comprises cellulose, hemicelluloses, and lignin.

In one aspect, the cellulosic material is agricultural residue. In another aspect, the cellulosic material is herbaceous material (including energy crops). In another aspect, the cellulosic material is municipal solid waste. In another aspect, the cellulosic material is pulp and paper mill residue. In another aspect, the cellulosic material is waste paper. In another aspect, the cellulosic material is wood (including forestry residue).

In another aspect, the cellulosic material is *arundo*. In another aspect, the cellulosic material is bagasse. In another aspect, the cellulosic material is bamboo. In another aspect, the cellulosic material is corn cob. In another aspect, the cellulosic material is corn fiber. In another aspect, the cellulosic material is corn stover. In another aspect, the cellulosic material is *miscanthus*. In another aspect, the cellulosic material is orange peel. In another aspect, the cellulosic material is rice straw.

In another aspect, the cellulosic material is switchgrass. In another aspect, the cellulosic material is wheat straw.

In another aspect, the cellulosic material is aspen. In another aspect, the cellulosic material is *eucalyptus*. In another aspect, the cellulosic material is fir. In another aspect, the cellulosic material is pine. In another aspect, the cellulosic material is poplar. In another aspect, the cellulosic material is spruce. In another aspect, the cellulosic material is willow.

In another aspect, the cellulosic material is algal cellulose. In another aspect, the cellulosic material is bacterial cellulose. In another aspect, the cellulosic material is cotton linter. In another aspect, the cellulosic material is filter paper. In another aspect, the cellulosic material is microcrystalline cellulose. In another aspect, the cellulosic material is phosphoric-acid treated cellulose.

In another aspect, the cellulosic material is an aquatic biomass. As used herein the term "aquatic biomass" means biomass produced in an aquatic environment by a photosynthesis process. The aquatic biomass can be algae, emergent plants, floating-leaf plants, or submerged plants.

The cellulosic material may be used as is or may be subjected to pretreatment, using conventional methods known in the art, as described herein. In a preferred aspect, the cellulosic material is pretreated.

Beta-glucosidase: The term "beta-glucosidase" means a beta-D-glucoside glucohydrolase (E.C. 3.2.1.21) that catalyzes the hydrolysis of terminal non-reducing beta-D-glucose residues with the release of beta-D-glucose. For purposes of the present invention, beta-glucosidase activity is determined using p-nitrophenyl-beta-D-glucopyranoside as substrate according to the procedure of Venturi et al., 2002, Extracellular beta-D-glucosidase from *Chaetomium thermophilum* var. *coprophilum*: production, purification and some biochemical properties, *J. Basic Microbiol.* 42: 55-66. One unit of beta-glucosidase is defined as 1.0 μmole of p-nitrophenolate anion produced per minute at 25° C., pH 4.8 from 1 mM p-nitrophenyl-beta-D-glucopyranoside as substrate in 50 mM sodium citrate containing 0.01% TWEEN® 20 (polyoxyethylene sorbitan monolaurate).

Beta-xylosidase: The term "beta-xylosidase" means a beta-D-xyloside xylohydrolase (E.C. 3.2.1.37) that catalyzes the exo-hydrolysis of short beta (1—>4)-xylooligosaccharides to remove successive D-xylose residues from non-reducing termini. For purposes of the present invention, one unit of beta-xylosidase is defined as 1.0 μmole of p-nitrophenolate anion produced per minute at 40° C., pH 5 from 1 mM p-nitrophenyl-beta-D-xyloside as substrate in 100 mM sodium citrate containing 0.01% TWEEN® 20.

Cellobiohydrolase: The term "cellobiohydrolase" means a 1,4-beta-D-glucan cellobiohydrolase (E.C. 3.2.1.91) that catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain (Teeri, 1997, Crystalline cellulose degradation: New insight into the function of cellobiohydrolases, *Trends in Biotechnology* 15: 160-167; Teeri et al., 1998, *Trichoderma reesei* cellobiohydrolases: why so efficient on crystalline cellulose?, *Biochem. Soc. Trans.* 26: 173-178). Cellobiohydrolase activity is determined according to the procedures described by Lever et al., 1972, *Anal. Biochem.* 47: 273-279; van Tilbeurgh et al., 1982, *FEBS Letters* 149: 152-156; van Tilbeurgh and Claeyssens, 1985, *FEBS Letters* 187: 283-288; and Tomme et al., 1988, *Eur. J. Biochem.* 170: 575-581. In the present invention, the Tomme et al. method can be used to determine cellobiohydrolase activity.

Endoglucanase: The term "endoglucanase" means an endo-1,4-(1,3;1,4)-beta-D-glucan 4-glucanohydrolase (E.C. 3.2.1.4) that catalyzes endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3 glucans such as cereal beta-D-glucans or xyloglucans, and other plant material containing cellulosic components. Endoglucanase activity can be determined by measuring reduction in substrate viscosity or increase in reducing ends determined by a reducing sugar assay (Zhang et al., 2006, *Biotechnology Advances* 24: 452-481). For purposes of the present invention, endoglucanase activity is determined using carboxymethyl cellulose (CMC) as substrate according to the procedure of Ghose, 1987, *Pure and Appl. Chem.* 59: 257-268, at pH 5, 40° C.

Family 61 glycoside hydrolase: The term "Family 61 glycoside hydrolase" or "Family GH61" or "GH61" means a polypeptide falling into the glycoside hydrolase Family 61 according to Henrissat B., 1991, A classification of glycosyl hydrolases based on amino-acid sequence similarities, *Biochem. J.* 280: 309-316, and Henrissat and Bairoch, 1996, Updating the sequence-based classification of glycosyl hydrolases, *Biochem. J.* 316: 695-696. The enzymes in this family were originally classified as a glycoside hydrolase family based on measurement of very weak endo-1,4-beta-D-glucanase activity in one family member. The structure and mode of action of these enzymes are non-canonical and they cannot be considered as bona fide glycosidases. However, they are kept in the CAZy classification on the basis of their capacity to enhance the breakdown of cellulose when used in conjunction with a cellulase or a mixture of cellulases.

Hemicellulolytic enzyme or hemicellulase: The term "hemicellulolytic enzyme" or "hemicellulase" means one or more (e.g., several) enzymes that hydrolyze a hemicellulosic material. See, for example, Shallom and Shoham, 2003, Microbial hemicellulases. *Current Opinion In Microbiology* 6(3): 219-228). Hemicellulases are key components in the degradation of plant biomass. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates of these enzymes, the hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, *Pure & Appl. Chem.* 59: 1739-1752, at a suitable temperature, e.g., 50° C., 55° C., or 60° C., and pH, e.g., 5.0 or 5.5.

Polypeptide having cellulolytic enhancing activity: The term "polypeptide having cellulolytic enhancing activity" means a GH61 polypeptide that catalyzes the enhancement of the hydrolysis of a cellulosic material by enzyme having cellulolytic activity. For purposes of the present invention, cellulolytic enhancing activity is determined by measuring the increase in reducing sugars or the increase of the total of cellobiose and glucose from the hydrolysis of a cellulosic material by cellulolytic enzyme under the following conditions: 1-50 mg of total protein/g of cellulose in PCS, wherein total protein is comprised of 50-99.5% w/w cellulolytic enzyme protein and 0.5-50% w/w protein of a GH61 polypeptide having cellulolytic enhancing activity for 1-7 days at a suitable temperature, e.g., 50° C., 55° C., or 60° C., and pH, e.g., 5.0 or 5.5, compared to a control hydrolysis with equal total protein loading without cellulolytic enhancing activity (1-50 mg of cellulolytic protein/g of cellulose in PCS). In an aspect, a mixture of CELLUCLAST® 1.5L (Novozymes A/S, Bagsværd, Denmark) in the presence of 2-3% of total protein weight *Aspergillus oryzae* beta-glucosidase (recombinantly produced in *Aspergillus oryzae* according to WO 02/095014) or 2-3% of total protein weight *Aspergillus fumigatus* beta-glucosidase (recombinantly produced in *Aspergillus oryzae* as described in WO 2002/095014) of cellulase protein loading is used as the source of the cellulolytic activity.

The GH61 polypeptides having cellulolytic enhancing activity enhance the hydrolysis of a cellulosic material catalyzed by enzyme having cellulolytic activity by reducing the amount of cellulolytic enzyme required to reach the same degree of hydrolysis preferably at least 1.01-fold, e.g., at least 1.05-fold, at least 1.10-fold, at least 1.25-fold, at least 1.5-fold, at least 2-fold, at least 3-fold, at least 4-fold, at least 5-fold, at least 10-fold, or at least 20-fold.

Xylanase: The term "xylanase" means a 1,4-beta-D-xylan-xylohydrolase (E.C. 3.2.1.8) that catalyzes the endohydrolysis of 1,4-beta-D-xylosidic linkages in xylans. For purposes of the present invention, xylanase activity is determined with 0.2% AZCL-arabinoxylan as substrate in 0.01% TRITON® X-100 and 200 mM sodium phosphate buffer pH 6 at 37° C. One unit of xylanase activity is defined as 1.0 µmole of azurine produced per minute at 37° C., pH 6 from 0.2% AZCL-arabinoxylan as substrate in 200 mM sodium phosphate pH 6 buffer.

Fermenting Organism for Cellulosic Based Fermentation

The term "fermenting organism" or 'fermenting microorganism" refers to any organism, including bacterial and fungal organisms, suitable for use in a desired fermentation process to produce a fermentation product. The fermenting organism may be hexose and/or pentose fermenting organisms, or a combination thereof. Both hexose and pentose fermenting organisms are well known in the art. Suitable fermenting microorganisms are able to ferment, i.e., convert, sugars, such as glucose, xylose, xylulose, arabinose, maltose, mannose, galactose, and/or oligosaccharides, directly or indirectly into the desired fermentation product. Examples of bacterial and fungal fermenting organisms producing ethanol are described by Lin et al., 2006, *Appl. Microbiol. Biotechnol.* 69: 627-642.

Examples of fermenting organisms that can ferment hexose sugars include bacterial and fungal organisms, such as yeast. Preferred yeast includes strains of *Candida*, *Kluyveromyces*, and *Saccharomyces*, e.g., *Candida sonorensis*, *Kluyveromyces marxianus*, and *Saccharomyces cerevisiae*.

Examples of fermenting organisms that can ferment pentose sugars in their native state include bacterial and fungal organisms, such as some yeast. Preferred xylose fermenting yeast include strains of *Candida*, preferably *C. sheatae* or *C. sonorensis*; and strains of *Pichia*, preferably *P. stipitis*, such as *P. stipitis* CBS 5773. Preferred pentose fermenting yeast include strains of *Pachysolen*, preferably *P. tannophilus*. Organisms not capable of fermenting pentose sugars, such as xylose and arabinose, may be genetically modified to do so by methods known in the art.

Examples of bacteria that can efficiently ferment hexose and pentose to ethanol include, for example, *Bacillus coagulans*, *Clostridium acetobutylicum*, *Clostridium thermocellum*, *Clostridium phytofermentans*, *Geobacillus* sp., *Thermoanaerobacter saccharolyticum*, and *Zymomonas mobilis* (Philippidis, 1996, supra).

Other fermenting organisms include strains of *Bacillus*, such as *Bacillus coagulans*; *Candida*, such as *C. sonorensis*, *C. methanosorbosa*, *C. diddensiae*, *C. parapsilosis*, *C. naedodendra*, *C. blankii*, *C. entomophilia*, *C. brassicae*, *C. pseudotropicalis*, *C. boidinii*, *C. utilis*, and *C. scehatae*; *Clostridium*, such as *C. acetobutylicum*, *C. thermocellum*, and *C. phytofermentans*; *E. coli*, especially *E. coli* strains that have been genetically modified to improve the yield of ethanol; *Geobacillus* sp.; *Hansenula*, such as *Hansenula anomala*; *Klebsiella*, such as *K. oxytoca*; *Kluyveromyces*, such as *K. marxianus*, *K. lactis*, *K. thermotolerans*, and *K. fragilis*; *Schizosaccharomyces*, such as *S. pombe*; *Thermoanaerobacter*, such as *Thermoanaerobacter saccharolyticum*; and *Zymomonas*, such as *Zymomonas mobilis*.

In a preferred aspect, the yeast is a *Bretannomyces*. In a more preferred aspect, the yeast is *Bretannomyces clausenii*. In another preferred aspect, the yeast is a *Candida*. In another more preferred aspect, the yeast is *Candida sonorensis*. In another more preferred aspect, the yeast is *Candida boidinii*. In another more preferred aspect, the yeast is *Candida blankii*. In another more preferred aspect, the yeast is *Candida brassicae*. In another more preferred aspect, the yeast is *Candida diddensii*. In another more preferred aspect, the yeast is *Candida entomophiliia*. In another more preferred aspect, the yeast is *Candida pseudotropicalis*. In another more preferred aspect, the yeast is *Candida scehatae*. In another more preferred aspect, the yeast is *Candida utilis*. In another preferred aspect, the yeast is a *Clavispora*. In another more preferred aspect, the yeast is *Clavispora lusitaniae*. In another more preferred aspect, the yeast is *Clavispora opuntiae*. In another preferred aspect, the yeast is a *Kluyveromyces*. In another more preferred aspect, the yeast is *Kluyveromyces fragilis*. In another more preferred aspect, the yeast is *Kluyveromyces marxianus*. In another more preferred aspect, the yeast is *Kluyveromyces thermotolerans*. In another preferred aspect, the yeast is a *Pachysolen*. In another more preferred aspect, the yeast is *Pachysolen tannophilus*. In another preferred aspect, the yeast is a *Pichia*. In another more preferred aspect, the yeast is a *Pichia stipitis*.

In another preferred aspect, the yeast is a *Saccharomyces* spp. In a more preferred aspect, the yeast is *Saccharomyces cerevisiae*. In another more preferred aspect, the yeast is *Saccharomyces distaticus*. In another more preferred aspect, the yeast is *Saccharomyces uvarum*.

In a preferred aspect, the bacterium is a *Bacillus*. In a more preferred aspect, the bacterium is *Bacillus coagulans*. In another preferred aspect, the bacterium is a *Clostridium*. In another more preferred aspect, the bacterium is *Clostridium acetobutylicum*. In another more preferred aspect, the bacterium is *Clostridium phytofermentans*. In another more preferred aspect, the bacterium is *Clostridium thermocellum*. In another more preferred aspect, the bacterium is *Geobacillus* sp. In another more preferred aspect, the bacterium is a *Thermoanaerobacter*. In another more preferred aspect, the bacterium is *Thermoanaerobacter saccharolyticum*. In another preferred aspect, the bacterium is a *Zymomonas*. In another more preferred aspect, the bacterium is *Zymomonas mobilis*.

Commercially available yeast suitable for ethanol production include, e.g., BIOFERM™ AFT and XR (NABC—North American Bioproducts Corporation, GA, USA), ETHANOL RED™ yeast (Fermentis/Lesaffre, USA), FALI™ (Fleischmann's Yeast, USA), FERMIOL™ (DSM Specialties), GERT STRAND™ (Gert Strand AB, Sweden), and SUPERSTART™ and THERMOSACC™ fresh yeast (Ethanol Technology, WI, USA).

In a preferred aspect, the fermenting microorganism has been genetically modified to provide the ability to ferment pentose sugars, such as xylose utilizing, arabinose utilizing, and xylose and arabinose co-utilizing microorganisms.

The cloning of heterologous genes into various fermenting microorganisms has led to the construction of organisms capable of converting hexoses and pentoses to ethanol (co-fermentation) (Chen and Ho, 1993, Cloning and improving the expression of *Pichia stipitis* xylose reductase gene in *Saccharomyces cerevisiae*, *Appl. Biochem. Biotechnol.* 39-40: 135-147; Ho et al., 1998, Genetically engineered *Saccharomyces* yeast capable of effectively cofermenting glucose and xylose, *Appl. Environ. Microbiol.* 64: 1852-1859; Kotter and Ciriacy, 1993, Xylose fermentation by *Saccharomyces cerevisiae*, *Appl. Microbiol. Biotechnol.* 38: 776-783; Walfridsson et al., 1995, Xylose-metabolizing *Saccharomyces cerevisiae* strains overexpressing the TKL1 and TAL1 genes encoding the pentose phosphate pathway enzymes transketolase and transaldolase, *Appl. Environ. Microbiol.* 61: 4184-4190; Kuyper et al., 2004, Minimal metabolic engineering of *Saccharomyces cerevisiae* for efficient anaerobic xylose fermentation: a proof of principle, *FEMS Yeast Research* 4: 655-664; Beall et al., 1991, Parametric studies of ethanol production from xylose and other sugars by recombinant *Escherichia coli*, *Biotech. Bioeng.* 38: 296-303; Ingram et al., 1998, Metabolic engineering of bacteria for ethanol production, *Biotechnol. Bioeng.* 58: 204-214; Zhang et al., 1995, Metabolic engineering of a pentose metabolism pathway in ethanologenic *Zymomonas mobilis*, *Science* 267: 240-243; Deanda et al., 1996, Development of an arabinose-fermenting *Zymomonas mobilis* strain by metabolic pathway engineering, *Appl. Environ. Microbiol.* 62: 4465-4470; WO 2003/062430, xylose isomerase).

In a preferred aspect, the genetically modified fermenting microorganism is *Candida sonorensis*. In another preferred aspect, the genetically modified fermenting microorganism is *Escherichia coli*. In another preferred aspect, the genetically modified fermenting microorganism is *Klebsiella oxytoca*.

In another preferred aspect, the genetically modified fermenting microorganism is *Kluyveromyces marxianus*. In another preferred aspect, the genetically modified fermenting microorganism is *Saccharomyces cerevisiae*. In another preferred aspect, the genetically modified fermenting microorganism is *Zymomonas mobilis*.

It is well known in the art that the organisms described above can also be used to produce other substances, as described herein.

The fermenting microorganism is typically added to the degraded cellulosic material or hydrolysate and the fermentation is performed for about 8 to about 96 hours, e.g., about 24 to about 60 hours.

The temperature is typically between about 26° C. to about 60° C., e.g., about 32° C. or 50° C., and about pH 3 to about pH 8, e.g., pH 4-5, 6, or 7.

In one aspect, the yeast and/or another microorganism are applied to the degraded cellulosic material and the fermentation is performed for about 12 to about 96 hours, such as typically 24-60 hours. In another aspect, the temperature is preferably between about 20° C. to about 60° C., e.g., about 25° C. to about 50° C., about 32° C. to about 50° C., or about 32° C. to about 50° C., and the pH is generally from about pH 3 to about pH 7, e.g., about pH 4 to about pH 7. However, some fermenting organisms, e.g., bacteria, have higher fermentation temperature optima. Yeast or another microorganism is preferably applied in amounts of approximately $10^5$ to $10^{12}$, preferably from approximately $10^7$ to $10^{10}$, especially approximately $2 \times 10^8$ viable cell count per ml of fermentation broth. Further guidance in respect of using yeast for fermentation can be found in, e.g., "The Alcohol Textbook" (Editors K. Jacques, T. P. Lyons and D. R. Kelsall, Nottingham University Press, United Kingdom 1999), which is hereby incorporated by reference.

For ethanol production, following the fermentation the fermented slurry is distilled to extract the ethanol. The ethanol obtained according to the processes of the invention can be used as, e.g., fuel ethanol, drinking ethanol, i.e., potable neutral spirits, or industrial ethanol.

A fermentation stimulator can be used in combination with any of the processes described herein to further improve the fermentation process, and in particular, the performance of the fermenting microorganism, such as, rate enhancement and ethanol yield. A "fermentation stimulator" refers to stimulators for growth of the fermenting microorganisms, in particular, yeast. Preferred fermentation stimulators for growth include vitamins and minerals. Examples of vitamins include multivitamins, biotin, pantothenate, nicotinic acid, meso-inositol, thiamine, pyridoxine, para-aminobenzoic acid, folic acid, riboflavin, and Vitamins A, B, C, D, and E. See, for example, Alfenore et al., Improving ethanol production and viability of *Saccharomyces cerevisiae* by a vitamin feeding strategy during fed-batch process, Springer-Verlag (2002), which is hereby incorporated by reference. Examples of minerals include minerals and mineral salts that can supply nutrients comprising P, K, Mg, S, Ca, Fe, Zn, Mn, and Cu.

Fermentation Products

According to the invention the term "fermentation product" can be any substance derived from fermentation. The fermentation product can be, without limitation, an alcohol (e.g., arabinitol, n-butanol, isobutanol, ethanol, glycerol, methanol, ethylene glycol, 1,3-propanediol [propylene glycol], butanediol, glycerin, sorbitol, and xylitol); an alkane (e.g., pentane, hexane, heptane, octane, nonane, decane, undecane, and dodecane), a cycloalkane (e.g., cyclopentane, cyclohexane, cycloheptane, and cyclooctane), an alkene (e.g. pentene, hexene, heptene, and octene); an amino acid (e.g., aspartic acid, glutamic acid, glycine, lysine, serine, and threonine); a gas (e.g., methane, hydrogen ($H_2$), carbon dioxide ($CO_2$), and carbon monoxide (CO)); isoprene; a ketone (e.g., acetone); an organic acid (e.g., acetic acid, acetonic acid, adipic acid, ascorbic acid, citric acid, 2,5-diketo-D-gluconic acid, formic acid, fumaric acid, glucaric acid, gluconic acid, glucuronic acid, glutaric acid, 3-hydroxypropionic acid, itaconic acid, lactic acid, malic acid, malonic acid, oxalic acid, oxaloacetic acid, propionic acid, succinic acid, and xylonic acid); and polyketide. The fermentation product can also be protein as a high value product.

In a preferred aspect, the fermentation product is an alcohol. It will be understood that the term "alcohol" encompasses a substance that contains one or more (e.g., several) hydroxyl moieties. In a more preferred aspect, the alcohol is n-butanol. In another more preferred aspect, the alcohol is isobutanol. In another more preferred aspect, the alcohol is ethanol. In another more preferred aspect, the alcohol is methanol. In another more preferred aspect, the alcohol is arabinitol. In another more preferred aspect, the alcohol is butanediol. In another more preferred aspect, the alcohol is ethylene glycol. In another more preferred aspect, the alcohol is glycerin. In another more preferred aspect, the alcohol is glycerol. In another more preferred aspect, the alcohol is 1,3-propanediol. In another more preferred aspect, the alcohol is sorbitol. In another more preferred aspect, the alcohol is xylitol. See, for example, Gong, C. S., Cao, N. J., Du, J., and Tsao, G. T., 1999, Ethanol production from renewable resources, in *Advances in Biochemical Engineering/Biotechnology*, Scheper, T., ed., Springer-Verlag Berlin Heidelberg, Germany, 65: 207-241; Silveira, M. M., and Jonas, R., 2002, The biotechnological production of sorbitol, *Appl. Microbiol. Biotechnol.* 59: 400-408; Nigam and Singh, 1995, Processes for fermentative production of xylitol—a sugar substitute, *Process Biochemistry* 30(2): 117-124; Ezeji et al., 2003, Production of acetone, butanol and ethanol by *Clostridium beijerinckii* BA101 and in situ recovery by gas stripping, *World Journal of Microbiology and Biotechnology* 19(6): 595-603.

In another preferred aspect, the fermentation product is an alkane. The alkane can be an unbranched or a branched alkane. In another more preferred aspect, the alkane is pentane. In another more preferred aspect, the alkane is hexane. In another more preferred aspect, the alkane is heptane. In another more preferred aspect, the alkane is octane. In another more preferred aspect, the alkane is nonane. In another more preferred aspect, the alkane is decane. In another more preferred aspect, the alkane is undecane. In another more preferred aspect, the alkane is dodecane.

In another preferred aspect, the fermentation product is a cycloalkane. In another more preferred aspect, the cycloalkane is cyclopentane. In another more preferred aspect, the cycloalkane is cyclohexane. In another more preferred aspect, the cycloalkane is cycloheptane. In another more preferred aspect, the cycloalkane is cyclooctane.

In another preferred aspect, the fermentation product is an alkene. The alkene can be an unbranched or a branched alkene. In another more preferred aspect, the alkene is pentene. In another more preferred aspect, the alkene is hexene. In another more preferred aspect, the alkene is heptene. In another more preferred aspect, the alkene is octene.

In another preferred aspect, the fermentation product is an amino acid. In another more preferred aspect, the organic acid is aspartic acid. In another more preferred aspect, the amino acid is glutamic acid. In another more preferred aspect, the amino acid is glycine. In another more preferred aspect, the amino acid is lysine. In another more preferred aspect, the amino acid is serine. In another more preferred aspect, the amino acid is threonine. See, for example, Richard and Margaritis, 2004, Empirical modeling of batch fermentation kinetics for poly(glutamic acid) production and other microbial biopolymers, *Biotechnology and Bioengineering* 87(4): 501-515.

In another preferred aspect, the fermentation product is a gas. In another more preferred aspect, the gas is methane. In another more preferred aspect, the gas is $H_2$. In another more preferred aspect, the gas is $CO_2$. In another more preferred aspect, the gas is CO. See, for example, Kataoka, Miya, and Kiriyama, 1997, Studies on hydrogen production by continuous culture system of hydrogen-producing anaerobic bacteria, *Water Science and Technology* 36(6-7): 41-47; and Gunaseelan, 1997, Anaerobic digestion of biomass for methane production: A review, *Biomass and Bioenergy,* 13(1-2): 83-114.

In another preferred aspect, the fermentation product is isoprene.

In another preferred aspect, the fermentation product is a ketone. It will be understood that the term "ketone" encompasses a substance that contains one or more (e.g., several) ketone moieties. In another more preferred aspect, the ketone is acetone. See, for example, Qureshi and Blaschek, 2003, supra.

In another preferred aspect, the fermentation product is an organic acid. In another more preferred aspect, the organic acid is acetic acid. In another more preferred aspect, the organic acid is acetonic acid. In another more preferred aspect, the organic acid is adipic acid. In another more preferred aspect, the organic acid is ascorbic acid. In another more preferred aspect, the organic acid is citric acid. In another more preferred aspect, the organic acid is 2,5-diketo-D-gluconic acid. In another more preferred aspect, the organic acid is formic acid. In another more preferred aspect, the organic acid is fumaric acid. In another more preferred aspect, the organic acid is glucaric acid. In another more preferred aspect, the organic acid is gluconic acid. In another more preferred aspect, the organic acid is glucuronic acid. In another more preferred aspect, the organic acid is glutaric acid. In another preferred aspect, the organic acid is 3-hydroxypropionic acid. In another more preferred aspect, the organic acid is itaconic acid. In another more preferred aspect, the organic acid is lactic acid. In another more preferred aspect, the organic acid is malic acid. In another more preferred aspect, the organic acid is malonic acid. In another more preferred aspect, the organic acid is oxalic acid. In another more preferred aspect, the organic acid is propionic acid. In another more preferred aspect, the organic acid is succinic acid. In another more preferred aspect, the organic acid is xylonic acid. See, for example, Chen and Lee, 1997, Membrane-mediated extractive fermentation for lactic acid production from cellulosic biomass, *Appl. Biochem. Biotechnol.* 63-65: 435-448.

Recovery

The fermentation product(s) are optionally recovered after fermentation using any method known in the art including, but not limited to, chromatography, electrophoretic procedures, differential solubility, distillation, or extraction. For example, alcohol, such as ethanol, is separated from the fermented material and purified by conventional methods of distillation. Ethanol with a purity of up to about 96 vol. % can be obtained, which can be used as, for example, fuel ethanol, drinking ethanol, i.e., potable neutral spirits, or industrial ethanol.

The present invention is further disclosed in the following numbered embodiments.

Embodiment 1. A polypeptide having trehalase activity, selected from the group consisting of:
 (a) a polypeptide having at least 93% sequence identity to the mature polypeptide of SEQ ID NO: 21 or at least 70% sequence identity to the mature polypeptide of SEQ ID NO: 23;
 (b) a polypeptide encoded by a polynucleotide having at least 95% sequence identity to the mature polypeptide coding sequence of SEQ ID NO: 20 or the cDNA sequence thereof; or at least 80% sequence identity to the mature polypeptide coding sequence of SEQ ID NO: 22 or the cDNA sequence thereof;
 (c) a variant of the mature polypeptide of SEQ ID NO: 21 or SEQ ID NO: 23 comprising a substitution, deletion, and/or insertion at one or more (e.g., several) positions; and
 (d) a fragment of the polypeptide of (a), (b), or (c), that has trehalase activity.

Embodiment 2. The polypeptide of embodiment 1, having at least 93%, at least 94%, at least 95%, at least 96%, at least 97%, at least 98%, at least 99% or 100% sequence identity to the mature polypeptide of SEQ ID NO: 21.

Embodiment 3. The polypeptide of any of embodiments 1-2, which is encoded by a polynucleotide having at least 96%, at least 97%, at least 98%, at least 99% or 100% sequence identity to the mature polypeptide coding sequence of SEQ ID NO: 20 or the cDNA sequence thereof.

Embodiment 4. The polypeptide of any of embodiments 1-3, comprising or consisting of SEQ ID NO: 21 or the mature polypeptide of SEQ ID NO: 21 shown as amino acids 19-1038 of SEQ ID NO: 21.

Embodiment 5. The polypeptide of embodiment 1, having at least 75%, at least, 80%, at least 85%, at least 90%, at least 91%, at least 92%, at least 93%, at least 94%, at least 95%, at least 96%, at least 97%, at least 98%, at least 99% or 100% sequence identity to the mature polypeptide of SEQ ID NO: 23.

Embodiment 6. The polypeptide of embodiment 1, which is encoded by a polynucleotide having at least 85%, at least 90%, at least 91%, at least 92%, at least 93%, at least 94%, at least 95%, at least 96%, at least 97%, at least 98%, at least 99% or 100% sequence identity to the mature polypeptide coding sequence of SEQ ID NO: 22 or the cDNA sequence thereof.

Embodiment 7. The polypeptide of embodiment 1, comprising or consisting of SEQ ID NO: 23 or the mature polypeptide of SEQ ID NO: 23 shown as amino acids 21-1089 of SEQ ID NO: 23.

Embodiment 8. The polypeptides of any of the preceding embodiments, having a thermal denaturing temperature, Td, determined by TSA of at least 60° C., at least 61° C., at least 62° C., at least 63° C., at least 64° C., at least 65° C., at least 66° C., at least 67° C., such as at least 68° C.

Embodiment 9. A composition comprising the polypeptide of any of embodiments 1-8.

Embodiment 10. A whole broth formulation or cell culture composition comprising the polypeptide of any of embodiments 1-8.

Embodiment 11. A polynucleotide encoding the polypeptide of any of embodiments 1-8.

Embodiment 12. A nucleic acid construct or expression vector comprising the polynucleotide of embodiment 11 operably linked to one or more heterologous control sequences that direct the production of the polypeptide in an expression host.

Embodiment 13. A recombinant host cell comprising the nucleic acid construct embodiment 12.

Embodiment 14. The recombinant host cell of embodiment 13, wherein the cell is a yeast cell, particularly a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell, most particularly *Saccharomyces cerevisiae*.

Embodiment 15. A method of producing a polypeptide having trehalase activity, comprising cultivating the host cell of embodiment 13 or 14 under conditions conducive for production of the polypeptide.

Embodiment 16. The method of embodiment 15, further comprising recovering the polypeptide.

Embodiment 17. A process of producing a fermentation product, comprising
 (a) liquefying a starch-containing material with an alpha-amylase; optionally pre-saccharifying the liquefied material before step (b);
 (b) saccharifying the liquefied material;
 (c) fermenting using a fermentation organism;
 wherein
  i) a glucoamylase;
  ii) a trehalase of any of embodiments 1-8;
  iii) optionally a cellulolytic enzyme composition and/or a protease;
 are present and/or added during
  saccharification step (b);
  fermentation step (c);
  simultaneous saccharification and fermentation;
  optionally presaccharification step before step (b).

Embodiment 18. The process of embodiment 17, wherein the alpha-amylase is a bacterial alpha-amylase, in particular of the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 8 herein.

Embodiment 19. The process of embodiment 18, wherein the *Bacillus stearothermophilus* alpha-amylase or variant thereof is truncated, preferably to be from 485-495 amino acids long, such as around 491 amino acids long.

Embodiment 20. The process of any of embodiments 17-19, wherein the *Bacillus stearothermophilus* alpha-amylase has a double deletion at positions I181+G182, and optionally a N193F substitution, or deletion of R179+G180 (using SEQ ID NO: 8 for numbering).

Embodiment 21. The process of any of embodiments 17-20, wherein the *Bacillus stearothermophilus* alpha-amylase has a substitution in position S242, preferably a S242A, E or Q substitution (using SEQ ID NO: 8 for numbering).

Embodiment 22. The process of any of embodiments 17-21, wherein the *Bacillus stearothermophilus* alpha-amylase has a substitution in position E188, preferably E188P substitution (using SEQ ID NO: 8 for numbering).

Embodiment 23. The process of any of embodiments 17-22, wherein the alpha-amylase in liquefaction step (a) is selected from the following group of *Bacillus stearothermophilus* alpha-amylase variants:
I181*+G182*+N193F+E129V+K177L+R179E;
I181*+G182*+N193F+V59A+Q89R+E129V+K177L+ R179E+H208Y+K220P+N224L+Q254S
I181*+G182*+N193F+V59A+Q89R+E129V+K177L+ R179E+Q254S+M284V;
I181*+G182*+N193F+V59A+E129V+K177L+R179E+ Q254S+M284V and
I181*+G182*+N193F+E129V+K177L+R179E+K220P+ N224L+S242Q+Q254S (using SEQ ID NO: 8 herein for numbering).

Embodiment 24. The process of any of embodiments 17-23, wherein the glucoamylase is of fungal origin, preferably from a strain of *Aspergillus*, preferably *A. niger, A. awamori*, or *A. oryzae*; or a strain of *Trichoderma*, preferably *T. reesei*; or a strain of *Talaromyces*, preferably *T. emersonii*, or a strain of *Gloeophyllum*, such as *G. serpiarium* or *G. trabeum*.

Embodiment 25. The process of any of embodiments 17-24, wherein the glucoamylase is derived from *Talaromyces emersonii*, such as the one shown in SEQ ID NO: 4 herein.

Embodiment 26. The process of any of embodiments 17-25, wherein the glucoamylase is selected from the group consisting of:
(i) a glucoamylase comprising the polypeptide of SEQ ID NO: 4 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 4 herein.

Embodiment 27. The process of any of embodiments 17-24, wherein the glucoamylase is derived from *Gloeophyllum serpiarium*, such as the one shown in SEQ ID NO: 5 herein.

Embodiment 28. The process embodiment 27, wherein the glucoamylase is selected from the group consisting of:
(i) a glucoamylase comprising the polypeptide of SEQ ID NO: 5 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 5 herein.

Embodiment 29. The process of any of embodiments 17-24, wherein the glucoamylase is derived from *Gloeophyllum trabeum* such as the one shown in SEQ ID NO: 6 herein.

Embodiment 30. The process of embodiment 29, wherein the glucoamylase present and/or added in saccharification is selected from the group consisting of:
(i) a glucoamylase comprising the polypeptide of SEQ ID NO: 6 herein;
(ii) a glucoamylase comprising an amino acid sequence having at least 60%, at least 70%, e.g.,
at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 6 herein.

Embodiment 31. The process of any of embodiments 17-30, further wherein an alpha-amylase is present and/or added during saccharification step (b); fermentation step (c); simultaneous saccharification and fermentation; or the optional presaccharification step before step (b).

Embodiment 32. The process of embodiment 31, wherein the alpha-amylase is of fungal or bacterial origin.

Embodiment 33. The process of embodiment 31 or 32, wherein the alpha-amylase is derived from a strain of the genus *Rhizomucor*, preferably a strain the *Rhizomucor pusillus*, such as the one shown in SEQ ID NO: 3 in WO 2013/006756, such as a *Rhizomucor pusillus* alpha-amylase hybrid having an *Aspergillus niger* linker and starch-bonding domain, such as the one shown in SEQ ID NO: 7 herein.

Embodiment 34. The process of any of embodiments 31-33, wherein the alpha-amylase present and/or added in saccharification and/or fermentation is selected from the group consisting of:
(i) an alpha-amylase comprising the polypeptide of SEQ ID NO: 7 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 7 herein.

Embodiment 35. The process of any of embodiments 31-34, wherein the alpha-amylase is a variant of the alpha-amylase shown in SEQ ID NO: 7 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 7 for numbering).

Embodiment 36. The process of any of embodiments 33-35, wherein the alpha-amylase is derived from a *Rhizomucor pusillus*, in particular with an *Aspergillus niger* glucoamylase linker and starch-binding domain (SBD), preferably the one disclosed as SEQ ID NO: 7 herein, preferably having one or more of the following substitutions: G128D, D143N, preferably G128D+D143N (using SEQ ID NO: 7 for numbering).

Embodiment 37. The process of any of embodiments 35-36, wherein the alpha-amylase variant has at least 60% identity, such as at least 70%, preferably at least 75% identity, preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the mature part of the polypeptide of SEQ ID NO: 7 herein.

Embodiment 38. The process of any of embodiments 17-37, wherein the cellulolytic enzyme composition is derived from *Trichoderma reesei, Humicola insolens* or *Chrysosporium lucknowense*.

Embodiment 39. The process of any of embodiments 17-38, wherein the cellulolytic enzyme composition comprises a beta-glucosidase, a cellobiohydrolase, an endoglucanase and optionally a GH61 polypeptide.

Embodiment 40. The process of any of embodiment 17-39, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 14 herein or an *Aspergillus fumigatus* beta-glucosidase variant disclosed in WO 2012/044915; in particular an *Aspergillus fumigatus* beta-glucosidase variant with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

Embodiment 41. The process of any of embodiments 17-40, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 17 herein, or a strain of the genus *Trichoderma*, such as a strain of *Trichoderma reesei*.

Embodiment 42. The process of any of embodiments 17-41, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 18 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Embodiment 43. The process of any of embodiments 17-42, wherein the cellulolytic enzyme composition further comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

Embodiment 44. The process of any of embodiments 17-43, wherein the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499) or SEQ ID NO: 14 herein.

Embodiment 45. The process of any of embodiments 17-44, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 16 herein; and *Aspergillus fumigatus* beta-glucosidase (SEQ ID NO: 2 of WO 2005/047499 or SEQ ID NO: 14 herein) or a variant thereof with one or more, such as all, of the following substitutions: F100D, S283G, N456E, F512Y.

Embodiment 46. The process of any of embodiments 17-45, wherein the cellulolytic enzyme composition is dosed from 0.0001-3 mg EP/g DS, preferably 0.0005-2 mg EP/g DS, preferably 0.001-1 mg/g DS, more preferred from 0.005-0.5 mg EP/g DS, even more preferred 0.01-0.1 mg EP/g DS.

Embodiment 47. The process of any of embodiments 17-46, wherein the presaccharification is carried out at a temperature from 40-75° C., such as 50-70° C., preferably 60° C.; a pH between 4-6, preferably 5; for a period of 30-360 minutes, such as from 60-420 minutes, such as around between 150-180 minutes.

Embodiment 48. A process of any of embodiments 17-47, comprising the steps of:
  (a) liquefying a starch-containing material with an alpha-amylase; optionally pre-saccharifying the liquefied material before step (b);
  (b) saccharifying the liquefied material;
  (c) fermenting using a fermentation organism;
  wherein
    i) a glucoamylase;
    ii) a trehalase of any of embodiments 1-8;
  are present and/or added during
    saccharification step (b);
    fermentation step (c);
    simultaneous saccharification and fermentation;
    optionally presaccharification step before step (b).

Embodiment 49. A process of any of embodiments 17-48, comprising the steps of:
  (a) liquefying a starch-containing material with an alpha-amylase;
    optionally pre-saccharifying the liquefied material before step (b);
  (b) saccharifying the liquefied material;
  (c) fermenting using a fermentation organism;
  wherein
    i) a glucoamylase from *Talaromyces emersonii* or *Gloeophyllum* serpiarium;
    ii) a trehalase shown in any of embodiments 1-8;
  are present and/or added during
    saccharification step (b);
    fermentation step (c);
    simultaneous saccharification and fermentation;
    optionally presaccharification step before step (b).

Embodiment 50. A process of any of embodiments 17-49, comprising the steps of:
  (a) liquefying a starch-containing material with an alpha-amylase;
    optionally pre-saccharifying the liquefied material before step (b);
  (b) saccharifying the liquefied material;
  (c) fermenting using a fermentation organism;
  wherein
    i) a glucoamylase from *Talaromyces emersonii* or *Gloeophyllum* serpiarium;
    ii) a trehalase shown any of embodiments 1-8;
    iii) a cellulolytic enzyme composition derived from *Trichoderma reesei*;
  are present and/or added during
    saccharification step (b);
    fermentation step (c);
    simultaneous saccharification and fermentation;
    optionally presaccharification step before step (b).

Embodiment 51. The process of any of embodiments 17-50, wherein saccharification step (a) and fermentation step (b) are done separately or simultaneously.

Embodiment 52. The process of any of embodiments 17-51, wherein the fermentation product is recovered after fermentation.

Embodiment 53. The process of any of embodiments 17-52, wherein the starch-containing material is plant material selected from the corn (maize), cobs, wheat, barley, rye, milo, sago, cassava, tapioca, sorghum, rice, peas, beans, sweet potatoes, or a mixture thereof, preferably corn.

Embodiment 54. The process of any of embodiments 17-53, wherein the temperature in liquefaction is above the initial gelatinization temperature, in particular in the range from 70-100° C., such as between 75-95° C., such as between 75-90° C., preferably between 80-90° C., such as 82-88° C., such as around 85° C.

Embodiment 55. The process of any of embodiments 17-54, wherein liquefaction step (a) is carried out at a pH in the range between 3 and 7, preferably from 4 to 6, or more preferably from 4.5 to 5.5.

Embodiment 56. The process of any of embodiments 17-55, wherein the dry solid content (DS) in liquefaction lies in the range from 20-55 wt.-%, preferably 25-45 wt.-%, more preferably 30-40 wt.-% or 30-45 wt-%.

Embodiment 57. The process of any of embodiments 17-56, further comprises, prior to the liquefaction step (a), the steps of:
x) reducing the particle size of the starch-containing material, preferably by dry milling;
y) forming a slurry comprising the starch-containing material and water.

Embodiment 58. The process of any of embodiments 17-57, wherein a jet-cooking step is carried out prior to liquefaction in step (a).

Embodiment 59. The process of any of embodiments 17-58, wherein the starch-containing material is reduced in particle size, such by dry milling or wet milling or using particle size emulsion technology.

Embodiment 60. The process of any of embodiments 17-59, wherein the fermentation is carried out for 30 to 150 hours, preferably 48 to 96 hours.

Embodiment 61. The process of any of embodiments 17-60, wherein the temperature during fermentation in step (b) or simultaneous saccharification and fermentation in steps (a) and (b) is between 25° C. and 40° C., preferably between 28° C. and 36° C., such as between 28° C. and 35° C., such as between 28° C. and 34° C., such as around 32° C.

Embodiment 62. The process of any of embodiments 17-61, wherein further a protease is present during saccharification and/or fermentation.

Embodiment 63. The process of any of embodiments 17-62, wherein glucoamylase is present and/or added in an amount of 0.001 to 10 AGU/g DS, preferably from 0.01 to 5 AGU/g DS, especially 0.1 to 0.5 AGU/g DS.

Embodiment 64. The process of any of embodiments 17-63, wherein the fermentation product is an alcohol, preferably ethanol, especially fuel ethanol, potable ethanol and/or industrial ethanol.

Embodiment 65. The process of any of embodiments 17-64, further wherein a protease is present and/or added during
saccharification step (b);
fermentation step (c);
simultaneous saccharification and fermentation;
optionally presaccharification step before step (b).

Embodiment 66. The process of any of embodiments 17-65, wherein the protease is derived from *Thermoascus*, in particular *Thermoascus aurantiacus*, especially *Thermoascus aurantiacus* CGMCC No. 0670 (classified as EC 3.4.24.39) shown in SEQ ID NO: 13 herein.

Embodiment 67. The process of embodiment 66, wherein the protease is the one shown in SEQ ID NO: 13 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 13 herein.

Embodiment 68. The process of any of embodiments 17-65, wherein the protease is derived from a strain of *Meripilus*, in particular *Meripilus giganteus*, in particular the one shown as SEQ ID NO: 19 herein.

Embodiment 69. The process of embodiment 68, wherein the protease is the one shown in SEQ ID NO: 19 herein or a protease being at least 60%, such as at least 70%, such as at least 80%, such as at least 90%, such as at least 95%, such as at least 96%, such as at least 97%, as as at least 98%, such as at least 99% identical to SEQ ID NO: 19 herein.

Embodiment 70. The process of any of embodiments 17-69, wherein the fermenting organism is derived from a strain of *Saccharomyces*, such as *Saccharomyces cerevisae*.

Embodiment 71. The process according to any of the embodiments 17-70, wherein the yeast fermenting organism expresses the trehalse according to embodiments 1-8.

Embodiment 72. A process of producing fermentation products from starch-containing material comprising:
(i) saccharifying a starch-containing material at a temperature below the initial gelatinization temperature; and
(ii) fermenting using a fermentation organism;
wherein saccharification and/or fermentation is done in the presence of the following enzymes: glucoamylase, alpha-amylase, trehalase of any of embodiments 1-8, and optionally a protease and/or a cellulolytic enzyme composition.

Embodiment 73. A process of producing a fermentation product from pretreated cellulosic material, comprising:
(a) hydrolyzing said pretreated cellulosic material with a cellulolytic enzyme composition;
(b) fermenting using a fermenting organism; and
(c) optionally recovering the fermentation product,
wherein a trehalase of any of embodiments 1-8 is added and/or present in hydrolysis step (a) and/or fermentation step (b).

Embodiment 74. The process of any of embodiments 17-73, wherein the trehalase is added in an amount between 0.01-20 ug EP trehalase/g DS, such as between 0.05-15 ug EP terhalase/g DS, such as between 0.5 and 10 ug EP trehalase/g DS.

Embodiment 75. The process of any of embodiments 17-74, wherein the cellulolytic enzyme composition is derived from *Trichoderma reesei, Humicola insolens* or *Chrysosporium lucknowense*.

Embodiment 76. The process of any of embodiments 72-75, wherein the cellulolytic enzyme composition comprising a beta-glucosidase, a cellobiohydrolase, an endoglucanase and optionally a GH61 polypeptide.

Embodiment 77. The process of any of embodiment 72-76, wherein the cellulolytic enzyme composition comprises a beta-glucosidase, preferably one derived from a strain of the genus *Aspergillus*, such as *Aspergillus oryzae*, such as the one disclosed in WO 2002/095014 or the fusion protein having beta-glucosidase activity disclosed in WO 2008/057637, or *Aspergillus fumigatus*, such as one disclosed in SEQ ID NO: 2 in WO 2005/047499 or SEQ ID NO: 14 herein or an *Aspergillus fumigatus* beta-glucosidase variant disclosed in WO 2012/044915; in particular an *Aspergillus fumigatus* beta-glucosidase variant with one or more, such as all, of the following substitutions: F100D, S283G, N456E, F512Y; or a strain of the genus a strain *Penicillium*, such as a strain of the *Penicillium brasilianum* disclosed in WO 2007/019442, or a strain of the genus *Trichoderma*, such as a strain of *Trichoderma reesei*.

Embodiment 78. The process of any of embodiments 72-77, wherein the cellulolytic enzyme composition comprises a cellobiohydrolase I (CBH I), such as one derived from a strain of the genus *Aspergillus*, such as a strain of *Aspergillus fumigatus*, such as the Cel7a CBH I disclosed in SEQ ID NO: 6 in WO 2011/057140 or SEQ ID NO: 17 herein, or a strain of the genus *Trichoderma*, such as a strain of *Trichoderma reesei*.

Embodiment 79. The process of any of embodiments 72-78, wherein the cellulolytic enzyme composition comprises a cellobiohydrolase II (CBH II, such as one derived from a strain of the genus *Aspergillus*, such as a strain of *Aspergillus fumigatus*; such as the one disclosed as SEQ ID NO: 18 herein or a strain of the genus *Trichoderma*, such as *Trichoderma reesei*, or a strain of the genus *Thielavia*, such as a strain of *Thielavia terrestris*, such as cellobiohydrolase II CEL6A from *Thielavia terrestris*.

Embodiment 80. The process of any of embodiments 72-79, wherein the cellulolytic enzyme composition further comprises a GH61 polypeptide having cellulolytic enhancing activity such as one derived from the genus *Thermoascus*, such as a strain of *Thermoascus aurantiacus*, such as the one described in WO 2005/074656 as SEQ ID NO: 2 or SEQ ID NO: 15 herein; or one derived from the genus *Thielavia*, such as a strain of *Thielavia terrestris*, such as the one described in WO 2005/074647 as SEQ ID NO: 7 and SEQ ID NO: 8; or one derived from a strain of *Aspergillus*, such as a strain of *Aspergillus fumigatus*, such as the one described in WO 2010/138754 as SEQ ID NO: 1 and SEQ ID NO: 2; or one derived from a strain derived from *Penicillium*, such as a strain of *Penicillium emersonii*, such as the one disclosed in WO 2011/041397 as SEQ ID NO: 2 or SEQ ID NO: 16 herein.

Embodiment 81. The process of any of embodiments 72-80, wherein the cellulolytic enzyme composition is a *Trichoderma reesei* cellulolytic enzyme composition, further comprising *Thermoascus aurantiacus* GH61A polypeptide having cellulolytic enhancing activity (SEQ ID NO: 2 in WO 2005/074656 or SEQ ID NO: 15 herein) and *Aspergillus fumigatus* beta-glucosidase (SEQ ID NO: 2 of WO 2005/047499) or SEQ ID NO: 14 herein.

Embodiment 82. The process of any of embodiments 72-81, wherein the cellulolytic enzyme composition is a *Trichoderma reesei* cellulolytic enzyme composition further comprising *Penicillium emersonii* GH61A polypeptide having cellulolytic enhancing activity disclosed in WO 2011/041397 as SEQ ID NO: 2 or SEQ ID NO: 16 herein; and *Aspergillus fumigatus* beta-glucosidase (SEQ ID NO: 2 of WO 2005/047499 or SEQ ID NO: 14 herein) or a variant thereof with one or more, such as all, of the following substitutions: F100D, S283G, N456E, F512Y.

Embodiment 83. The process of any of embodiments 72-82, wherein the cellulolytic enzyme composition is dosed from 0.0001-3 mg EP/g DS, preferably 0.0005-2 mg EP/g DS, preferably 0.001-0.1 mg/g DS, more preferred from 0.005-0.5 mg EP/g DS, even more preferred 0.01-0.1 mg EP/g DS.

The present invention is further described by the following examples.

EXAMPLES

Materials & Methods
Enzymes and Yeast Used:
Alpha-Amylase BE369 (AA369): *Bacillus stearothermophilus* alpha-amylase disclosed herein as SEQ ID NO: 8, and further having the mutations: I181*+G182*+N193F+V59A+Q89R+E129V+K177L+R179E+Q254S+M284V truncated to 491 amino acids (using SEQ ID NO: 8 for numbering).

Protease PfuS shown in SEQ ID NO: 9 herein.

Glucoamylase X: Blend comprising *Talaromyces emersonii* glucoamylase disclosed as SEQ ID NO: 34 in WO99/28448 (SEQ ID NO: 4 herein), *Trametes cingulata* glucoamylase disclosed as SEQ ID NO: 2 in WO 06/69289 (SEQ ID NO: 11 herein), and *Rhizomucor pusillus* alpha-amylase with *Aspergillus niger* glucoamylase linker and starch binding domain (SBD) disclosed in SEQ ID NO: 7 herein having the following substitutions G128D+D143N using SEQ ID NO: 7 for numbering (activity ratio in AGU:AGU:FAU-F is about 29:8:1).

Yeast: Ethanol Red®
Trehalase Assay:
PRINCIPLE:

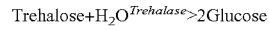

$$\text{Trehalose} + H_2O \xrightarrow{Trehalase} 2\text{Glucose}$$

T=37° C., pH=5.7, A340 nm, Light path=1 cm
Spectrophotometric Stop Rate Determination
Unit Definition:
One unit will convert 1.0 mmole of trehalose to 2.0 mmoles of glucose per minute at pH 5.7 at 37° C. (liberated glucose determined at pH 7.5).
(See Dahlqvist, A. (1968) Analytical Biochemistry 22, 99-107)
Trehalase Assay Used in Example 3.

Ten microliters of sample was mixed with 190 µl of substrate solution (1% trehalose in 50 mM sodium acetate, pH 4.3) and incubate at 32° C. for 1 hour. 10 µl of the solution was then taken out and 200 µl of glucose CII test WAKO was added. A505 was measured after 15 min-incubation at room temperature.

Strains

An improved *Aspergillus oryzae* host/vector system comparable to the one described in example 5 disclosed in WO 2016026938A1 was constructed. The improvement was made to reduce the size of the transforming DNA by moving the FLPase expression cassette located on PART-11 of the plasmid pDAu724 (see page 34, FIG. 7 and SEQ ID NO:30 in WO 2016026938A1) to the integration locus amy2 in the genome of the host strain. The cloning of the FLPase expression cassette into pDAu703 (WO 2016026938A1 page 32 and FIG. 6 and SEQ ID:29) was done by amplification of the FLPase expression cassette from pDAu724 and cloning in between FRT-F3 and the amdS selection marker of pDAu703 to give the plasmid pDAu770. The same protocol as described in WO 2016026938A1 page 33 was used to transform the linearized plasmid pDAu770 into protoplasts of *A. oryzae* strain Ja11338 (disclosed in WO12160097A1). Transformants were selected on AmdS selection plates to obtain strain DAu785. The resulting recombinant host strain DAu785 has a modified amy2 locus comparable to the one in DAU716 (WO 2016026938A1) with the addition of the FLPase expression cassette. The host strain DAu785 is constitutively expressing the FLPase site specific recombinase allowing the integration at the FRT sites of the transforming DNA in this case the PCR fragments obtained by Overlap Extension PCR reaction described below. This strain was used for heterologous expression of the trehalase polypeptides SEQ ID NO: 21, and SEQ ID NO: 23.

*Talaromyces funiculosus* NRRL 1035 was kindly obtained in February 1992 from Pr. Jens Frisvad (Denmark Technical University, Department of Biotechnology and Biomedicine). *T. funiculosus* was originally isolated by George Smith in England in 1936. The strain was inoculated onto a PDA plate and incubated for 8 days at 26° C. in the darkness. Several mycelia-PDA plugs were inoculated into 500 ml shake flasks containing 100 ml of YPG medium. The shake flasks were incubated for 5 days at 26° C. with shaking at 100 rpm for production of biomass.

*Talaromyces leycettanus* reference CBS 398.68 (isolated in 1968 in England) was purchased from CBS-KNAW Fungal Biodiversity Centre, Uppsalalaan 8, 3584 CT, Utrecht, The Netherlands and inoculated onto a PDA plate and incubated for 8 days at 26° C. in the darkness. Several mycelia-PDA plugs were inoculated into 500 ml shake flasks containing 100 ml of YPG medium. The flasks were incubated for 5 days at 26° C. with shaking at 100 rpm for production of biomass.

Media and Solutions

PDA plates were composed of 39 g Potato Dextrose Agar (ref. 70139) (Sigma-Aldrich, Munich, Germany) and deionized water to 1000 ml. The medium was sterilized by autoclaving at 15 psi for 15 minutes (Bacteriological Analytical Manual, 8th Edition, Revision A, 1998).

LB-Bouillon was composed of 25 g of LB Bouillon (ref. L3152) (Sigma-Aldrich, Munich, Germany) and deionised water to 1000 ml. The medium was sterilized by autoclaving at 15 psi for 15 minutes (Bacteriological Analytical Manual, 8th Edition, Revision A, 1998).

Ampicillin LB-agar was composed of 37 g LB agar (ref. L3027) (Sigma-Aldrich, Munich, Germany), 5 g soluble starch, 0.01 M K2PO4, 0.04% glucose, and deionised water to 1000 ml. The medium was sterilized by autoclaving at 15 psi for 15 minutes (Bacteriological Analytical Manual, 8th Edition, Revision A, 1998). Medium was cooled to 50° C. and 50 mM ampicillin was added.

COVE-N-agar plates were composed of 218 g of sorbitol, 25 g of agar powder, 50 ml of COVE salt solution, and deionized water to 1000 ml. The medium was sterilized by autoclaving at 15 psi for 15 minutes (Bacteriological Analytical Manual, 8th Edition, Revision A, 1998). The medium was cooled to 50° C. and 10 mM acetamide, and Triton X-100 (50 µl/500 ml) were added.

Sucrose Agar 10 mM NaNO3 was composed of 342 g sucrose, 20 g agar powder, 20 ml COVE salt solution, and deionised water to 1000 ml. The medium was sterilized by autoclaving at 15 psi for 15 minutes (Bacteriological Analytical Manual, 8th Edition, Revision A, 1998). The medium was cooled to 50° C. and 10 mM NaNO3, and Triton X-100 (50 µl/500 ml) were added.

COVE salt solution was composed of 26 g of MgSO4·7H2O, 26 g of KCL, 76 g of KH2PO4, 50 ml of COVE trace metal solution, and deionized water to 1000 ml. Solution was sterile filtered.

COVE trace metal solution was composed of 0.04 g of Na2B4O7·10H2O, 0.4 g of CuSO4·5H2O, 1.2 g of FeSO4·7H2O, 0.7 g of MnSO4·H2O, 0.8 g of Na2MoO4·2H2O, 10 g of ZnSO4·7H2O, and deionised water to 1000 ml. Solution was sterile filtered.

DAP4C-1 medium was composed of 0.5 g yeast extract, 10 g maltose, 20 g dextrose, 11 g MgSO4·7H2O, 1 g KH2PO4, 2 g C6H8O7·H2O, 5.2 g K3PO4·H2O, 1 ml Dowfax 63N10 (antifoaming agent), 2.5 g calcium carbonate, supplemented with 0.5 ml KU6 trace metal solution, and deionised water to 1000 ml. The medium was sterilized by autoclaving at 15 psi for 15 minutes (Bacteriological Analytical Manual, 8th Edition, Revision A, 1998). Before use, 3.5 ml of sterile 50% (NH4)2HPO4 and 5 ml of sterile 20% lactic acid were added per 150 ml of DAP4C-1 medium.

MDU-2 medium was composed of 45 g maltose, 1 g MgSO4·7H2O, 1 g NaCl, 2 g K2SO4, 12 g KH2PO4, 0.5 ml KU6 trace metal, 0.1 ml Dowfax 63N10 (antifoaming agent), and deionised water to 1000 ml. pH was adjusted to pH5 and the medium was sterilized by autoclaving at 15 psi for 15 minutes (Bacteriological Analytical Manual, 8th Edition, Revision A, 1998). 15 ml 50% sterile filtered urea was added after autoclaving.

YP2% glucose was composed of 10 g yeast extract, 20 g Bacto peptone, 20 g dextrose, and deionized water to 1000 ml. The medium was sterilized by autoclaving at 15 psi for 15 minutes (Bacteriological Analytical Manual, 8th Edition, Revision A, 1998).

KU6 trace metal solution was composed of 6.8 g ZnCl2, 2.5 g CuSO4·5H2O, 0.13 g NiCl2, 13.9 g FeSO4·7H2O, 8.45 g MnSO4·H2O, 3 g C6H8O7·H2O, and deionised water to 1000 ml. Solution was sterile filtered.

Example 1: Cloning of Trehalase Sequence

*Talaromyces* DNA sequences were PCR amplified from gDNA from *Talaromyces funiculosus* and *Talaromyces leycettanus* and cloned by overlap-extension PCR. pDAu724 plasmid (see Strain section above) was used as DNA template to amplify two PCR products (F1 and F3) in reactions composed of 10 µl of KAPA polymerase buffer 5×, 1 µl 10 mM KAPA PCR Nucleotide Mix, 1 µl of 10 µM of the appropriate forward primers (SEQ ID NO: 24 for F1 and SEQ ID NO: 26 for F3), 1 µl of 10 µM of the appropriate reverse primers (SEQ ID NO: 25 for F1 and SEQ ID NO: 27 for F3), 1 to 10 ng of pDAu724 plasmid, 1 µl of KAPA Biosystems polymerase KK2502 (1 unit) and PCR-grade water up to 50 µL. PCR amplification reactions were carried out on a DYAD® Dual-Block Thermal Cycler (MJ Research Inc., Waltham, MA, USA) programmed for 2 min. at 98° C. and followed by 35 cycles of 10 sec. at 98° C. and 2 min. at 72° C. and one final cycle of 10 min. at 72° C. Five µl of the PCR reaction were analysed by 1% agarose gel electrophoresis using TAE buffer where DNA bands of the appropriate size were observed. The remaining PCR reactions were purified using an ILLUSTRA™ GFX™ PCR DNA and Gel Band Purification Kit according to the manufacturer's instructions.

Overlap Extension PCR reactions for cloning trehalase genes amplified from *Talaromyces funiculosus*, and *Talaromyces leycettanus* respectively were composed of 10 µl KAPA polymerase buffer (5×), 1 µl 10 mM KAPA PCR Nucleotide Mix, 50 ng of PCR fragment F1 and equimolar amounts of PCR fragment F3 and trehalase genes encoding for SEQ ID NO: 21, or SEQ ID NO: 23, 1 µl KAPA Biosystems polymerase KK2502 (1 unit) and PCR-grade water up to 48 µL. Reactions were incubated on a DYAD® Dual-Block Thermal Cycler (MJ Research Inc., Waltham, MA, USA) using a program composed of 2 min. at 98° C., followed by 5 cycles each composed of 10 sec. at 98° C., 30 sec. at 68° C., and 5 min. at 72° C. and completed by a final extension of 8 min. at 72° C. During the Overlap Extention PCR reactions, annealing between fragment F1 and trehalase genes encoding for SEQ ID NO: 21, and SEQ ID NO: 23 was ensured by overlap sequence SEQ ID NO: 28 included in the forward cloning primers (SEQ ID NO: 31 and SEQ ID NO: 30). Annealing between fragment F3 and the trehalase genes encoding for SEQ ID NO: 21, SEQ ID NO: 23 was ensured by the overlap sequence SEQ ID NO: 29 included in the reverse cloning primers (SEQ ID NO: 33 and SEQ ID NO: 32). One µl of 10 µM primer SEQ ID NO: 24 and 1 µl of 10 µM primer SEQ ID NO: 27 were added to the Overlap Extention PCR reactions after the five initial cycles and the reactions were incubated a second time on a DYAD® Dual-Block Thermal Cycler (MJ Research Inc., Waltham, MA, USA) using a program composed of 2 min. at 98° C.; followed by 25 cycles each composed of 10 sec. at 98° C., and 4 min. at 72° C. and completed by a final extension of 10 min. at 72° C. The PCR reactions resulted in two products: SEQ ID NO: 20 and SEQ ID NO: 22. Five µl of the PCR reactions were analysed by 1% agarose gel electrophoresis using TAE buffer where an DNA bands of the appropriate size were observed. The remaining PCR reactions were up-concentrated to 20 µl by heating the tubes at 60° C. Ten µl of those reactions were used for *Aspergillus oryzae* DAu785 protoplasts transformation.

Example 2: Heterologous Expression of Trehalases

Protoplasts of *Aspergillus oryzae* DAu785 strain were prepared according to WO 95/002043. 100 µl of *A. oryzae* protoplasts were mixed with 10 µl of up-concentrated Overlap Extention PCR encoding for *Talaromyces funiculosus*, and *Talaromyces leycettanus* trehalases polypeptide (amino acids 19-1038 of SEQ ID NO: 21 and amino acids 21-1089 of SEQ ID NO: 23), and 270 µl of 60% PEG 4000 (Applichem, Darmstadt, Germany) (polyethylene glycol, molecular weight 4,000), 10 mM $CaCl_2$), and 10 mM Tris-HCl pH 7.5 and gently mixed. The mixture was incubated at 37° C. for 30 minutes and the protoplasts were spread onto Sucrose Agar plates containing 10 mM $NaNO_3$. After incubation for 4-7 days at 37° C., spores of eight colonies were inoculated into MDU-2 medium in 96-well X50 microtiter plate PS from ThermoFisher (Life Technologies Europe BV, Nrum, Denmark) and covered with semi-permeable tape. After 4 days of static incubation at 30° C., the culture broths were analysed by sodium dodecyl sulfate polyacrylamide gel electrophoresis to identify colonies producing the highest amount of trehalase polypeptides. Spores of the best transformant were spread onto Sucrose Agar plates containing 0.01% TRITON® X-100 and 10 mM $NaNO_3$ to isolate single colonies. The spreading was repeated twice.

Example 3: Characterization of Trehalases of the Invention

| Trehalases | Organism | GH |
|---|---|---|
| Ms-trehalase | *Myceliophthora sepedonium* | 37 |
| Tr-trehalase | *Trichoderma reesei* | 65 |
| An-trehalase | *Aspergillus niger* | 65 |
| Tl-trehalase | *Talaromyces leycettanus* | 65 |
| Tf-trehalase | *Talaromyces funiculosus* | 65 |

Purification

Purification of trehalase enzymes were carried out by two steps, desalting column and cation exchange chromatography column. Finally, the sample was dialyzed against 10 L of 20 mM sodium acetate buffer (pH 4.0) using 12k-14k MWCO (molecular weight-cutoff) dialysis membrane and then concentrated using 30k MWCO centrifugal filter unit.

Thermostability Determination (TSA)

Purified enzyme was diluted to 0.5 mg/ml with 50 mM sodium acetate buffer (pH 4.5) and mixed with equal volume of SYPRO Orange (Invitrogen) diluted with Milli-Q water. Eighteen microliters of mixture solution was transfer to LightCycler 480 Multiwell Plate 384 (Roche Diagnostics) and the plate was sealed.

Equipment parameters of TSA:
  Apparatus: LightCycler 480 Real-Time PCR System (Roche Applied Science)
  Scan rate: 0.02° C./sec
  Scan range: 37-96° C.
  Integration time: 1.0 sec
  Excitation wave length 465 nm
  Emission wave length 580 nm The obtained fluorescence signal was normalized into a range of 0 and 1. The denaturing temperature (Td) was defined as the temperature where the normalized value is closest to 0.5. The temperature where the maximum signal intensity (normalized value is 1) was defined as Td2 and it used for an index of thermostability of M-tre PE variants.

Trehalase Assay

Ten microliters of sample was mixed with 190 µl of substrate solution (1% trehalose in 50 mM sodium acetate, pH 4.3) and incubate at 32° C. for 1 hour. 10 µl of the solution was then taken out and 200 of glucose CII test WAKO was added. A505 was measured after 15 min-incubation at room temperature.

SF Cultivation for Protease Cocktail Preparation

*Aspergillus niger* strains used to prepare protease cocktail is derivatives of NN059095, which was isolated by Novozymes and genetically modified to disrupt expression of amyloglycosidase activities from *Aspergillus niger* NN049184 isolated from soil.

Spores of *Aspergillus niger* strains were inoculated in 100 ml MLC media and cultivated at 30° C. for 2 days. 10 ml of MLC was inoculated to 100 ml of MU-1 medium and cultivated at 30° C. for 7 days. The supernatant was obtained by centrifugation.

MLC is composed of 40 g glucose, 50 g soybean powder, 4 g citric acid (pH 5) and water to 1 liter. MU-1-glu is composed of 260 g glucose, 3 g $MgSO_4 \cdot 7H_2O$, 5 g $KH_2PO_4$, 6 g $K_2SO_4$, 0.5 ml of trace metal solution and 2 g urea (pH 4.5) and water to 1 liter.

Trace metal solution is composed of 6.8 g $ZnCl_2 \cdot 7H_2O$, 2.5 g $CuSO_4 \cdot 5H_2O$, 0.24 g $NiCl_2 \cdot 6H_2O$, 13.9 g $FeSO_4 \cdot 7H_2O$, 13.5 g $MnSO_4 \cdot H_2O$ and 3 g citric acid and water to 1 liter.

Protease Stability Assay

Purified enzyme was diluted to 2 mg/ml with 50 mM sodium acetate buffer pH 4.0 and 100 µl of the sample was mixed with 100 µl of prepared protease cocktail. The solution was then incubated at −20, 4, 30 and 40° C. for 3 days and the residual activity was measured by trehalase assay.

Results

| | | Protease stability* | | |
|---|---|---|---|---|
| Trehalases | Td [° C.] | 4° C. | 30° C. | 40° C. |
| Ms-trehalase SEQ ID NO: 1 | 56.9 | 90% | 42% | 15% |

-continued

| Trehalases | Td [° C.] | Protease stability* | | |
|---|---|---|---|---|
| | | 4° C. | 30° C. | 40° C. |
| Tr-trehalase SEQ ID NO: 2 | 57.9 | 100% | 100% | 100% |
| An-trehalase SEQ ID NO: 3 | 53.1 | 100% | 97% | 68% |
| Tl-trehalase SEQ ID NO: 23 | 69.0 | 100% | 100% | 100% |
| Tf-trehalase SEQ ID NO: 21 | 65.2 | 100% | 100% | 100% |

*Residual activity after 3 days-incubation in an admixture with protease cocktail (−20° C. as 100%)

Example 4: Thermo-Stability of the Trehalases According to the Invention Compared to Two Prior Art Trehalases Thermo-stability of the trehalases of the invention, disclosed herein as SEQ ID NO: 21 and SEQ ID NO: 23, where compared to two prior art trehalses; one from *Talaromyces cellulolyticus* (SEQ ID NO: 34) (Fujii T, Hoshino T, Inoue H, Yano S. 2014. Taxonomic revision of the cellulose-degrading fungus *Acremonium cellulolyticus* nomen *nudum* to *Talaromyces* based on phylogenetic analysis. FEMS Microbiology Letters. 351:32-41) and one from *Talaromyces verruculosus* (SEQ ID NO: 35) (published in 2015 as part of a genome sequence on the NCBI website as assembly GCA 001305275.1; polypeptide identified as EFP5BRM8N). The thermo-stability was measured as denaturing temperature using a Thermal Shift Assay (TSA).

Samples

| Trehalase | Organism |
|---|---|
| EXP13116 (SEQ ID NO: 34) | *Talaromyces celluloyticus* |
| EXP13117 (SEQ ID NO: 35) | *Talaromyces verruculosus* |
| Tl-trehalase (SEQ ID NO: 23) | *Talaromyces leycettanus* |
| Tf-trehalase (SEQ ID NO: 21) | *Talaromyces funiculosus* |

Strain Cultivation

Agar pieces of a strain cultivated onto COVE N-gly agar plate for 1 week at 30° C. were inoculated to 100 ml of MS9 in a 500 ml shaking flask and it was cultivated at 30° C. for 1 day with shaking at 220 rpm. Three ml of the seed culture was transferred to 100 ml of MDU-2BP-FuPE in 500 ml shaking flask and it was cultivated at 30° C. for 3 days with shaking at 220 rpm. The culture supernatant was filtrated with 0.2 μm cellulose acetate filter. Media components are described below.

COVE Ngly Agar 218 g/L Sorbitol, 10 g/L Glycerol, 2.02 g/L Potassium Nitrate, 50 ml/L salt solution for COVE, pH 5.3

Salt Solution for COVE 26 g/L Potassium Chloride, 26 g/L Magnesium Sulfate Heptahydrate, 76 g/L Potassium Dihydrogenphosphate, 50 ml/L Trace metal solution for COVE Trace Metal Solution for COVE 0.04 g/L Sodium Tetraborate Decahydrate, 0.4 g/L Copper (II) Sulfate Pentahydrate, 1.2 g/L Iron (II) Sulfate Heptahydrate, 1 g/L Manganese(II) Sulfate Pentahydrate, 0.8 g/L Sodium molybdate dihydrate, 10 g/L Zinc Sulfate Heptahydrate

MS9

30 g/L Soybean powder, 20 g/L Glycerol

MDU-2BP FuPE 45 g/L Maltodextrin, 7 g/L Yeast extract, 1 g/L Magnesium Sulfate Heptahydrate, 1 g/L Sodium Chloride, 2 g/L Potassium Sulfate, 0.75 g/L Ammonium Chloride, 12 g/L Potassium Dihydrogenphosphate, 0.5 ml/L Trace metal solution for AMG (MU-1)

Trace Metal Solution for AMG (MU-1)

1.39% Iron (II) Sulfate Heptahydrate, 1.356% Manganese (II) Sulfate Pentahydrate, 0.68% Zinc Chloride, 0.25% Copper(II) Sulfate Pentahydrate, 0.024 g/L Nickel (II) Chloride Hexahydrate, 0.3% Citric acid Purification Purification of WT trehalases were carried out by two steps, desalting column and cation exchange chromatography column. Finally, the sample was dialyzed against 10 L of 20 mM sodium acetate buffer (pH 4.0) using 12k-14k MWCO dialysis membrane and then concentrated using 30k MWCO centrifugal filter unit.

Thermostability Determination (TSA)

Purified enzyme was diluted to 0.5 mg/ml with 50 mM sodium acetate buffer (pH 4.5) and mixed with equal volume of SYPRO Orange (Invitrogen) diluted with Milli-Q water. Eighteen microliters of mixture solution was transfer to LightCycler 480 Multiwell Plate 384 (Roche Diagnostics) and the plate was sealed.

Equipment Parameters of TSA

Apparatus: LightCycler 480 Real-Time PCR System (Roche Applied Science)

Scan rate: 0.02° C./sec

Scan range: 37-96° C.

Integration time: 1.0 sec

Excitation wave length 465 nm

Emission wave length 580 nm

The obtained fluorescence signal was normalized into a range of 0 and 1. The denaturing temperature (Td) was defined as the temperature where the normalized value is closest to 0.5. Td are listed in TABLE 1.

TABLE 1

List of Td

| Trehalase | Td [° C.] |
|---|---|
| EXP13116 | 51.7 |
| EXP13117 | 47.1 |
| Tl-trehalase | 67.5 |
| Tf-trehalase | 64.7 |

Example 5: Use of Tf-Trehalase of the Invention in a Process for Producing Ethanol Enzymes and Yeast Used:

Alpha-Amylase BE369 (AA369): *Bacillus stearothermophilus* alpha-amylase disclosed herein as SEQ ID NO: 8, and further having the mutations: I181*+G182*+N193F+V59A+Q89R+E129V+K177L+R179E+Q254S+M284V truncated to 491 amino acids (using SEQ ID NO: 8 for numbering).

Protease PfuS shown in SEQ ID NO: 9 herein.

Glucoamylase X: Blend comprising *Talaromyces emersonii* glucoamylase disclosed as SEQ ID NO: 34 in WO99/28448 (SEQ ID NO: 4 herein), *Trametes cingulata* glucoamylase disclosed as SEQ ID NO: 2 in WO 06/69289 (SEQ ID NO: 11 herein), and *Rhizomucor pusillus* alpha-amylase with *Aspergillus niger* glucoamylase linker and starch binding domain (SBD) disclosed in SEQ ID NO: 7 herein having the following substitutions G128D+D143N using SEQ ID NO: 7 for numbering (activity ratio in AGU:AGU:FAU-F is about 29:8:1).

Yeast: Ethanol Red®

The ability of trehalase to reduce trehalose was evaluated by running a saccharification and fermentation (SSF) using either Glucoamylase blend X alone or with the addition of either Ms or Tf trehalase. The Ms trehalase dose was set at 1 µg enzyme protein (EP) per gram of dry solids (DS) while three Tf trehalose doses were used for comparison (0.6, 0.7 and 0.8 ug EP/g DS). Glucoamylase blend X were dosed at 0.6 AGU/g DS and in according to the following calculation. Two plant mashes (corn starch liquefied using alpha-amylase BE369 or BE369 and protease PfuS) were used. Mash 1 represented BE369+PfuS and Mash 2 represented BE369 mash. For Mash 1 BE369 and PfuS were dosed at 2.3 µg EP/g DS and 2.6 µg EP/g DS, respectively. For Mash 2 BE369 dose was 2.81 µg EP/g DS. The urea dose for Mash 1 and Mash 2 were 400 ppm and 1000 ppm, respectively.

$$Enz.\ dose\ (uL) = \frac{Total\ GA\ dose\ \left(\frac{AGU}{gDS}\right) \times Mass\ Weight\ (g) \times Dry\ solid\ content\ (\%\ DS) \times 1000}{Stock\ enzyme\ conc.\ \left(\frac{AGU}{mL}\right)}$$

TABLE 2

Enzyme treatment in SSF of two industrial plant mashes

| Glucoamylase | Trehalase treatment | Trehalase Dose (ug EP/g DS) |
|---|---|---|
| Blend X | None | 0 |
| Blend X | Ms-trehalase | 1 |
| Blend X | Tf-trehalase | 0.6 |
| Blend X | Tf-trehalase | 0.7 |
| Blend X | Tf-trehalase | 0.8 |

The blends were evaluated in an SSF using two liquefied industrial plant corn mashes Mash 1 and Mash 2. The mashes were supplemented with 3 ppm penicillin. The amount of urea added to Mash 1 and Mash 2 were 400 ppm and 1000 ppm, respectively. The pH of both plant mashes was adjusted to pH 5.1 using 40% $H_2SO_4$ prior to dispensing mash into flasks. Approximately 60 g (55±0.03) of mash was added into each 125 mL and they were run in duplicates. Corning Disposable Erlenmeyer flask that had a 0.048" hole on the cap for venting. Each flask was dosed with enzymes according to Table 2 and 1.2 mL of rehydrated Ethanol Red yeast. Ethanol red was rehydrated by resuspending 5.5 g yeast with 100 mL tap water and incubated at 32° C. for 30-40 min. Flasks were incubated for the total of 52 hr at 32° C. while shaking at 120 rpm. Samples were collected at 52 hrs. Collected samples were prepared for HPLC by removing approximately 4 grams of fermentation sample and mixed it with 40 uL of 40% $H_2SO_4$. The mixture was centrifuged for 10 minutes at 3500×g, and the supernatant was filtered through 0.2 µM Whatman nylon filter. Filtered samples were analyzed on an Agilent HPLC 1100/1200 series with Chemstation software. Samples were separated on Bio-Rad HPX-87H Ion Exclusion column (300 mm×7.8 mm) with a cation H guard cartridge. The mobile phase, 5 mM $H_2SO_4$, was run at 0.8 ml/min at 65° C. and the RI detector temperature was set at 55° C. The method quantifies several analytes using calibration standards (4 point calibration with forced through zero) for dextrins (DP4+), maltotriose (DP3), maltose (DP2), glucose (DP1), fructose, acetic acid, lactic acid, glycerol and ethanol. HPLC results on ethanol, DP2 (maltose) are shown in Table 3. DP2 was analyzed since this sugar also contain the trehalose. In addition to the HPLC analysis, filtered samples of only Mash 1 were also analyzed on a Dionex ICS-3000 ion chromatography (IC) using Chromeleon 5 software to separate trehalose from other DP2 sugars (such as isomaltose, maltose and cellobiose). Samples were separated using the Carbopack PA1 column. The mobile phase were water, 0.2 M NaOH, 1 M sodium acetate and the flowrate was 1 mL/min and both the column and detector (PAD detector with disposable gold electrode) were at 30° C. The IC was run for 65 minutes and the trehalose level were reported in Table 4. Tf-trehalase has slightly better performance than Ms-trehalase since 0.6-0.8 ug EP of Tf had similar level of DP2 following SSF for 52 hrs. Without any trehalase addition, there were significant amount of DP2 left at the end of fermentation. The ethanol levels were compared between Ms and Tf-trehalase treatment in both plant mashes and there was no statistical significance between them. Therefore, Tf-trehalase, at 20% to 40% lower protein dose relative to Ms-trehalase, has similar application performance as Ms-trehalase in SSF using two different types of plant mash.

TABLE 3

Ethanol, and DP2 levels following SSF in two plant mashes for 52 Hrs

| Glucoamylase | Trehalase | Trehalase dose (µg EP/g DS) | Average ethanol level (% w/v) | | Average DP2 level (% w/v) | |
|---|---|---|---|---|---|---|
| | | | Mash 1 | Mash 2 | Mash 1 | Mash 2 |
| Blend X | None | | 13.517 | 13.0545 | 0.2405 | 0.1785 |
| | Ms-trehalase | 1 | 13.590 | 13.080 | 0.141 | 0.110 |
| | Tf-trehalase | 0.6 | 13.622 | 13.101 | 0.140 | 0.109 |
| | Tf-trehalase | 0.7 | 13.608 | 13.122 | 0.139 | 0.106 |
| | Tf-trehalase | 0.8 | 13.612 | 13.151 | 0.141 | 0.111 |

TABLE 4

Trehalose levels following SSF in two plant mashes for 52 Hrs

| Glucoamylase | Trehalase | Trehalase dose (µg EP/g DS) | Average trehalose level (% w/v) | |
|---|---|---|---|---|
| | | | Mash 1 | Mash 2 |
| Blend X | None | | 0.0661 | n/a |
| | Ms-trehalase | 1 | 0.0134 | n/a |
| | Tf-trehalase | 0.6 | 0.0150 | n/a |

TABLE 4-continued

Trehalose levels following SSF in two plant mashes for 52 Hrs

| Glucoamylase | Trehalase | Trehalase dose (μg EP/g DS) | Average trehalose level (% w/v) | |
|---|---|---|---|---|
| | | | Mash 1 | Mash 2 |
| | Tf-trehalase | 0.7 | 0.0147 | n/a |
| | Tf-trehalase | 0.8 | 0.0151 | n/a |

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. A process of producing ethanol, comprising
   (a) liquefying a starch-containing material with an alpha-amylase to form a liquefied material;
   (b) saccharifying the liquefied material;
   (c) fermenting using a fermentation organism;
   wherein a glucoamylase and a polypeptide having trehalase activity and at least 75% sequence identity to the mature polypeptide of SEQ ID NO: 23 are present and/or added during saccharification step (b) or fermentation step (c) and wherein sequence identity is determined using the Needleman-Wunsch algorithm as implemented in the Needle program of the EMBOSS package, version 5.0.0, using a gap open penalty of 10, a gap extension penalty of 0.5, and EBLOSUM62 substitution matrix.

2. The process of claim 1, wherein the polypeptide having trehalase activity has at least 80% sequence identity to the mature polypeptide of SEQ ID NO: 23.

3. The process of claim 1, wherein the polypeptide having trehalase activity has at least 85% sequence identity to the mature polypeptide of SEQ ID NO: 23.

4. The process of claim 1, wherein the polypeptide having trehalase activity and has at least 90% sequence identity to the mature polypeptide of SEQ ID NO: 23.

5. The process of claim 1, wherein the polypeptide having trehalase activity has at least 95% sequence identity to the mature polypeptide of SEQ ID NO: 23.

6. The process of claim 1, wherein saccharification step (b) and fermentation step (c) are simultaneous.

7. The process of claim 1, wherein the glucoamylase and the polypeptide having trehalase activity are present and/or added during saccharification step (b).

8. The process of claim 1, wherein the glucoamylase and the polypeptide having trehalase activity are present and/or added during fermentation step (c).

9. The process of claim 1, further comprising pre-saccharifying the liquefied material before step (b).

10. The process of claim 1, wherein an alpha-amylase is present and/or added during saccharification step (b) or fermentation step (c).

11. The process of claim 10, wherein the alpha-amylase is an alpha-amylase variant having at least 60% identity but less than 100% identity to the polypeptide of SEQ ID NO: 7 and one or more of the following substitutions: G128D, D143N, or G128D+D143N (using SEQ ID NO: 7 for numbering).

12. The process of claim 1, wherein the fermenting organism is a *Saccharomyces* strain.

* * * * *

```
                        SEQUENCE LISTING

Sequence total quantity: 35
SEQ ID NO: 1            moltype = AA  length = 694
FEATURE                 Location/Qualifiers
source                  1..694
                        mol_type = protein
                        organism = Myceliophthora sepedonium
SEQUENCE: 1
MALRHIAAAA IAGLASRTAA LYINGSVTAP CDSPIYCQGE LLKAVELARP FVDSKTFVDM    60
PTIKPVDEVL AAFSKLSLPL SNNSELNAFL YENFAQAGHE LEEVPDSELE TDAKFLDKLE   120
DRTIKEFVGK VIDIWPDLTR RYAGPSNCTE CANSFIPVNR TFVVAGGRFR EPYYWDSYWI   180
VEGLLRTGGA FTHISKNIIE NFLDFVDTIG FIPNGARIYY LNRSQPPLLT LMVKSYVDYT   240
NDTSILDRAL PLLIKEHEFF MNNRTVSITG SNGKEYTLNR YHVENNQPRP ESFREDYITA   300
NNGSYYASSG IIYPVKTPLN ETEKAALYSN LATGAESGWD YTSRWLGVPS DAARDVYFPL   360
RSLNVRDIVP VDLNSILYQN EVIIAEYLEK AGNSSAAKRF ATAAEQRSEA MYSLMWNATH   420
WSYFDYNLTD NTQHIFVPAD EDTAPQDRIE APPGQQVFFH IAQLYPFWTG AAPASLKANP   480
LAVQQAYARV ARMLDIKKGA IPATNYRTGQ QWDQPNVWPP LQHILMKGLL NTPATFGKSD   540
PAYQSVQNLA LRLAQRYLDS TFCTWYATGG STSDFPQLEG VTPGATGVMF EKYADNATNV   600
AGGGGEYEVV EGFGWTNGVL IWAADVFGNK LKRPDCGNIT AAHTHSSAKR GLEENKLPRR   660
AVELDPWDAA WTKMFGRSKL RRREAEDVRK RWMS                              694

SEQ ID NO: 2            moltype = AA  length = 1079
FEATURE                 Location/Qualifiers
source                  1..1079
                        mol_type = protein
                        organism = Trichoderma reesei
SEQUENCE: 2
MRSTVTSAAA LLSLLQLVSP VHGTTLVDRV TKCLSRHDGS DAESHFSKNV YKTDFAGVTW    60
DEDNWLLSTT QLKQGAFEAR GSVANGYLGI NVASVGPFFE VDTEEDGDVI SGWPLFSRRQ   120
SFATVAGFWD AQPQMNGTNF PWLSQYGSDT AISGIPHWSG LVLDLGGGTY LDATVSNKTI   180
SHFRSTYDYK AGVLSWSYKW TPKGNKGSFD ISYRLFANKL HVNQAVVDMQ VTASKNVQAS   240
IVNVLDGFAA VRTDFVESGE DGSAIFAAVR PNGVANVTAY VYADITGSGG VNLSSRKIVH   300
NKPYVHANAS SIAQAVPVKF AAGRTVRVTK FVGAASSDAF KNPKQVAKKA AAAGLSNGYT   360
KSLKAHVEEW ATVMPESSVD SFADPKTGKL PADSHIVDSA IIAVTNTYYL LQNTVGKNGI   420
KAVDGAPVNV DSISVGGLTS DSYAGQIFWD ADLWMQPGLV AAHPEAAERI TNYRLARYGQ   480
AKENVKTAYA GSQNETFFSA SAAVFPWTSG RYGNCTATGP CWDYEYHLNG DIGISLVNQW   540
VVNGDTKDFE KNLFPVYDSV AQLYGNLLRP NKTSWTLTNM TDPDEYANHV DAGGYTMPLI   600
AETLQKANSF RQQFGIEQNK TWNDMASNVL VLRENGVTLE FTAMNGTAVV KQADVIMLTY   660
PLSYGTNYSA QDALNDLDYY ANKQSPDGPA MTYAFFSIVA NEISPSGCSA YTYAQNAFKP   720
YVRAPFYQIS EQLIDDASVN GGTHPAYPFL TGHGGAHQVV LFGYLGLRLV PDDVIHIEPN   780
LPPQIPYLRY RTFYWRGWPI SAWSNYTHTT LSRAAGVAAL EGADQRFARK PITIHAGPEQ   840
DPTAYRLPVK GSVVIPNKQI GSQQTYAGNL VQCHAASSPN DYVPGQFPIA AVDGATSTKW   900
QPASADKVSS ITVSLDKEDV GSLVSGFHFD WAQAPPVNAT VIFHDEALAD PATALASAHK   960
HNSKYTTVTS LTNIELSDPY VSTKDLNAIA IPIGNTTNVT LSHPVAASRY ASLLIVGNQG  1020
LDPVDVKAKN GTGATVAEWA IFGHGKEHSG KPSSHSKRRL NVRTAATLSN PRSFMRRRL   1079

SEQ ID NO: 3            moltype = AA  length = 1072
FEATURE                 Location/Qualifiers
source                  1..1072
                        mol_type = protein
                        organism = Aspergillus niger
SEQUENCE: 3
MQVKFLATLL PLLLHLPAAV DGLPGKNARI SASLKRHAGR DVPQTALNST NVYQTKFSGV    60
TWDEDHWLLT TTTPDQGHYQ SRGSVANGYL GINVANIGPF FELDEPVNGD VINGWPLYSR   120
RQSFATISGF WDRQAHTNGS NFPWLSQYGD DSVISGVPHW SGLILDLGDD TYLDATVDNR   180
TISNPKSTYD FKSGVLSWSY TWTPQGNKGS YAITYRLFAH KLYVNRAVVD MEITPLTNGN   240
ATVVNVLDGY AAVRTDFVAS GQEEGAIFSA VRPWGVNNVT AYVYATLDGS DSVDLSSRRI   300
VTDKPYVSTN SSSVAQAVDV MFTANETVRI TKFVGGATTD YFLATQETAK AACLAGLADG   360
YVKSLQSHVG EWATIMHDHS VDRFTDPATG KLPEDSHIVD SAIIAVTNTY YLLQNTAGTN   420
AIVAAGGIPV NVDSCAPGGL TSDSYGGQIF WDADLWMQPG LVASHPESAQ RFTNYRIALH   480
YQAQANIETA FTGSKNQTSF SSSAAIYPWT SGRFGNCTAT GPCWDYQYHL NGDIGLAMIN   540
QWVASGDTAW FKNYLFPIYD AAATLYSELV ERNGSSWTLT NMTDPDEYAN SINAGGYTMP   600
LIAETLQNAN KLRKQFGLEP NETWDEIAED VLILRENGVT LEYTSMNGSA VVKQADIVLN   660
TFPLTYESDN YTATNSLTDL DYYANKQSAD GPAMTYAIFA IVASDVSPSG CSAFTYHQYS   720
```

```
YAPYARGPWY QLSEQMIDDA SINGGTHPAF PPFLTGHGGAN QVALYGYLGL RLHPDDTIYI  780
DPNLPPQIPH ITYRTFYWHG WPISAWSNYT HTTIQRDSSL APLASADLLF SNVSIKVQVG  840
QSTASADEAT IYYLPLSGAL TVPNRMIGSV NTTPGNQVQC HPVYSPDAYE PGQFPISAVD  900
GATSTKWQPS TSDLTSLTVT LSTTAEAGAE EVSGFYFDWS QAPPENLTVI FHDSPIGNPS  960
TVFAAAGSNS TGYRVITSMS NIVQSKPYNA ISAEELNVVS IPTANTTTIT LDAPVQKARY 1020
ATLLIAGNQA NETAGATVAE WVILGQNSTS SSSAQAKRKM SARSKATLAQ LS         1072

SEQ ID NO: 4              moltype = AA  length = 598
FEATURE                   Location/Qualifiers
source                    1..598
                          mol_type = protein
                          organism = Talaromyces emersonii
SEQUENCE: 4
RAPVAARATG SLDSFLATET PIALQGVLNN IGPNGADVAG ASAGIVVASP SRSDPNYFYS  60
WTRDAALTAK YLVDAFIAGN KDLEQTIQQY ISAQAKVQTI SNPSGDLSTG GLGEPKFNVN 120
ETAFTGPWGR PQRDGPALRA TALIAYANYL IDNGEASTAD EIIWPIVQND LSYITQYWNS 180
STFDLWEEVE GSSFFTTAVQ HRALVEGNAL ATRLNHTCSN CVSQAPQVLC FLQSYWTGSY 240
VLANFGGSGR SGKDVNSILG SIHTFDPAGG CDDSTFQPCS ARALANHKVV TDSFRSIYAI 300
NSGIAEGSAV AVGRYPEDVY QGGNPWYLAT AAAAEQLYDA IYQWKKIGSI SITDVSLPFF 360
QDIYPSAAVG TYNSGSTTFN DIISAVQTYG DGYLSIVEKY TPSDGSLTEQ FSRTDGTPLS 420
ASALTWSYAS LLTASARRQS VVPASWGESS ASSVPAVCSA TSATGPYSTA TNTVWPSSGS 480
GSSTTTSSAP CTTPTSVAVT FDEIVSTSYG ETIYLAGSIP ELGNWSTASA IPLRADAYTN 540
SNPLWYVTVN LPPGTSFEYK FFKNQTDGTI VWEDDPNRSY TVPAYCGQTT AILDDSWQ   598

SEQ ID NO: 5              moltype = AA  length = 556
FEATURE                   Location/Qualifiers
source                    1..556
                          mol_type = protein
                          organism = Gloeophyllum sepiarium
SEQUENCE: 5
QSVDSYVSSE GPIAKAGVLA NIGPNGSKAS GASAGVVVAS PSTSDPDYWY TWTRDSSLVF  60
KSLIDQYTTG IDSTSSLRTL IDDFVTAEAN LQQVSNPSGT LTTGGLGEPK FNVDETAFTG 120
AWGRPQRDGP ALRSTALITY GNWLLSNGNT SYVTSNLWPI IQNDLGYVVS YWNQSTYDLW 180
EEVDSSSFFT TAVQHRALRE GAAFATAIGQ TSQVSSYTTQ ADNLLCFLQS YWNPSGGYIT 240
ANTGGGRSGK DANTLLASIH TYDPSAGCDA ATFQPCSDKA LSNLKVYVDS FRSVYSINSG 300
VASNAAVATG RYPEDSYQGG NPWYLTTFAV AEQLYDALNV WESQGSLEVT STSLAFFQQF 360
SSGVTAGTYS SSSSTYSTLT SAIKNFADGF VAINAKYTPS NGGLAEQYSK SDGSPLSAVD 420
LTWSYASALT AFEARNNTQF AGWGAAGLTV PSSCSGNSGG PTVAVTFNVN AETVWGENIY 480
LTGSVDALEN WSADNALLLS SANYPTWSIT VNLPASTAIE YKYIRKNNGA VTWESDPNNS 540
ITTPASGSTT ENDTWR                                                556

SEQ ID NO: 6              moltype = AA  length = 559
FEATURE                   Location/Qualifiers
source                    1..559
                          mol_type = protein
                          organism = Gloephyllum trabeum
SEQUENCE: 6
QSVDSYVGSE GPIAKAGVLA NIGPNGSKAS GAAAGVVVAS PSKSDPDYWY TWTRDSSLVF  60
KSLIDQYTTG IDSTSSLRSL IDSFVIAEAN IQQVSNPSGT LTTGGLGEPK FNVDETAFTG 120
AWGRPQRDGP ALRATALITY GNWLLSNGNT TWVTSTLWPI IQNDLNYVVQ YWNQTTFDLW 180
EEVNSSSFFT TAVQHRALRE GAAFATKIGQ TSSVSSYTTQ AANNLLCFLQ SYWNPTSGYH 240
ANTGGGRSGK DANTLLASIH TYDPSAGCDA TTFQPCSDKA LSNLKVYVDS FRSVYSINSG 300
IASNAAVATG RYPEDSYQGG NPWYLTTFAV AEQLYDALNV WAAQGSLNVT SISLPFFQQF 360
SSSVTAGTYA SSSTTYTTLT SAIKSFADGF VAINAQYTPS NGGLAEQFSR SNGAPVSAVD 420
LTWSYASALT AFEARNNTQF AGWGAVGLTV PTSCSSNSGG GGGSTVAVTF NVNAQTVWGE 480
NIYITGSVDA LSNWSPDNAL LLSSANYPTW SITVNLPAST AIQYKYIRKN NGAVTWESDP 540
NNSITTPASG SVTENDTWR                                             559

SEQ ID NO: 7              moltype = AA  length = 583
FEATURE                   Location/Qualifiers
source                    1..583
                          mol_type = protein
                          organism = Rhizomucor pusillus
SEQUENCE: 7
ATSDDWKGKA IYQLLTDRFG RADDSTSNCS NLSNYCGGTY EGITKHLDYI SGMGFDAIWI  60
SPIPKNSDGG YHGYWATDFY QLNSNFGDES QLKALIQAAH ERDMYVMLDV VANHAGPTSN 120
GYSGYTFGDA SLYHPKCTID YNDQTSIEQC WVADELPDID TENSDNVAIL NDIVSGWVGN 180
YSFDGIRIDT VKHIRKDFWT GYAEAAGVFA TGEVFNGDPA YVGPYQKYLP SLINYPMYYA 240
LNDVFVSKSK GFSRISEMLG SNRNAFEDTS VLTTFVDNHD NPRFLNSQSD KALFKNALTY 300
VLLGEGIPIV YYGSEQGFSG GADPANREVL WTTNYDTSSD LYQFIKTVNS VRMKSNKAVY 360
MDIYVGDNAY AFKHGDALVV LNNYGSGSTN QVSFSVSGKF DSGASLMDIV SNITTTVSSD 420
GTVTFNLKDG LPAIFTSATG GTTTTATPTG SGSVSTSKT TATASKTSTS TSSTSCTTPT 480
AVAVTFDLTA TTTYGENIYL VGSISQLGDW ETSDGIALSA DKYTSSDPLW YVTVTLPAGE 540
SFEYKFIRIE SDDSVEWESD PNREYTVPQA CGTSTATVTD TWR                  583

SEQ ID NO: 8              moltype = AA  length = 515
FEATURE                   Location/Qualifiers
source                    1..515
                          mol_type = protein
```

```
                        organism = Bacillus stearothermophilus
SEQUENCE: 8
AAPFNGTMMQ YFEWYLPDDG TLWTKVANEA NNLSSLGITA LWLPPAYKGT SRSDVGYGVY    60
DLYDLGEFNQ KGTVRTKYGT KAQYLQAIQA AHAAGMQVYA DVVFDHKGGA DGTEWVDAVE   120
VNPSDRNQEI SGTYQIQAWT KFDFPGRGNT YSSFKWRWYH FDGVDWDESR KLSRIYKFRG   180
IGKAWDWEVD TENGNYDYLM YADLDMDHPE VVTELKNWGK WYVNTTNIDG FRLDAVKHIK   240
FSFFPDWLSY VRSQTGKPLF TVGEYWSYDI NKLHNYITKT NGTMSLFDAP LHNKFYTASK   300
SGGAFDMRTL MTNTLMKDQP TLAVTFVDNH DTEPGQALQS WVDPWFKPLA YAFILTRQEG   360
YPCVFYGDYY GIPQYNIPSL KSKIDPLLIA RRDYAYGTQH DYLDHSDIIG WTREGVTEKP   420
GSGLAALITD GPGGSKWMYV GKQHAGKVFY DLTGNRSDTV TINSDGWGEF KVNGGSVSVW   480
VPRKTTVSTI ARPITTRPWT GEFVRWTEPR LVAWP                              515

SEQ ID NO: 9               moltype = AA  length = 413
FEATURE                    Location/Qualifiers
source                     1..413
                           mol_type = protein
                           organism = Pyrococcus furiosus
SEQUENCE: 9
AELEGLDESA AQVMATYVWN LGYDGSGITI GIIDTGIDAS HPDLQGKVIG WVDFVNGRSY    60
PYDDHGHGTH VASIAAGTGA ASNGKYKGMA PGAKLAGIKV LGADSGSGIS TIIKGVEWAV   120
DNKDKYGIKV INLSLGSSQS SDGTDALSQA VNAAWDAGLV VVVAAGNSGP NKYTIGSPAA   180
ASKVITVGAV DKYDVITSFS SRGPTADGRL KPEVVAGNWK IIAARASGTS MGQPINDYYT   240
AAPGTSMATP HVAGIAALLL QAHPSWTPDK VKTALIETAD IVKPDEIADI AYGAGRVNAY   300
KAINYDNYAK LVFTGYVANK GSQTHQFVIS GASFVTATLY WDNANSDLDL YLYDPNGNQV   360
DYSYTAYYDF EKVGYYNPTD GTWTIKVVSY SGSANYQVDV VSDGSLSQPG SSP          413

SEQ ID NO: 10              moltype = AA  length = 595
FEATURE                    Location/Qualifiers
source                     1..595
                           mol_type = protein
                           organism = Penicillium oxalicum
SEQUENCE: 10
RPDPKGGNLT PFIHKEGERS LQGILDNLGG RGKKTPGTAA GLFIASPNTE NPNYYYTWTR    60
DSALTAKCLI DLFEDSRAKF PIDRKYLETG IRDYKSSQAI LQSVSNPSGT LKDGSGLGEP   120
KFEIDLNPFS GAWGRPQRDG PALRATAMIT YANYLISHGQ KSDVSQVMWP IIANDLAYVG   180
QYWNNTGFDL WEEVDGSSFF TIAVQHRALV EGSQLAKKLG KSCDACDSQP PQILCFLQSF   240
WNGKYITSNI NTQASRSGID LDSVLGSIHT FDPEAACDDA TFQPCSARAL ANHKVYVDSF   300
RSIYKINAGL AEGSAANVGR YPEDVYQGGN PWYLATLGAS ELLYDALYQW DRLGKLEVSE   360
TSLSFFKDFD ATVKIGSYSR NSKTYKKLTQ SIKSYADGFI QLVQQYTPSN GSLAEQYDRN   420
TAAPLSANDL TWSFASFLTA TQRRDAVVPP SWGAKSANKV PTTCSASPVV GTYKAPTATF   480
SSKTKCVPAK DIVPITFYLI ENTYYGENVF MSGNITALGN WDAKKGFPLT ANLYTQDQNL   540
WFASVEFIPA GTPFEYKYYK VEPNGDITWE KGPNRVFVAP TGCPVQPHSN DVWQF        595

SEQ ID NO: 11              moltype = AA  length = 556
FEATURE                    Location/Qualifiers
source                     1..556
                           mol_type = protein
                           organism = Trametes cingulata
SEQUENCE: 11
QSSAADAYVA SESPIAKAGV LANIGPSGSK SNGAKAGIVI ASPSTSNPNY LYTWTRDSSL    60
VFKALIDQFT TGEDTSLRTL IDEFTSAEAI LQQVPNPSGT VSTGGLGEPK FNIDETAFTD   120
AWGRPQRDGP ALRATAIITY ANWLLDNKNT TYVTNTLWPI IKLDLDYVAS NWNQSTFDLW   180
EEINSSSFFT TAVQHRALRE GATFANRIGQ TSVVSGYTTQ ANNLLCFLQS YWNPTGYIT    240
ANTGGGRSGK DANTVLTSIH TFDPAAGCDA VTFQPCSDKA LSNLKVYVDA FRSIYSINSG   300
IASNAAVATG RYPEDSYMGG NPWYLTTSAV AEQLYDALVI VWNKLGALNVT STSLPFFQQF   360
SSGVTVGTYA SSSSTFKTLT SAIKTFADGF LAVNAKYTPS NGGLAEQYSR SNGSPVSAVD   420
LTWSYAAALT SFAARSGKTY ASWGAAGLTV PTTCSGSGGA GTVAVTFNVQ ATTVFGENIY   480
ITGSVPALQN WSPDNALILS AANYPTWSIT VNLPASTTIE YKYIRKFNGA VTWESDPNNS   540
ITTPASGTFT QNDTWR                                                   556

SEQ ID NO: 12              moltype = AA  length = 555
FEATURE                    Location/Qualifiers
source                     1..555
                           mol_type = protein
                           organism = Pycnoporus sanguineus
SEQUENCE: 12
QSSAVDAYVA SESPIAKQGV LNNIGPNGSK AHGAKAGIVV ASPSTENPDY LYTWTRDSSL    60
VFKLLIDQFT SGDDTSLRGL IDDFTSAEAI LQQVSNPSGT VSTGGLGEPK FNIDETAFTG   120
AWGRPQRDGP ALRATSIIRY ANWLLDNGNT TYVSNTLWPV IQLDLDYVAD NWNQSTFDLW   180
EEVDSSSFFT TAVQHRALRE GATFASRIGQ SSVVSGYTTQ ADNLLCFLQS YWNPSGGYVT   240
ANTGGGRSGK DSNTVLTSIH TFDPAAGCDA ATFQPCSDKA LSNLKVYVDA FRSIYTINNG   300
IASNAAVATG RYPEDSYMGG NPWYLTTSAV AEQLYDALYV WDQLGGLNVT STSLAFFQQF   360
ASGLSTGTYS ASSSTYATLT SAIRSFADGF LAINAKYTPA DGGLAEQYSR NDGTPLSAVD   420
LTWSYAAALT AFAAREGKTY GSWGAAGLTV PASCSGGGGA TVAVTFNVQA TTVFGENIYI   480
TGSVAALQNW SPDNALILSA ANYPTWSITV NLPANTVVQY KYIRKFNGQV TWESDPNNQI   540
TTPSGGSFTQ NDVWR                                                    555

SEQ ID NO: 13              moltype = AA  length = 177
FEATURE                    Location/Qualifiers
```

```
source                   1..177
                         mol_type = protein
                         organism = Thermoascus aurantiacus
SEQUENCE: 13
TRISSCSGSR QSALTTALRN AASLANAAAD AAQSGSASKF SEYFKTTSSS TRQTVAARLR     60
AVAREASSSS SGATTYYCDD PYGYCSSNVL AYTLPSYNII ANCDIFYTYL PALTSTCHAQ    120
DQATTALHEF THAPGVYSPG TDDLAYGYQA AMGLSSSQAV MNADTYALYA NAIYLGC       177

SEQ ID NO: 14            moltype = AA  length = 844
FEATURE                  Location/Qualifiers
source                   1..844
                         mol_type = protein
                         organism = Aspergillus fumigatus
SEQUENCE: 14
QELAFSPPFY PSPWADGQGE WADAHRRAVE IVSQMTLAEK VNLTTGTGWE MDRCVGQTGS     60
VPRLGINWGL CGQDSPLGIR FSDLNSAFPA GTNVAATWDK TLAYLRGKAM GEEFNDKGVD    120
ILLGPAAGPL GKYPDGGRIW EGFSPDPVLT GVLFAETIKG IQDAGVIATA KHYILNEQEH    180
FRQVGEAQGY GYNITETISS NVDDKTMHEL YLWPFADAVR AGVGAVMCSY NQINNSYGCQ    240
NSQTLNKLLK AELGFQGFVM SDWSAHHSGV GAALAGLDMS MPGDISFDDG LSFWGTNLTV    300
SVLNGTVPAW RVDDMAVRIM TAYYKVGRDR LRIPPNFSSW TRDEYGWEHS AVSEGAWTKV    360
NDFVNVQRSH SQIIREIGAA STVLLKNTGA LPLTGKEVKV GVLGEDAGSN PWGANGCPDR    420
GCDNGTLAMA WGSGTANFPY LVTPEQAIQR EVISNGGNVF AVTDNGALSQ MADVASQSSV    480
SLVFVNADSG EGFISVDGNE GDRKNLTLWK NGEAVIDTVV SHCNNTIVVI HSVGPVLIDR    540
WYDNPVTAI IWAGLPGQES GNSLVDVLYG RVNPSAKTPF TWGKTRESYG APLLTEPNNG     600
NGAPQDDFNE GVFIDYRHFD KRNETPIYEF GHGLSYTTFG YSHLRVQALN SSSSAYVPTS    660
GETKPAPTYG EIGSAADYLY PEGLKRITKF IYPWLNSTDL EDSSDDPNYG WEDSEYIPEG    720
ARDGSPQPLL KAGGAPGGNP TLYQDLVRVS ATITNTGNVA GYEVPQLYVS LGGPNEPRVV    780
LRKFDRIFLA PGEQKVWTTT LNRRDLANWD VEAQDWVITK YPKKVHVGSS SRKLPLRAPL    840
PRVY                                                                  844

SEQ ID NO: 15            moltype = AA  length = 227
FEATURE                  Location/Qualifiers
source                   1..227
                         mol_type = protein
                         organism = Thermoascus aurantiacus
SEQUENCE: 15
FVQNIVIDGK KYYGGYLVNQ YPYMSNPPEV IAWSTTATDL GFVDGTGYQT PDIICHRGAK     60
PGALTAPVSP GGTVELQWTP WPDSHHGPVI NYLAPCNGNV STVDKTQLEF FKIAESGLIN    120
DDNPPGIWAS DNLIAANNSW TVTIPTTIAP GNYVLRHEII ALHSAQNYDG AQNYPQCINL    180
QVTGGGSDNP AGTLGTALYH DTDPGILINI YQKLSSYIIP GPPLYTG                  227

SEQ ID NO: 16            moltype = AA  length = 228
FEATURE                  Location/Qualifiers
source                   1..228
                         mol_type = protein
                         organism = Penicillium emersonii
SEQUENCE: 16
HGFVQGIVIG DQFYSGYIVN SFPYESNPPP VIGWATTATD LGFVDGTGYQ GPDIICHRNA     60
TPAPLTAPVA AGGTVELQWT PWPDSHHGPV ITYLAPCNGN CSTVDKTTLE FFKIDQQGLI    120
DDTSPPGTWA SDNLIANNNS WTVTIPNSVA PGNYVLRHEI IALHSANNKD GAQNYPQCIN    180
IEVTGGGSDA PEGTLGEDLY HDTDPGILVD IYEPIATYTI PGPPEPTF                 228

SEQ ID NO: 17            moltype = AA  length = 506
FEATURE                  Location/Qualifiers
source                   1..506
                         mol_type = protein
                         organism = Aspergillus fumigatus
SEQUENCE: 17
QQVGTSQAEV HPSMTWQSCT AGGSCTTNNG KVVIDANWRW VHKVGDYTNC YTGNTWDTTI     60
CPDDATCASN CALEGANYES TYGVTASGNS LRLNFVTTSQ QKNIGSRLYM KDDSTYEMF     120
KLLNQEFTFD VDVSNLPCGL NGALYFVAMD ADGGMSKYPT NKAGAKYGTG YCDSQCPRDL    180
KFINGQANVE GWQPSSNDAN AGTGNHGSCC AEMDIWEANS ISTAFTPHPC DTPGQVMCTG    240
DACGGTYSSD RYGGTCDPDG CDFNSFRQGN KTFYGPGMTV DTKSKFTVVT QFITDDGTSS    300
GTLKEIKRFY VQNGKVIPNS ESTWTGVSGN SITTEYCTAQ KSLFQDQNVF EKHGGLEGMG    360
AALAQGMVLV MSLWDDHSAN MLWLDSNYPT TASSTTPGVA RGTCDISSGV PADVEANHPD    420
AYVVYSNIKV GPIGSTFNSG GSNPGGGTTT TTTTQPTTTT TTAGNPGGTG VAQHYGQCGG    480
IGWTGPTTCA SPYTCQKLND YYSQCL                                          506

SEQ ID NO: 18            moltype = AA  length = 435
FEATURE                  Location/Qualifiers
source                   1..435
                         mol_type = protein
                         organism = Aspergillus fumigatus
SEQUENCE: 18
QQTVWGQCGG QGWSGPTSCV AGAACSTLNP YYAQCIPGAT ATSTTLTTTT AATTTSQTTT     60
KPTTTGPTTS APTVTASGNP FSGYQLYANP YYSSEVHTLA MPSLPSSLQP KASAVAEVPS    120
FVWLDVAAKV PTMGTYLADI QAKNKAGANP PIAGIFVVYD LPDRDCAALA SNGEYSIANN    180
GVANYKAYID AIRAQLVKYS DVHTILVIEP DSLANLVTNL NVAKCANAQS AYLECVDYAL    240
KQLNLPNVAM YLDAGHAGWL GWPANLGPAA TLFAKVYTDA GSPAAVRGLA TNVANYNAWS    300
```

```
LSTCPSYTQG DPNCDEKKYI NAMAPLLKEA GFDAHFIMDT SRNGVQPTKQ NAWGDWCNVI    360
GTGFGVRPST NTGDPLQDAF VWIKPGGESD GTSNSTSPRY DAHCGYSDAL QPAPEAGTWF    420
QAYFEQLLTN ANPSF                                                    435

SEQ ID NO: 19          moltype = AA   length = 547
FEATURE                Location/Qualifiers
source                 1..547
                       mol_type = protein
                       organism = Meripilus giganteus
SEQUENCE: 19
TPTGRNLKLH EAREDLPAGF SLRGAASPDT TLKLRIALVQ NNFAELEDKL YDVSTPSSAN     60
YGNHLSKEEV EQYIAPAPES VKAVNAWLTE NGLDAHTISP AGDWLAFEVP VSKANELFDA    120
DFSVFTHDES GLEAIRTLAY SIPAELQGHL DLVHPTVTFP NPNAHLPVVR STQPIRNLTG    180
RAIPASCAST ITPACLQAIY GIPTTKATQS SNKLAVSGFI DQFANKADLK SFLAQFRKDI    240
SSSTTFSLQT LDGGENDQSP SEAGIEANLD IQYTVGLATG VPTTFISVGD DFQDGNLEGF    300
LDIINFLLGE SNPPQVLTTS YGQNENTISA KLANQLCNAY AQLGARGTSI LFASGDGGVS    360
GSQSAHCSNF VPTFPSGCPF MTSVGATQGV SPETAAAFSS GGFSNVFGIP SYQASAVSGY    420
LSALGSTNSG KFNRSGRGFP DVSTQGVDFQ IVSGGQTIGV DGTSCASPTF ASVISLVNDR    480
LIAAGKSPLG FLNPFLYSSA GKAALNDVTS GSNPGCSTNG FPAKAGWDPV TGLGTPNFAK    540
LLTAVGL                                                             547

SEQ ID NO: 20          moltype = DNA   length = 3164
FEATURE                Location/Qualifiers
source                 1..3164
                       mol_type = genomic DNA
                       organism = Talaromyces funiculosus
SEQUENCE: 20
atgtatagtg caacgctact tcaggccctg tgccttctgc ccttggccgc aggactcccg     60
ttcaacgagc gagtagatca agtcctccgc tcatatgagg tgacctcaaa actcgactcc    120
cgcagcacca aaccttcaaa acatggccac acctaccaga ctcaattcct cggcgtaacc    180
tgggaccaac gcaactggcg cctccaaagc accgtcctcg atcagggaca ttatgagtct    240
cgtggatcca ttgccaacgg ctacattggc ctaaacgtcg ccggtgctgg ccccttgttt    300
gagctggatt cccccgtcga tggcgatgta atcaatggct ggcctctgtt ttcgcgtcga    360
cagacgtttg ctgggttagc gggattttac gatttacagc ctagaactaa tggtacgaat    420
tttccgtggt tgtctcagta tggcgatgat agcgcaatta gcgtcgtgcc gcattgggat    480
gggatggtct tagatttggg tgacgagag tatctcgatg cgacggtgga caattccacc    540
atatcggatt atacgactac ttatgattat aaagcgggtg ttttgtcgtg ggattacaaa    600
tggaccccga aaaatgccaa tgggtcgttt ggaataagct acaagatctt tgcgaacaag    660
cttgatgtta atcaggctgt ggtgcaattg agcattactc cgtcgacgaa tgggtcagcg    720
tctgtggtga atgtgattga tggatatgcc gctgttcgga cggactttgt ctcatcgggg    780
aatgagagtg acgttgtcta caccgctgtc aaacctaatg gcgtgaccaa tgttaccgca    840
tggatctata ctgcgttgga tggagatgat gcttttgaca tttcttcggc ggctcttgtg    900
aacgataagc catacgtgca tcaaaatgac tcttcgatcg cgcagtctgt caatgttaca    960
ttcactgccg gtactaccat cacgatcaac aaatttgtcg cgcgctgcatc taccgatgca   1020
ttcccggacc ctcaaaagca cgccagagaa gctgccttgt ctgctcgtcg cagaggcttt   1080
gacgacctct tccgctctca catctccgaa tgggctcaag tcatgcccga cgactccgtc   1140
gacgtttca cactcgcaaa cggcactcta cccaatgaca cgttcatcat cgaatctgct   1200
gtaatgccg ttgtaaatcc ttactaccta ctacagaata cggttgggcc aaatgctctt   1260
cgtcgagtaa acaatgcccc ggtcaatgac tggagtatac ccgtcggcgg tctgacgtcg   1320
gattcttacg ctggacaaat cttctgggat gccgatgtct ggatgcagcc tggcctggtc   1380
gcagcattcc ctgaatctgc taagcgtatc actaattacc gagcagccaa atattccaa   1440
gccctggaaa atgcaaagac ggcatacact agttcccaga accagacgtg gttctcgccc   1500
gatgctgcaa tttactcatg gactagtgga agagtcggca actgtactgc acaggtccaa   1560
tgctgggatt atgaatatca cttgaacggc gacatcggaa tttcgcttgt caacgagtgg   1620
gttgtcagcg gtgataacga gactttcaag aacaagcatt tcccaattta caactccatt   1680
gcgacgttgt atggagactt gttgaaaaag aatggtagtt attacacact cactaacatg   1740
actgatcctg atgaatatgc aaacaatgtt gatgctggtg gatatacgat gacgctgatt   1800
tcgcagacgt tgtcgaatgc caacgcattc cggaaacagt ttggcatgaa cgagaacaca   1860
acctggacag agatggcaga caacattctc ttgattcgcg agaatgatgt aaccctgag   1920
tataacaacta tgaacaacag tgtgccgtc aaacaggccg atgtgattct gtccaccttc   1980
ccattggact ataccaaaaa ctacaccacc agcgctgctc tcaatgatct agattacgta   2040
tgttctccct atccagtcat tcaataacct gctaacattc acagtacgcg ctgaaacaat   2100
ctcctgacgg tcccggcatg acatacgcca tcttctccat cgttgccaac gacgtttccc   2160
catctggctg ctcagcatac acctatgcc aatattccta cgaccgtac atccgcggac   2220
catttttcca attctccgaa caactactag atgactatac tatcaatggc ggcacgcatc   2280
ccgccttccc cttttgact ggtcacggag gcgcaaacca ggtcgttctg tacgggtatc   2340
tgggtctgag gctgctaccg gacgatatgt tgcatatcga tcccaaccta ccgcctcaaa   2400
ttcccagcat taaatatcgc actttctact ggcgcggatg gcccatccaa gcagcctcaa   2460
attacacaca cactaccatt caacgcgcaa caacagtcgc gccattatca accgccgacc   2520
caacctacgc taataagagc atacatgtct cggtcggcca caacaccgtc aactccacaa   2580
cctattccct gtctgcgaac gggtctgcgc tcgttgtgcc taacagacaa atcggctcca   2640
tcaacactgt tgctggcaac gtggtgcagt gcaaatccgt tttgtcgaca gacgcatacc   2700
aaaagggca atacccatc tcggcggttg atggtgcagc gtcgacgaag tggcagcctg   2760
agtttgcgg gaacattagc tctttgcag tggtagcagt gttagtagtg   2820
tgtctgggtt ctattttgat tgggctcagg caccgcctac caatatcact gtactcctac   2880
acaactcgtc atctgcagca ctcgcttctt ctggcgacaa acctgaagc tcggcagtga   2940
cattgaatat aacaatctca aaccccctaca acgcatcaac ctacaacgcg aatatcatcg   3000
cattacccttc tagtaattcg acaaaactata cgttcccggc accggtacca aagccgaggt   3060
atgcaacctt gtttgtgcag gggaatcagg cgctggatga gacagataca aaatctggga   3120
```

-continued

```
atggtaccgg agcgacggtt gcggagtggg cgatattgag ttga           3164

SEQ ID NO: 21           moltype = AA   length = 1038
FEATURE                 Location/Qualifiers
source                  1..1038
                        mol_type = protein
                        organism = Talaromyces funiculosus
SEQUENCE: 21
MYSATLLQAL CLLPAAGLP FNERVDQVLR SYEVTSKLDS RSTKPSKHGH TYQTQFLGVT   60
WDQRNWRLQS TVLDQGHYES RGSIANGYIG LNVAGAPLF ELDSPVDGDV INGWPLFSRR  120
QTFAGLAGFY DLQPRTNGTN FPWLSQYGDD SAISGVPHWG GMVLDLGDGE YLDATVDNST  180
ISDYTTTYDY KAGVLSWDYK WTPKNANGSF GISYKIFANK LDVNQAVVQL SITPSTNGSA  240
SVVNVIDGYA AVRTDFVSSG NESDVVYTAV KPNGVTNVTA WIYTALDGDD AFDISSAALV  300
NDKPYVHQND SSIAQSVNVT FTAGTTITIN KFVGAASTDA FPDPQSTARE AALSARRRGF  360
DDLFRSHISE WAQVMPDDSV DDFTLANGTL PNDTFIIESA VMAVVNPYYL LQNTVGPNAL  420
RRVNNAPVND WSIPVGGLTS DSYAGQIFWD ADVWMQPGLV AAFPESAKRI TNYRAAKYSQ  480
ALENAKTAYT SSQNQTWFSP DAAIYSWTSG RVGNCTATGP CWDYEYHLNG DIGISLVNEW  540
VVSGDNETFK NKHFPIYNSI ATLYGDLLKK NGSYYTLTNM TDPDEYANNV DAGGYTMTLI  600
SQTLSNANAF RKQFGMNENT TWTEMADNIL LIRENDVTLE YTTMNNSVAV KQADVILSTF  660
PLDYTKNYTT SAALNDLDYY ALKQSPDGPG MTYAIFSIVA NDVSPSGCSA YTYAQYSYDP  720
YIRGPFFQFS EQLLDDYTIN GGTHPAFPFL TGHGGANQVV LYGYLGLRLL PDDMLHIDPN  780
LPPQIPSIKY RTFYWRGWPI QAASNYTHTT IQRATTVAPL STADPTYANK SIHVSVGHNT  840
VNSTTYSLSA NGSALVVPNR QIGSINTVAG NVVQCKSVLS TDAYQKGQYP ISAVDGAAST  900
KWQPEFAANI SSLTVDLTGS NVSSVSGFYF DWAQAPPTNI TVLLHNSSSA ALASSGDKPG  960
SSAVTLNITI SNPYNASTYN ANIIALPSSN STNYTFPAPV PKPRYATLFV QGNQALDETD 1020
TKSGNGTGAT VAEWAILS                                              1038

SEQ ID NO: 22           moltype = DNA   length = 3608
FEATURE                 Location/Qualifiers
source                  1..3608
                        mol_type = genomic DNA
                        organism = Talaromyces leycettanus
SEQUENCE: 22
atgcagtcaa agctcctggc tctgctgccg cttctgctgc aactccctgc agtaagcggc   60
acgtctgcca acgcgcgcat caacagatgc gtcaagaaac acgcaggtgg gaaaacccca  120
agtggcccat ccaacaacac ctatcaaacc agattcccg gagtcacctg ggaccaggac  180
aactggtgcc tctccacgac caccctggac cagggtcact acgaatcgcg cggctccgtc  240
gccaatgggt acttgggtat taatgttgcc agcgttggcc cgttcttcga atttgacaca  300
cccgtcgatg gcgacgtgat caatggctgg cctttgttcg accggcgcat gtccttttgca  360
accatcagtg gcttctggga ccagcagccc acgacgaatg gatccaactt cccctggctg  420
tatcagtacg gtggtgagag cgtcatcagc ggtgtgcctc actggagcgg cctgattctc  480
gatctgggcg acaacaccta cttggacgcg acggtggaca gccgcaccat tcgggcttc  540
agcacgacgt atgacttcaa gtcgggtgtt ctgtcctggt cctatcagtg gactcccgcc  600
ggaaacatgg gctcctacaa catcacgtac cgtctctttg cgcacaagct gtacgtcaac  660
caggccgtcg tggacatgga ggttgtctcc tcgacggaag caaaggccac cgtcgtgaac  720
gtgattgatg gtgcctcggc tgtccgcacg gattttgtgg aatccggcca ggatgacggt  780
gcgatctaca cggctgtgcg gccgtgggga atcgccaacg tccggccta catttatgcc  840
aacatcacgg gctccgacaa cgtgacatg cgctctcgcg cgctggttac gaacaagccg  900
tacgtcaacg gcaatgcctc gtccatcacg caagccgtca acgttcactt cactcctgga  960
aagagcgttc gcatcaccaa gttttgtcgg ggtgcctcgt cggatgcgtt ttccaaccct 1020
cagcagatcg ccaagcaggc ttgttcgacc gcccaggcca acgatatgt gaagtcgctg 1080
cgttccacgt tgccgagtg ggccagcgtc atgccggatg actctgtcga tgactttacc 1140
ttccccagca atggcactct gcccgcagat gagtacatca tcgaatcgca aatcatctcc 1200
gtggcgaata cgtactatct cttgcagaac acggtcggca gaacgccat caatgcatcc 1260
tcgacaccg agctgaacaa ggactccatc gccgtcggtc gtctgacttc ggaatcgtac 1320
gccggtatga tcttctggga cgccgacgtc tggatgcaac cgggtcttgt cgcgtcccat 1380
cccgaggcgg cccagcgcat caccaactat cgagtggcca aatatcccca ggccaaagcg 1440
aacgttgcga ctgcctatca gagctctaag aaccagacaa acttctcccc ggacgcagct 1500
gtttactctt ggacgagtgc tcggtatgga aactgcactg tcaccggtcc ttgctgggat 1560
tacgagtatc atttgaacgg cgatattgga ctgtccatca tcaatcagta tgtggccagc 1620
ggtgacactc agaccttcaa ggagaagctc ttcccggttt tcgactccgt tgcgacactt 1680
tactcgaata ttgttcagaa gaatggctcg tcgtggactt tgactaacat gactgatcct 1740
gtatgtctct cccccttgtct cttgtctctt gttttttttt tttttttttt tttttttttt 1800
tttttttttt tttttttttt tttttttttt tttttttttt tttttttttt tttttttttt 1860
tttttttttt tttttttttt tttttttttt tttttttttt tttttttttt tttttttttt 1920
tttttttttt tttttttttt tttttttttt tttttttttt tttttttttt tttttttttt 1980
tttttttttt tttttttggt ttgtgtgctt ggctgacgtg tctaggatga atatgcaaac 2040
caggtcgatg ccggtggtta caccatgccc ctgattgctc agacgctgtt gtacgccagc 2100
tctttccgcc agcaattcgg tcttgagacc aacgacacgt ggaatgaat tgcacaggca 2160
gtcttggtga tccgcagaa tggtgtcacg ctgaattca ccaccatgaa cggaagtgct 2220
gtggtcaagc aggccgacgt ggtgctggac acttatcctc tgggttatac acacaactac 2280
gggcccacag atgctctgaa tgacttggac tacgtgagtg aaacgacgcc tttctgatgg 2340
gatcctggag ttactgactt gaccagtatg ccaacaggca atcgcccgac ggccctgcca 2400
tgacctggac catcttctcc gtcgtcgcca accaaatctc tccttcgggc tcgtcctcgt 2460
acacgtacgc ccagtacgcc ttcagcccct acgctcgcgc acccttctac cagctttccg 2520
agcagttgat cgacgacgcc tcgctcaacg gcgcactca cctgcctac ccgttcttga 2580
ccggccacgg cggtgccctc caagtcaacc ttttcgggta cctgggattc cgctacctcc 2640
ctgacaatgt catccacatt gatcccaacc ttccaccaca aatcccccac atcacctacc 2700
gcaccttcta ctggcgcggc tggcccatca ccgccgcctc cacctacacc cacacgacgc 2760
```

```
tcagccgagc ctggaacgtc tcgtccctcg acagcgccga ccccaaattc gccaacgcct    2820
ccatccccgt ccacgtcggc ctcgaatcga acgtgaccgt ctaccgtctc ccgtcaacg     2880
gcaccctcac cgtccccaac cgcatggtcg gctccaagaa cactctcgct ggcaacatgg    2940
tgcagtgccg tcccgtccaa tccatggacg gctatcaacc cggccaattc cccatctccg    3000
tcgtcgacgg tgcctcctcc acgaaatggc aacctctcta ctctgcgaac gtctcctccg    3060
tgacagttac tctgtcctcg tcagccgtcg gcaagagtgt gaacgggttc tacttcgact    3120
gggcgcaaaa cccacccgtc aacgccgcgg tggtcttcca caactcttcc tttgcacaga    3180
accccgccac gacgttctcg ttcgacaacc cttccgccag tggcaacttg tactccgttg    3240
tttcggtcct gaaggatatc caattgtccg atccctatga tcctgcaact acagacctgg    3300
acgtcatcgc cattccaaag ggaaatacca cgaactaac tctttcctcg cccgtccctg     3360
ccgcgagata cgccacgctc ttcatccagg gtaaccaggc gaacagtccc gcggaggtgg    3420
ctgcgaagaa cggcacgggc gcgacggtcg ccgagtgggc gattctaggg caggaggtgc    3480
agaataacgg ttacggggat cagattgaag cgagaagact cgatgtgagg ggcgcggctg    3540
cgttgtcggg gatggggagt ttcacgcagc ggaggaagag gaagatgatt ttgccgcggt    3600
tcgattag                                                             3608

SEQ ID NO: 23           moltype = AA  length = 1089
FEATURE                 Location/Qualifiers
source                  1..1089
                        mol_type = protein
                        organism = Talaromyces leycettanus
SEQUENCE: 23
MQSKLLALLP LLLQLPAVSG TSANARINRC VKKHAGGKTP SGPSNNTYQT RFPGVTWDQD      60
NWCLSTTTLD QGHYESRGSV ANGYLGINVA SVGPFFEFDT PVDGDVINGW PLFDRRMSFA     120
TISGFWDQQP TTNGSNFPWL YQYGGESVIS GVPHWSGLIL DLGDNTYLDA TVDSRTISGF     180
STTYDFKSGV LSWSYQWTPA GNMGSYNITY RLFAHKLYVN QAVVDMEVVS STEAKATVVN     240
VIDGASAVRT DFVESGQDDG AIYTAVRPWG IANVTAYIYA NITGSDNVDM RSRALVTNKP     300
YVNGNASSIT QAVNVHFTPG KSVRITKFVG GASSDAFSNP QQIAKQACST AQANGYVKSL     360
RSHVAEWASV MPDDSVDDFT FPSNGTLPAD EYIIESQIIS VANTYYLLQN TVGKNAINAS     420
SSTELNKDSI AVGGLTSESY AGMIFWDADV WMQPGLVASH PEAAQRITNY RVAKYPQAKA     480
NVATAYQSSK NQTNFSPDAA VYSWTSARYG NCTATGPCWD YEYHLNGDIG LSIINQYVAS     540
GDTQTFKEKL FPVFDSVATL YSNIVQKNGS SWTLTNMTDP DEYANQVDAG GYTMPLIAQT     600
LLYANSFRQQ FGLETNDTWN EIAQDVLVIR ENGVTLEFTT MNGSAVVKQA DVVLDTYPLG     660
YTHNYGPTDA LNDLDYYANR QSPDGPAMTW AIFSVVANQI SPSGCSAYTY AQYAFSPYAR     720
APFYQLSEQL IDDASLNGGT HPAYPFLTGH GGALQVNLFG YLGFRYLPDN VIHIDPNLPP     780
QIPHITYRTF YWRGWPITAA STYTHTTLSR AWNVSSLDSA DPKFANASIP VHVGLESNVT     840
VYRLPVNGTL TVPNRMVGSK NTLAGNMVQC RPVQSMDGYQ PGQFPISVVD GASSTKWQPL     900
YSANVSSVTV TLSSSAVGKS VNGFYFDWAQ NPPVNAAVVF HNSSFAQNPA TTFSFDNPSA     960
SGNLYSVVSV LKDIQLSDPY DPATTDLDVI AIPKGNTTNV TLSSPVPAAR YATLFIQGNQ    1020
ANSPAEVAAK NGTGATVAEW AILGQEVQNN GYGDQIEARR LDVRGAAALS GMGSFTQRRK    1080
RKMILPRFD                                                            1089

SEQ ID NO: 24           moltype = DNA  length = 27
FEATURE                 Location/Qualifiers
misc_feature            1..27
                        note = PCR primer
source                  1..27
                        mol_type = other DNA
                        organism = synthetic construct
SEQUENCE: 24
gaattcgagc tcggtacctt gaagttc                                         27

SEQ ID NO: 25           moltype = DNA  length = 31
FEATURE                 Location/Qualifiers
misc_feature            1..31
                        note = PCR primer
source                  1..31
                        mol_type = other DNA
                        organism = synthetic construct
SEQUENCE: 25
ggtggatccc cagttgtgta tatagaggat t                                    31

SEQ ID NO: 26           moltype = DNA  length = 26
FEATURE                 Location/Qualifiers
misc_feature            1..26
                        note = PCR primer
source                  1..26
                        mol_type = other DNA
                        organism = synthetic construct
SEQUENCE: 26
tggccggcgc ggctgggtcg actcta                                          26

SEQ ID NO: 27           moltype = DNA  length = 29
FEATURE                 Location/Qualifiers
misc_feature            1..29
                        note = PCR primer
source                  1..29
                        mol_type = other DNA
                        organism = synthetic construct
```

-continued

```
SEQUENCE: 27
gaccatgatt acgccaagct tttgaagtt                                         29

SEQ ID NO: 28          moltype = DNA  length = 25
FEATURE                Location/Qualifiers
misc_feature           1..25
                       note = PCR primer
source                 1..25
                       mol_type = other DNA
                       organism = synthetic construct
SEQUENCE: 28
ctatatacac aactggggat ccacc                                             25

SEQ ID NO: 29          moltype = DNA  length = 26
FEATURE                Location/Qualifiers
misc_feature           1..26
                       note = PCR primer
source                 1..26
                       mol_type = other DNA
                       organism = synthetic construct
SEQUENCE: 29
tagagtcgac ccagccgcgc cggcca                                            26

SEQ ID NO: 30          moltype = DNA  length = 62
FEATURE                Location/Qualifiers
misc_feature           1..62
                       note = PCR primer
source                 1..62
                       mol_type = other DNA
                       organism = synthetic construct
SEQUENCE: 30
ctatatacac aactggggat ccaccatgca gtcaaagctc ctggctctgc tgccgcttct       60
gc                                                                      62

SEQ ID NO: 31          moltype = DNA  length = 65
FEATURE                Location/Qualifiers
misc_feature           1..65
                       note = PCR primer
source                 1..65
                       mol_type = other DNA
                       organism = synthetic construct
SEQUENCE: 31
ctatatacac aactggggat ccaccatgta tagtgcaacg ctacttcagg ccctgtgcct       60
tctgc                                                                   65

SEQ ID NO: 32          moltype = DNA  length = 52
FEATURE                Location/Qualifiers
misc_feature           1..52
                       note = PCR primer
source                 1..52
                       mol_type = other DNA
                       organism = synthetic construct
SEQUENCE: 32
tagagtcgac ccagccgcgc cggccactaa tcgaaccgcg gcaaaatcat ct               52

SEQ ID NO: 33          moltype = DNA  length = 50
FEATURE                Location/Qualifiers
misc_feature           1..50
                       note = PCR primer
source                 1..50
                       mol_type = other DNA
                       organism = synthetic construct
SEQUENCE: 33
tagagtcgac ccagccgcgc cggccatcaa ctcaatatcg cccactccgc                  50

SEQ ID NO: 34          moltype = AA   length = 1034
FEATURE                Location/Qualifiers
source                 1..1034
                       mol_type = protein
                       organism = Talaromyces cellulolyticus
SEQUENCE: 34
MHSAALLQAL CLLPLVAGLP FNERVDQILR SYSPKNLESR STKHGNSYQT QFSGVTWDQR       60
NWRLQSTVLD QGHYESRGSI ANGYIGLNVA GAGPFFELDT AVDGDVINGW PLFSRRQTFA      120
GLAGFYDLQP TTNGSNFPWL SQYGDDSAIS GVPHWGGLIL DLGDGEYLDA TVDNSTISDY      180
TTTYDYKAGV LSWDYKWTPK NSKASFGINY KIFANKLDVN QAVVQLSITP SANGSGSVVN      240
VIDGYSAVRT DFVSSGNESD VIYTAVKPVG VNNVTAWIYA ALDGDEAFDF SSAELVNDKP      300
YVHQNDSSIA QSVNVTFTAG TTITINKFVG AASTDAFPDP QSTAREAAMT ARRRGFDDLF      360
RSHVSEWAQV MPDDSVDDFT LANGTLPNDT FIIESAVMAV VNPYYLLQNT VGANALRRVN      420
NAPVNDWSIP VGGLTSDSYA GQIFWDADVW MQPGLVAAFP ESAKRITNYR TAKYSQALEN      480
```

```
AKTAYTSSQN   QTSFSSDAAI   YSWTSGRYGN   CTATGPCWDY   EYHLNGDIGI   SLVNQWVVSG    540
DNETFKNTHF   PIYNSIATLY   GDLLKKNGSY   YTLTNMTDPD   EYANNVDAGG   YTMTLISQTL    600
SNANAFRKQF   GMDENTTWTE   MADNILLIRE   NDVTLEYTTM   NNSVAVKQAD   VILSTFPLDY    660
TKNYTTSAAL   NDLDYYALKQ   SPDGPGMTYA   IFSIVANDVS   PSGCSAYTYA   QYSYDPYIRG    720
PFFQFSEQLL   DDYTANGGTH   PAFPPLTGHG   GANQVVLYGY   LGLRLLPDDM   LHIDPNLPPQ    780
IPSVKYRTFY   WRGWPIQAAS   NYTHTTIQRA   TSVAPLSTAD   PVYANTSISV   SVGQNTANST    840
TYSLPVNGSA   IVVPNRQIGS   INTVTGNIAQ   CVSVLSTDAY   QPGQYPISAV   DGAASTKWQP    900
EFAANVSSLT   VDLTSSNASS   VSGFYFDWAQ   APPTNITVLL   HNSSSAALTS   SSTHGGSSSV    960
SLNITTSNPY   DASSYDANVI   ALSSSNTTNY   TFPAPVAKPR   YATLFVQGNQ   ALDETDTKAG   1020
NGTGATVAEW   AILS                                                            1034

SEQ ID NO: 35           moltype = AA  length = 1040
FEATURE                 Location/Qualifiers
source                  1..1040
                        mol_type = protein
                        organism = Talaromyces verruculosus
SEQUENCE: 35
MYSATLLQAL   CLLPLVAGLP   FNERVDQILR   SYSPKNLESR   STKHGNNTKH   GNSYQTQFSG    60
VTWDQRNWRL   QSTVLDQGHY   ESRGSIANGY   IGLNVAGAGP   FFELDTAVDG   DVINGWPLFS   120
RRQTFAGLAG   FYDLQPTTNG   SNFPWLDQYG   DDSAISGVPH   WGGLILDLGD   GEYLDATVDN   180
STISDYRTTY   DYKAGVLSWD   YKWTPKNSKG   SFGINYKIFA   NKLDVNQAVV   QLSITPSANG   240
SASVVNVIDG   YSAVRTDFVS   SGNESDVIYT   AVKPVGVNNV   TAWIYAALDG   DEAFDFSSAE   300
LVNDKPYVHQ   NDSSIAQSVN   VSFTAGTTVT   INKFVGAAST   DAFPDPQSTA   REAALTARRR   360
GFDDLFRSHI   SEWAQVMPDD   SVDDFTLANG   TLPNDRFIIE   SAVMAVVNPY   YLLQNTVGPN   420
ALRRVNNAPV   NDWSIPVGGL   TSDSYAGQIF   WDADVWMQPG   LVAAFPESAK   RITNYRTAIY   480
SQALENAKTA   YTSSQNQTSF   SSDAAIYSWT   SGRYGNCTAT   GPCWDYEYHL   NGDIGISLVN   540
QWVVSGDNET   FKSTHFPIYN   SIATLYGDLL   KKNGSYYTLT   NMTDPDEYAN   NVDAGGYTMT   600
LISQTLSNAN   AFRKQFGMDE   NTTWTEMAEN   ILLIRENDVT   LEYTTMNNSV   AVKQADVILS   660
TFPLDYTKNY   TTSAALNDLD   YYALKQSPDG   PGMTYAIFSI   VANDVSPSGC   SAYTYAQYSY   720
DPYIRGPFFQ   FSEQLLDDYT   ANGGTHPAFP   FLTGHGGANQ   VVLYGYLGLR   LLPDDDMLHID  780
PNLPPQIPSV   KYRTFYWRGW   PIQAASNYTH   TTIQRATTVA   PLSTADQAYA   NTSISVSVGQ   840
NTANSTTYSL   PVNGSAIVVP   NRQIGSINTV   AGNIAQCVSV   LSTDAYQPGQ   YPISAVDGAA   900
STKWQPEFAA   NVNSLTVDLT   SSNASSVSGF   YFDWAQAPPT   NITVLLHNSS   SVALTSSSTH   960
GGSSSVSLNI   TISNPYDALS   YDANVIALSS   SNTTNYTFPA   PVAKPRYATL   LVQGNQALDE  1020
TDTKAGNGTG   ATVAEWAILS                                                    1040
```